US010220069B2

(12) United States Patent
Hussain et al.

(10) Patent No.: US 10,220,069 B2
(45) Date of Patent: Mar. 5, 2019

(54) COMPOSITIONS AND METHODS FOR TREATING DIABETES

(71) Applicant: THE JOHNS HOPKINS UNIVERSITY, Baltimore, MD (US)

(72) Inventors: Mehboob Hussain, Baltimore, MD (US); Prosenjit Mondal, Baltimore, MD (US); Woo-Jin Song, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/113,450

(22) PCT Filed: Jan. 22, 2015

(86) PCT No.: PCT/US2015/012440
§ 371 (c)(1),
(2) Date: Jul. 22, 2016

(87) PCT Pub. No.: WO2015/112703
PCT Pub. Date: Jul. 30, 2015

(65) Prior Publication Data
US 2017/0007666 A1   Jan. 12, 2017

Related U.S. Application Data

(60) Provisional application No. 61/930,181, filed on Jan. 22, 2014, provisional application No. 61/971,743, filed on Mar. 28, 2014.

(51) Int. Cl.
*A61K 38/16* (2006.01)
*A61K 38/08* (2019.01)
*A61K 31/4412* (2006.01)
*C12N 15/113* (2010.01)

(52) U.S. Cl.
CPC .......... *A61K 38/16* (2013.01); *A61K 31/4412* (2013.01); *A61K 38/08* (2013.01); *C12N 15/113* (2013.01); *C12N 2310/11* (2013.01); *C12N 2310/14* (2013.01); *C12N 2310/141* (2013.01)

(58) Field of Classification Search
CPC .... A61K 31/4412; A61K 38/08; A61K 38/16; A61K 38/17; C12N 15/113; C12N 2310/11; C12N 2310/14; C12N 2310/141
See application file for complete search history.

(56) References Cited

U.S. PATENT DOCUMENTS

| 7,625,869 | B2* | 12/2009 | Kitada | C07K 14/4703 514/1.1 |
| 7,786,083 | B2* | 8/2010 | Asami | C07K 14/4703 514/19.8 |
| 7,960,348 | B2* | 6/2011 | Asami | C07K 14/4748 514/19.8 |
| 8,361,968 | B2* | 1/2013 | Kitada | C07K 14/47 514/19.3 |
| 8,404,643 | B2* | 3/2013 | Asami | C07K 14/4703 514/19.5 |
| 8,916,681 | B2* | 12/2014 | Millar | A61K 38/1709 530/327 |
| 2011/0039786 | A1* | 2/2011 | Fujii | C07K 14/4703 514/17.8 |
| 2011/0046068 | A1* | 2/2011 | Millar | A61K 38/1709 514/19.3 |

FOREIGN PATENT DOCUMENTS

| EP | 2388012 | * | 5/2010 | ............ A61K 38/04 |
| WO | 2004087622 A2 | | 10/2004 | |

OTHER PUBLICATIONS

George, J., et al. (2010) "Hypothesis: Kisspeptin Mediates Male Hypogonadism in Obesity and Type 2 Diabetes", Neuroendocrinology, vol. 91, No. 4, pp. 302-307.
Millar, R., et al. (2010) "Kisspeptin antagonists: Unraveling the role of kisspeptin in reproductive physiology", Brain Research, vol. 1364, pp. 81-89.
Pineda, R., et al. (2010) "Critical Roles of Kisspeptins in Female Puberty and Preovulatory Gonadotropin Surges as Revealed by a Novel Antagonist", Endocrinology, vol. 151, No. 2, pp. 722-730.
Rabijewski, M., et al. (2013) "The Incidence of Hypogonadotropic Hypogonadism in Type 2 Diabetic Men in Polish Population", BioMed Research International, vol. 2013, Article ID 767496, 6 pages.
Roseweir, A., et al. (2009) "Discovery of Potent Kisspeptin Antagonists Delineate Physiological Mechanisms of Gonadotropin Regulation", The Journal of Neuroscience, vol. 29, No. 12, pp. 3920-3929.
Ahren, B., et al., Impaired glucose tolerance (IGT) is associated with reduced insulin-induced suppression of glucagon concentrations. Diabetologia 44, 1998-2003, doi:10.1007/s001250100003 (2001).
Akinci, A., et al.,, (2012). Plasma kisspeptin levels in girls with premature thelarche. J. Clin. Res. Pediatr. Endocrinol. 4, 61-65.
Alonso, L. C. et al. Glucose infusion in mice: a new model to induce beta-cell replication. Diabetes 56, 1792-1801, doi:db06-1513 [pii] 10.2337/db06-1513 (2007).
Barrett, T., et al. (2005). NCBI GEO: mining millions of expression profiles—database and tools. Nucleic Acids Res. 33 (Database issue), D562-D566.
Basu, A. et al. Effects of a change in the pattern of insulin delivery on carbohydrate tolerance in diabetic and nondiabetic humans in the presence of differing degrees of insulin resistance. J Clin Invest 97, 2351-2361, doi:10.1172/JCI118678 (1996).

(Continued)

*Primary Examiner* — Marcela M Cordero Garcia
(74) *Attorney, Agent, or Firm* — Johns Hopkins Technology Ventures

(57) ABSTRACT

The present invention relates to the field of diabetes mellitus. More specifically, the present invention provides compositions and methods useful for treating diabetes. In another embodiment, a method for treating type 2 diabetes mellitus or pre-diabetes in a patient comprises administering to the patient an effective amount of inhibitor of kisspeptin 1 and/or proteolytic derivatives thereof.

9 Claims, 33 Drawing Sheets
Specification includes a Sequence Listing.

(56) References Cited

OTHER PUBLICATIONS

Bowe, J.E., et al., (2012). GPR54 peptide agonists stimulate insulin secretion from murine, porcine and human islets. Islets 4, 20-23.
Brand, C. L. et al. Role of glucagon in maintenance of euglycemia in fed and fasted rats. Am J Physiol 269, E469-477 (1995).
Brothers, K. J. et al. Rescue of obesity-induced infertility in female mice due to a pituitary-specific knockout of the insulin receptor. Cell Metab 12, 295-305, doi:S1550-4131(10)00270-6 [pii] 10.1016/j.cmet.2010.06.010 (2010).
Bruning, J. C. et al. Development of a novel polygenic model of NIDDM in mice heterozygous for IR and IRS-1 null alleles. Cell 88, 561-572, doi:S0092-8674(00)81896-6 [pii] (1997).
Cetkovi C., et al., (2012). Plasma kisspeptin levels in pregnancies with diabetes and hypertensive disease as a potential marker of placental dysfunction and adverse perinatal outcome. Endocr. Res. 37, 78-88.
Chan, Y. M. et al. GnRH-deficient phenotypes in humans and mice with heterozygous variants in KISS1/Kiss1. J Clin Endocrinol Metab 96, E1771-1781, doi:jc.2011-0518 [pii] 10.1210/jc.2011-0518 (2011).
Chen, M. et al. Increased glucose tolerance and reduced adiposity in the absence of fasting hypoglycemia in mice with liver-specific Gs alpha deficiency. J Clin Invest 115, 3217-3227, doi:10.1172/JCI24196 (2005).
D'Alessio, D. The role of dysregulated glucagon secretion in type 2 diabetes. Diabetes Obes Metab 13 Suppl 1, 126-132, doi:10.1111/j.1463-1326.2011.01449.x (2011).
Defronzo, R. A. & Abdul-Ghani, M. A. Preservation of beta-cell function: the key to diabetes prevention. J Clin Endocrinol Metab 96, 2354-2366, doi:jc.2011-0246 [pii] 10.1210/jc.2011-0246 (2011).
Drucker, D. J. The biology of incretin hormones. Cell Metab 3, 153-165, doi:S1550-4131(06)00028-3 [pii] 10.1016/j.cmet.2006.01.004 (2006).
Elquaamari, A., et al., (2013). Liver-derived systemic factors drive b cell hyperplasia in insulin-resistant states. Cell Rep. 3, 401-410.
Gonzalez, G.A., and Montminy, M.R. (1989). Cyclic AMP stimulates somatostatin gene transcription by phosphorylation of CREB at serine 133. Cell 59, 675-680.
Gottsch, M. L. et al. A role for kisspeptins in the regulation of gonadotropin secretion in the mouse. Endocrinology 145, 4073-4077, doi:10.1210/en.2004-0431 en.2004-0431 [pii] (2004).
Hauge-Evans, A. C. et al. A role for kisspeptin in islet function. Diabetologia 49, 2131-2135, doi:10.1007/s00125-006-0343-z (2006).
He, L. et al. Metformin and Insulin Suppress Hepatic Gluconeogenesis by Inhibiting cAMP Signaling Through Phosphorylation of CREB Binding Protein (CBP) Cell 137, 635-646, doi:S0092-8674(09)00276-1 [pii] 10.1016/j.cell.2009.03.016 (2009).
Horikoshi, Y. et al. Dramatic elevation of plasma metastin concentrations in human pregnancy: metastin as a novel placenta-derived hormone in humans. J Clin Endocrinol Metab 88, 914-919 (2003).
Hussain, M. A. et al. Increased pancreatic beta-cell proliferation mediated by CREB binding protein gene activation. Mol Cell Biol 26, 7747-7759, doi:MCB.02353-05 [pii] 10.1128/MCB.02353-05 (2006).
Irwig, M. S. et al. Kisspeptin activation of gonadotropin releasing hormone neurons and regulation of KiSS-1 mRNA in the male rat. Neuroendocrinology 80, 264-272, doi:83140 [pii] 10.1159/000083140 (2004).
Jamison, R. A. et al. Hyperglucagonemia precedes a decline in insulin secretion and causes hyperglycemia in chronically glucose-infused rats. Am J Physiol Endocrinol Metab 301, E1174-1183, doi:ajpendo.00175.2011 [pii] 10.1152/ajpendo.00175.2011 (2011).
Jhala, U. S. et al. cAMP promotes pancreatic beta-cell survival via CREB-mediated induction of IRS2. Genes Dev 17, 1575-1580, doi:10.1101/gad.1097103 17/13/1575 [pii] (2003).
Kieffer, T.J., Heller, R.S., Leech, C.A., Holz, G.G., and Habener, J.F. (1997). Leptin suppression of insulin secretion by the activation of ATP-sensitive K+ channels in pancreatic beta-cells. Diabetes 46, 1087-1093.
Kirschner, L. S. et al. A mouse model for the Carney complex tumor syndrome develops neoplasia in cyclic AMP-responsive tissues. Cancer Res 65, 4506-4514, doi:65/11/4506 [pii] 10.1158/0008-5472.CAN-05-0580 (2005).
Lammert, E., Cleaver, O., and Melton, D. (2001). Induction of pancreatic differentiation by signals from blood vessels. Science 294, 564-567.
Lapatto, R. et al. Kiss1−/−mice exhibit more variable hypogonadism than Gpr54−/−mice. Endocrinology 148, 4927-4936, doi:en.2007-0078 [pii] 10.1210/en.2007-0078 (2007).
Laube, H., Fussganger, R. D., Maier, V. & Pfeiffer, E. F. Hyperglucagonemia of the isolated perfused pancreas of diabetic mice (db-db). Diabetologia 9, 400-402 (1973).
Lee, D.K., et al. (1999). Discovery of a receptor related to the galanin receptors. FEBS Lett. 446, 103-107.
Liu, Y. et al. A fasting inducible switch modulates gluconeogenesis via activator/coactivator exchange. Nature 456, 269-273, doi:nature07349 [pii] 10.1038/nature07349 (2008).
Liu, Z. et al. LC-MS/MS quantification of a neuropeptide fragment kisspeptin-10 (NSC 741805) and characterization of its decomposition product and pharmacokinetics in rats. J Chromatogr B Analyt Technol Biomed Life Sci 926, 1-8, doi:S1570-0232(13)00130-X [pii] 10.1016/j.jchromb.2013.02.027 (2013).
Livak, K. J. & Schmittgen, T. D. Analysis of relative gene expression data using real-time quantitative PCR and the 2(-Delta Delta C(T)) Method. Methods 25, 402-408, doi:10.1006/meth.2001.1262 S1046-2023(01)91262-9 [pii] (2001).
Logie, J.J., Denison, F.C., Riley, S.C., Ramaesh, T., Forbes, S., Norman, J.E., and Reynolds, R.M. (2012). Evaluation of kisspeptin levels in obese pregnancy as a biomarker for pre-eclampsia. Clin. Endocrinol. (Oxf.) 76, 887-893.
Longuet, C., et al. (2013). Liver-specific disruption of the murine glucagon receptor produces a-cell hyperplasia: evidence for a circulating a-cell growth factor. Diabetes 62, 1196-1205.
Louet, J.F., et al. (2010). The coactivator SRC-1 is an essential coordinator of hepatic glucose production. Cell Metab. 12, 606-618.
Martinez-Fuentes, A. J. et al. Expression of functional KISS1 and KISS1R system is altered in human pituitary adenomas: evidence for apoptotic action of kisspeptin-10. Eur J Endocrinol 164, 355-362, doi:EJE-10-0905 [pii] 10.1530/EJE-10-0905 (2011).
Meier, J. J., et al., (2010) Is the diminished incretin effect in type 2 diabetes just an epi-phenomenon, Diabetes, vol. 59, pp. 1117-1125.
Messanger, S. et al. Kisspeptin directly stimulates gonadotropin-releasing hormone release via G protein-coupled receptor 54. Proc Natl Acad Sci U S A 102, 1761-1766, doi:0409330102 [pii] 10.1073/pnas.0409330102 (2005).
Muir, A. I. et al. AXOR12, a novel human G protein-coupled receptor, activated by the peptide KiSS-1. J Biol Chem 276, 28969-28975, doi:10.1074/jbc.M102743200 M102743200 [pii] (2001).
Niswender, C. M. et al. Cre recombinase-dependent expression of a constitutively active mutant allele of the catalytic subunit of protein kinase A. Genesis 43, 109-119, doi:10.1002/gene.20159 (2005).
Novaira, H. J. et al. The gonadotropin-releasing hormone cell-specific element is required for normal puberty and estrous cyclicity. J Neurosci 31, 3336-3343, doi:31/9/3336 [pii] 10.1523/JNEUROSCI.5419-10.2011 (2011).
Novaira, H. J., Hoffman, G. E., Koo, Y., Wolfe, A. M. & Radovick, S. Reproductive abnormalities associated with deletion of Gpr54 in mouse GnRH neurons. Endocrinology suppl (2013).
Novaira, H. J., et al., Kisspeptin increases GnRH mRNA expression and secretion in GnRH secreting neuronal cell lines. Mol Cell Endocrinol 311, 126-134, doi:S0303-7207(09)00355-4 [pii] 10.1016/j.mce.2009.06.011 (2009).
Novaira, H.J., et al., (2013). Disrupted kisspeptin signaling in GnRH neurons leads to hypogonadotrophic hypogonadism. Mol. Endocrinol 28, 225-238.
Nyholm, B. et al. Assessment of insulin secretion in relatives of patients with type 2 (non-insulindependent) diabetes mellitus: evidence of early beta-cell dysfunction. Metabolism 49, 896-905, doi:S0026-0495(00)25796-X [pii] 10.1053/meta.2000.6737 (2000).

(56) References Cited

OTHER PUBLICATIONS

Ohtaki, T. et al. Metastasis suppressor gene KiSS-1 encodes peptide ligand of a G-protein-coupled receptor. Nature 411, 613-617, doi:10.1038/35079135 35079135 [pii] (2001).

Park, S., Jiang, H., Zhang, H. & Smith, R. G. Modification of ghrelin receptor signaling by somatostatin receptor-5 regulates insulin release. Proc Natl Acad Sci U S A 109, 19003-19008, doi:1209590109 [pii] 10.1073/pnas.1209590109 (2012).

Pita, J. et al. Circulating kisspeptin levels exhibit sexual dimorphism in adults, are increased in obese prepubertal girls and do not suffer modifications in girls with idiopathic central precocious puberty. Peptides 32, 1781-1786, doi:S0196-9781(11)00304-4 [pii] 10.1016/j.peptides.2011.07.016 (2011).

Poitout, V. & Robertson, R. P. Glucolipotoxicity: fuel excess and beta-cell dysfunction. Endocr Rev 29, 351-366, doi:er.2007-0023 [pii] 10.1210/er.2007-0023 (2008).

Qureshi, S.A., et al., (2004). A novel glucagon receptor antagonist inhibits glucagon-mediated biological effects. Diabetes 53, 3267-3273.

Roseweir, A. K. et al. Discovery of potent kisspeptin antagonists delineate physiological mechanisms of gonadotropin regulation. J Neurosci 29, 3920-3929, doi:29/12/3920 [pii] 10.1523/JNEUROSCI.5740-08.2009 (2009).

Seminara, S.B., and Kaiser, U.B. (2005). New gatekeepers of reproduction: GPR54 and its cognate ligand, KiSS-1. Endocrinology 146, 1686-1688.

Sherline, P., Lynch, A., and Glinsmann, W.H. (1972). Cyclic AMP and adrenergic receptor control of rat liver glycogen metabolism. Endocrinology 91, 680-690.

Silvestre, R. A., et al., Kisspeptin-13 inhibits insulin secretion without affecting glucagon or somatostatin release: study in the perfused rat pancreas. J Endocrinol 196, 283-290, doi:196/2/283 [pii] 10.1677/JOE-07-0454 (2008).

Smith, J.T., et al., (2006). KiSS-1 neurones are direct targets for leptin in the ob/ob mouse. J. Neuroendocrinol. 18, 298-303.

Song, W. J. et al. Exendin-4 stimulation of cyclin A2 in beta-cell proliferation. Diabetes 57, 2371-2381, doi:db07-1541 [pii] 10.2337/db07-1541 (2008).

Song, W. J. et al. Snapin mediates incretin action and augments glucose-dependent insulin secretion. Cell Metab 13, 308-319, doi:S1550-4131(11)00046-5 [pii] 10.1016/j.cmet.2011.02.002 (2011).

Song, W. J., et al., Pancreatic beta-cell response to increased metabolic demand and to pharmacologic secretagogues requires EPAC2A. Diabetes, doi:db12-1394 [pii] 10.2337/db12-1394 (2013).

Sorenson, H. et al. Immunoneutralization of endogenous glucagon reduces hepatic glucose output and improves long-term glycemic control in diabetic ob/ob mice. Diabetes 55, 2843-2848, doi:55/10/2843 [pii] 10.2337/db06-0222 (2006).

Stafford, L. J., et al., Identification and characterization of mouse metastasis-suppressor KiSS1 and its G-protein-coupled receptor. Cancer Res 62, 5399-5404 (2002).

Talchai, C., et al., Pancreatic β cell dedifferentiation as a mechanism of diabetic β cell failure. Cell 150, 1223-1234 (2012).

Tang, G. et al. Go2 G protein mediates galanin inhibitory effects on insulin release from pancreatic beta cells. Proc Natl Acad Sci U S A 109, 2636-2641, doi:1200100109 [pii] 10.1073/pnas.1200100109 (2012).

Thorel, F. et al. Conversion of adult pancreatic alpha-cells to beta-cells after extreme beta-cell loss. Nature 464, 1149-1154, doi:nature08894 [pii] 10.1038/nature08894 (2010).

Tschritter, O. et al. The prevalent Glu23Lys polymorphism in the potassium inward rectifier 6.2 (KIR6.2) gene is associated with impaired glucagon suppression in response to hyperglycemia. Diabetes 51, 2854-2860 (2002).

Vikman, J. & Ahren, B. Inhibitory effect of kisspeptins on insulin secretion from isolated mouse islets. Diabetes Obes Metab 11 Suppl 4, 197-201, doi:DOM1116 [pii] 10.1111/j.1463-1326.2009.01116.x(2009).

Wahab, F., et al., (2011). Study on the effect of peripheral kisspeptin administration on basal and glucose-induced insulin secretion under fed and fasting conditions in the adult male rhesus monkey (*Macaca mulatta*). Horm. Metab. Res. 43, 37-42.

Wang, Y. et al. Augmented glucose-induced insulin release in mice lacking G(o2), but not G(o1) or G(i) proteins. Proc Natl Acad Sci U S A 108, 1693-1698, doi:1018903108 [pii] 10.1073/pnas.1018903108 (2011).

Wicksteed, B. et al. Conditional gene targeting in mouse pancreatic ss-Cells: analysis of ectopic Cre transgene expression in the brain. Diabetes 59, 3090-3098, doi:db10-0624 [pii] 10.2337/db10-0624 (2010).

Wolfe, A. M., Wray, S., Westphal, H. & Radovick, S. Cell-specific expression of the human gonadotropin-releasing hormone gene in transgenic animals. J Biol Chem 271, 20018-20023 (1996).

Xie, T., Chen, M., Zhang, Q. H., Ma, Z. & Weinstein, L. S. Beta cell-specific deficiency of the stimulatory G protein alpha-subunit Gsalpha leads to reduced beta cell mass and insulin-deficient diabetes. Proc Natl Aced Sci U S A 104, 19601-19606, doi:0704796104 [pii] 10.1073/pnas.0704796104 (2007).

Yi, P., Park, J. S. & Melton, D. A. Betatrophin: A Hormone that Controls Pancreatic beta Cell Proliferation. Cell 153, 747-758, doi:S0092-8674(13)00449-2 [pii] 10.1016/j.ce11.2013.04.008 (2013).

Zhang, X., et al. (2005). Genome-wide analysis of cAMP-response element binding protein occupancy, phosphorylation, and target gene activation in human tissues. Proc. Natl. Acad. Sci. USA 102, 4459-4464.

Zhao, A. et al. Galphao represses insulin secretion by reducing vesicular docking in pancreatic betacells. Diabetes 59, 2522-2529, doi:db09-1719 [pii] 10.2337/db09-1719 (2010).

* cited by examiner

K234 improves GTT in db/db mice

COMPOSITIONS AND METHODS FOR TREATING DIABETES

CROSS-REFERENCE TO RELATED APPLICATIONS

This application is a 35 U.S.C. § 371 U.S. national entry of International Application PCT/US2015/012440, having an international filing date of Jan. 22, 2015, which claims the benefit of U.S. Provisional Application No. 61/930,181, filed Jan. 22, 2014, and U.S. Provisional Application No. 61/971,743, filed Mar. 28, 2014, the content of each of the aforementioned applications is herein incorporated by reference in their entirety.

STATEMENT OF GOVERNMENTAL INTEREST

This invention was made with government support under grant no. AR057759, HD068777, HD066432, DK079637, DK084949, DK090816, DK090245, and DK081472awarded by the National Institutes of Health. The government has certain rights in the invention.

FIELD OF THE INVENTION

The present invention relates to the field of diabetes mellitus. More specifically, the present invention provides compositions and methods useful for treating diabetes.

INCORPORATION-BY-REFERENCE OF MATERIAL SUBMITTED ELECTRONICALLY

This application contains a sequence listing. It has been submitted electronically via EFS-Web as an ASCII text file entitled "P12315-03_ST25.txt." The sequence listing is 8,298 bytes in size, and was created on Jan. 22, 2015. It is hereby incorporated by reference in its entirety.

BACKGROUND OF THE INVENTION

Diabetes mellitus is a chronic metabolic disorder characterized by the presence of hyperglycemia (raised blood glucose concentrations). The prevalence of type 2 or non-insulin-dependent diabetes mellitus (NIDDM) (characterized by impaired insulin action and impaired insulin secretion), is high and is growing at an alarming rate. The global burden of diabetes mellitus is expected to reach 300 million by the year 2025, with more than 90% of these individuals having type 2 diabetes.

The predominant pathophysiological defects leading to hyperglycemia in type 2 diabetes are impaired insulin action (insulin resistance) and impaired insulin secretion (beta-cell dysfunction). Treating hyperglycemia is therapeutically important in diabetes mellitus in order to prevent symptoms caused by the raised blood glucose concentrations, such as polyuria (excessive urination) and polydipsia (excessive thirst), and to reduce the risk of diabetic complications. The chronic hyperglycemia of diabetes mellitus is associated with significant, often devastating long-term complications in the eyes, kidneys, nerves and blood vessels. The largest study of pharmacotherapy in type 2 diabetes, The United Kingdom Prospective Diabetes Study (UKPDS), demonstrated that lowering blood glucose concentrations with pharmacotherapy in type 2 diabetes reduces the risk of complications. 352 LANCET 837-53 (1998). The study showed that there was no lower threshold for the benefits of glucose lowering and that any additional glucose lowering would further reduce the risk of development of diabetic complications.

Thus, there is a need to find new and improved regimens for the treatment of type 2 diabetes.

SUMMARY OF THE INVENTION

The present invention is based, at least in part, on the discovery that kisspeptin1 and its proteolytic fragments (K54, K10) inhibit glucose stimulated insulin secretion (GSIS) from cultured islets in a dose- and Kiss1R-dependent manner at nanomolar concentrations. Furthermore, mice rendered glucose intolerant by high-fat-content diet (HFD) or leptin receptor defective diabetic ($Lepr^{db/db}$) mice are hyperglucagonemic, exhibit increased liver kisspeptin1, and harbor in their circulation functional kisspeptin bioactivity equivalent to nanomolar concentrations of synthetic kisspeptin. In these mice, selective liver kisspeptin 1knock-down derepresses GSIS and improves glucose tolerance (GT). Importantly, humans with T2DM also exhibit increased liver and plasma kisspeptin1 levels. Furthermore, mice selectively lacking pancreas Kiss1R, when fed a HFD, as compared to control counterparts, show improved GT owing to increased GSIS.

Accordingly, in one aspect, the present invention provides methods and compositions useful for treating diabetes in a patient. In one embodiment, the methods and compositions of the present invention are useful for treating type 2 diabetes. In another embodiment, the present invention is useful for treating pre-diabetes in a patient, i.e., impaired glucose tolerance and/or impaired fasting glucose. The patients can be treating using kisspeptin1 antagonists. In other embodiments, the patients can be treating using GPR54 receptor (i.e., kisspeptin1 receptor) antagonists. It is understood that reference to a kisspeptin1 antagonists can refer, as the context dictates, to an antagonist of kisspeptin1 and/or an antagonist of GPR54 (kisspeptin1) receptor. In certain embodiments, a given agent refers to both types of antagonists. For example, a neutralizing antibody that binds to GPR54 is both a GPR54 receptor antagonist and a kisspeptin1 antagonist.

In a specific embodiment, a method for treating type 2 diabetes or pre-diabetes in a patient comprises the step of administering to the patient composition comprising an effective amount of a GPR54 receptor antagonist. In certain embodiments, the GPR54 receptor antagonist is a derivative of kisspeptin. In a specific embodiment, the Kisspeptin derivative is K234. In an alternative embodiment, the GPR54 receptor antagonist is a small molecule. In a more specific embodiment, the small molecule is a derivative of 2-Acylamino-4,6,diphenylpyridine.

In another embodiment, the present invention provides a GPR54 receptor antagonist for use in a method of treating type 2 diabetes or pre-diabetes in a patient, the method comprising administering to the patient an effective amount of the GPR54 receptor antagonist. In a specific embodiment, the GPR54 receptor antagonist is a derivative of Kisspeptin1. In a more specific embodiment, the Kisspeptin derivative is K234. In certain embodiments, the Kisspeptin derivative comprises SEQ ID NO:37.

In another embodiment, a method for treating type 2 diabetes mellitus or pre-diabetes in a patient comprises administering to the patient an effective amount of inhibitor of kisspeptin1 and/or proteolytic derivatives thereof. In certain embodiments, the proteolytic derivatives of kisspeptin1 comprise K54, K14, K13, and K10.

The present invention also provides methods for treating type 2 diabetes mellitus or pre-diabetes in a patient comprising administering to the patient an agent that inhibits kisspeptin1 production in the liver. In particular embodiments, the agent comprises an inhibitory nucleic acid molecule that reduces liver production of kisspeptin1. The inhibitory nucleic acid molecule can comprise a short hairpin or interfering RNA (shRNA or siRNA) molecule, a microRNA (miRNA) molecule, or an antisense molecule. In a specific embodiment, the present invention provides an antisense molecule for use in a method of treating type 2 diabetes or pre-diabetes in a patient, the method comprising administering to the patient a composition comprising an antisense molecule that inhibits kisspeptin1 expression in the liver. In particular embodiments, the antagonist/inhibitor/agent of the present invention does not cross the blood brain barrier.

Insulin treatment in L-Δprkar1a mice downregulates liver kisspeptin1 expression (I-K). I Plasma glucose levels 60 min after insulin treatment (1 IU/kg ip) in L-Δprkar1a mice. L-Δprkar1a mice respond to a large dose of insulin with reduction in plasma glucose at 60 min after insulin treatment (mean+SEM, *p<0.05). J qRT-PCR of Kiss1 in liver tissue of prkar1afl/fl mice and in L-ΔPrkar1a mice 60 min after treatment with vehicle (PBS) or insulin (1 IU/kg ip). Kiss1 expression is upregulated in L-ΔPrkar1a as compared to prkar1afl/fl mice. Insulin treatment downregulates Kiss1 expression in L-ΔPrkar1a (mean+SEM, *p<0.05). K Representative liver IB of kisspeptin (top) of prkar1afl/fl and L-ΔPrkar1a mice in the fed state; (bottom) of prkar1afl/fl mice and of L-ΔPrkar1a mice 60 min after treatment with vehicle (PBS) or insulin (1 IU/kg ip). L-ΔPrkar1a mouse livers exhibit elevated kisspeptin immunoreactivity, which is downregulated by insulin treatment.

Figure 9:
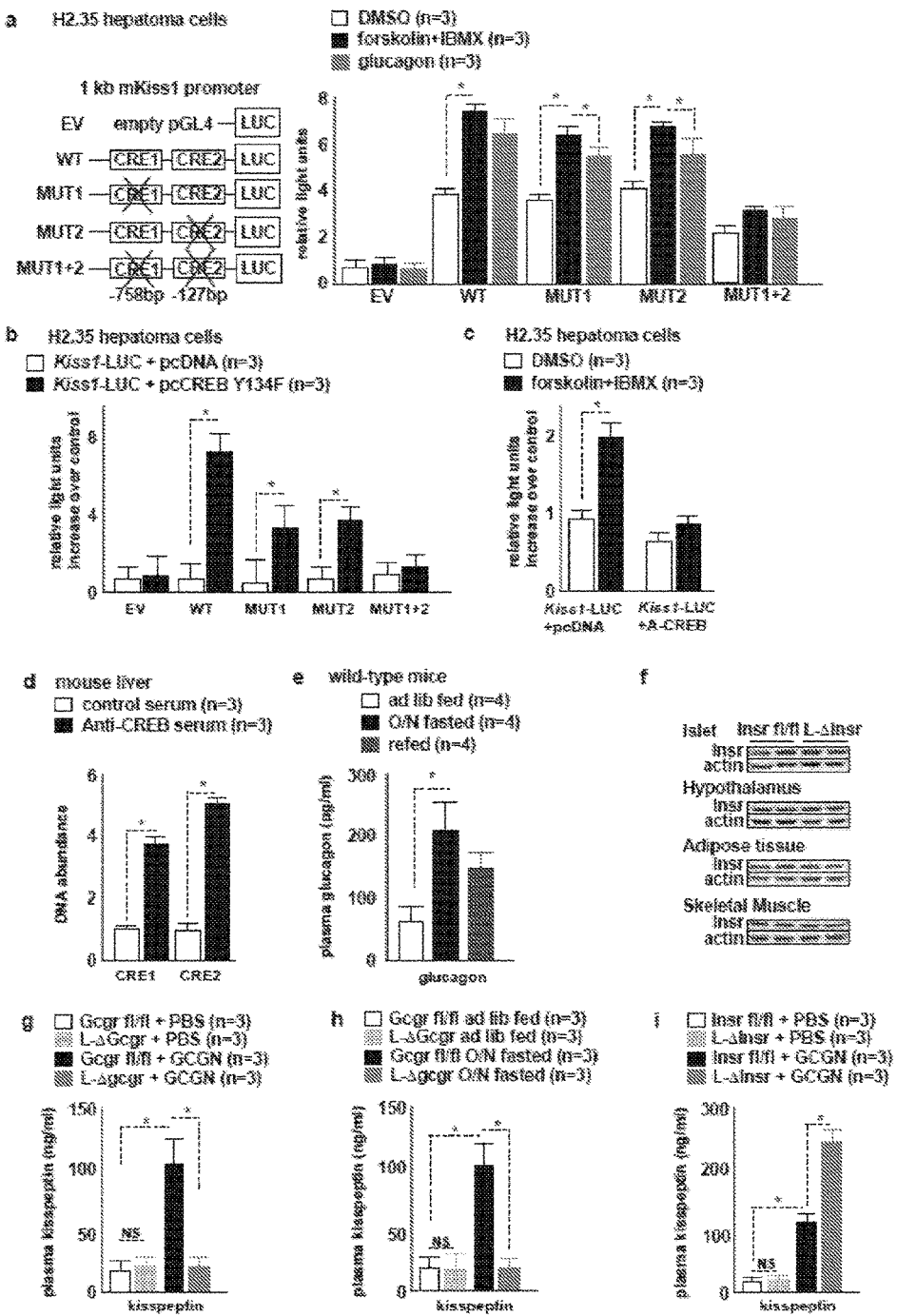

FIG. 9. Glucagon stimulates liver Kiss1 expression via cAMP-PKA-CREB signaling A (left) Schematic of luciferase reporter construct containing 1 kb of the murine Kiss1 promoter with mutations in CRE1, CRE2 or both CRE1 and 2 half sites. (right) Relative light units indicating luciferase activity after transient transfection into H2.35 hepatoma cells of Kiss1 promoter-luciferase reporter constructs followed by treatment with forskolin (fsk) and IBMX (100 μM each). Both CRE1 and CRE2 within the Kiss1 promoter functionally respond to frks/IBMX treatment. Mutation of both CRE1 and 2 abolishes response of Kiss1 promoter to fsk/IBMX stimulation (mean+SEM, * p<0.05). B Transient co-transfection in H2.35 hepatoma cells of Kiss1 promoter-luciferase reporter together with either empty pcDNA vector or constitutively active CREB Y134F. Both CRE1 and CRE2 within the Kiss1 promoter respond to activation by CREB Y134F. Mutation of both CRE1 and 2 abolishes response of Kiss1 promoter to CREB Y134F activation. (mean+SEM, * p<0.05). C Transient co-transfection in H2.35 hepatoma cells of Kiss1 promoter-luciferase reporter together with either empty pcDNA vector or dominant negative A-CREB. Stimulation with fsk/IBMX (100 μM each) of the Kiss1 promoter luciferase reporter is abolished by co-transfection of A-CREB (mean+SEM, *p<0.05). D Chromatin immunoprecipitation followed by qPCR to detect in vivo CREB occupancy on CRE1 and CRE2 half-sites within the Kiss1 promoter in liver samples of WT mice using control and CREB-specific antiserum. CREB occupies both CRE1 and CRE2 within the Kiss1 promoter (mean+SEM, * p<0.05). E Plasma glucagon levels in WT mice with unrestricted access to chow (ad lib fed), after an overnight fast (O/N fasted) and after regaining unrestricted access for 4 hours following an O/N fast. Plasma glucagon levels are elevated after O/N fasting and are reduced after 4 hours of refeeding (mean+SEM, * p<0.05). F Representative IB in islet, hypothalamus, adipose tissue and skeletal muscle in Insr fl/fl and L-ΔInsr mice. Adv-CRE treatment does not ablate Insr in these tissues (see also FIG. 2M). Actin IB is shown for protein loading control. G Plasma kisspeptin concentrations in Gcgrfl/fl and L-ΔGcgr mice after ip treatment with PBS or glucagon. Glucagon does not stimulate plasma kisspeptin in L-ΔGcgr mice (mean+SEM, * p<0.05). H Plasma kisspeptin concentrations in Gcgrfl/fl and L-ΔGcgr mice in fed and fasted states. Fasting does not stimulate plasma kisspeptin in L-ΔGcgr mice (mean+SEM, * p<0.05). I Plasma kisspeptin concentrations in Insrfl/fl and L-ΔInsr mice after ip treatment with PBS or glucagon. L-ΔInsr mice show a pronounced stimulation by glucagon in plasma kisspeptin (mean+SEM, * pp<0.05).

Figure 10:
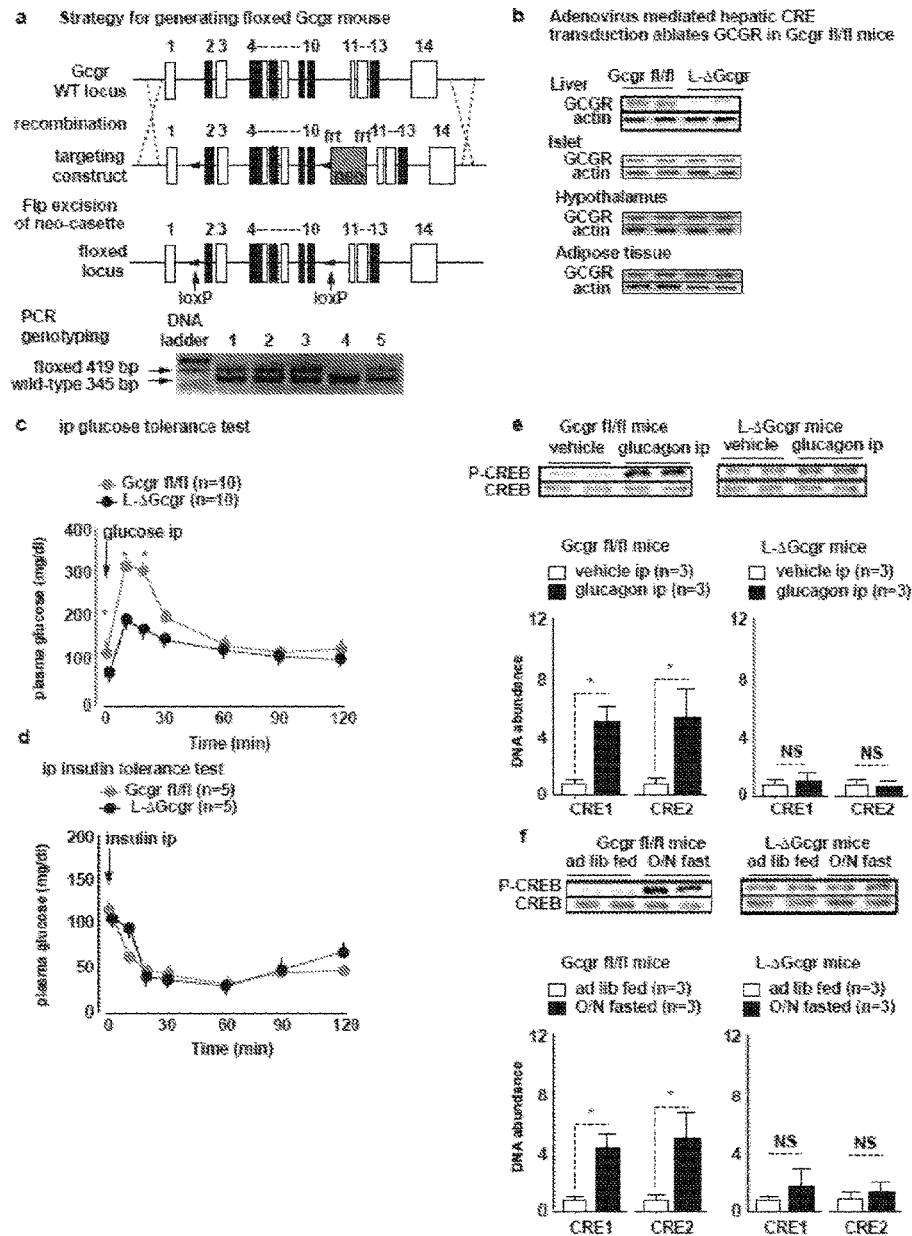

FIG. 10. Generation of Gcgrfl/fl mice using homologous recombination technology. Selective adenovirus-CRE recombinase mediated liver ablation of Gcgr results in improved glucose tolerance, reduced liver CREB phosphorylation in response to glucagon treatment or overnight fasting and defective increase in CREB occupancy on the Kiss1 promoter CREB response elements (CRE) 1 and 2. A (top) Schematic depicting Grgr WT locus, the targeting construct used for homologous recombination, the resulting floxed locus and (bottom) PCR genotyping for WT and floxed alleles. LoxP sites were inserted flanking exons 2 through 10. PCR genotyping differentiates WT and floxed alleles. B Representative IB for glucagon receptor (GCGR) in Gcgrfl/fl mice three days after treatment with Adv-GFP or Adv-CRE to ablate liver glucagon receptor expression (L-ΔGcgr mice). GCGR is efficiently ablated in vivo in liver tissue of L-ΔGcgr mice while GCGR remains detectable in control Gcgrfl/fl mice. Adv-CRE treatment does not ablate GCGR in islets, hypothalamus, adipose tissue. Actin IB is shown for loading control. C Plasma glucose levels during (top) ip GTT and (bottom) during ip ITT in Gcgrfl/fl and L-ΔGcgr mice. L-ΔGcgr mice exhibit improved glucose tolerance and similar insulin tolerance as compared to Gcgr fl/fl mice (mean+SEM). D (top) Representative liver IB showing pCREB and total CREB in liver 60 minutes after glucagon (100 μg/kg ip) treatment in Gcgr and L-ΔGcgr mice. CREB phosphorylation is stimulated in Gcgrfl/fl control mice, but is significantly reduced in mice lacking liver glucagon receptor (L-ΔGcgr mice); (bottom) Chromatin immunoprecipitation followed by qPCR to detect in vivo CREB occupancy on CRE1 and CRE2 half-sites within the Kiss1 promoter in liver 60 minutes after glucagon (100 μg/kg ip) treatment in Gcgr and L-ΔGcgr mice. CREB occupancy of CRE1 and CRE2 of the Kiss1 promoter increases after glucagon treatment in Gcgrfl/fl but not in L-ΔGcgr mice (mean+SEM, * p<0.05). E (top) Representative liver IB extracts showing pCREB and total CREB in liver of Gcgrfl/fl and L-ΔGcgr mice with unrestricted access to chow (ad lib fed) or after an overnight fast (O/N fasted). CREB phosphorylation is stimulated in Gcgrfl/fl control mice, but is significantly reduced in mice lacking liver glucagon receptor (L-ΔGcgr mice); (bottom) Chromatin immunoprecipitation followed by qPCR to detect in vivo CREB occupancy on CRE1 and CRE2 half-sites within the Kiss1 promoter in liver of Gcgrfl/fl and L-ΔGcgr mice with unrestricted access to chow (ad lib fed) or after an overnight fast (O/N fasted). CREB occupancy of CRE1 and CRE2 of the Kiss1 promoter increases after an overnight fast in Gcgrfl/fl but not in L-ΔGcgr mice (mean+SEM, * p<0.05).

Figure 11:
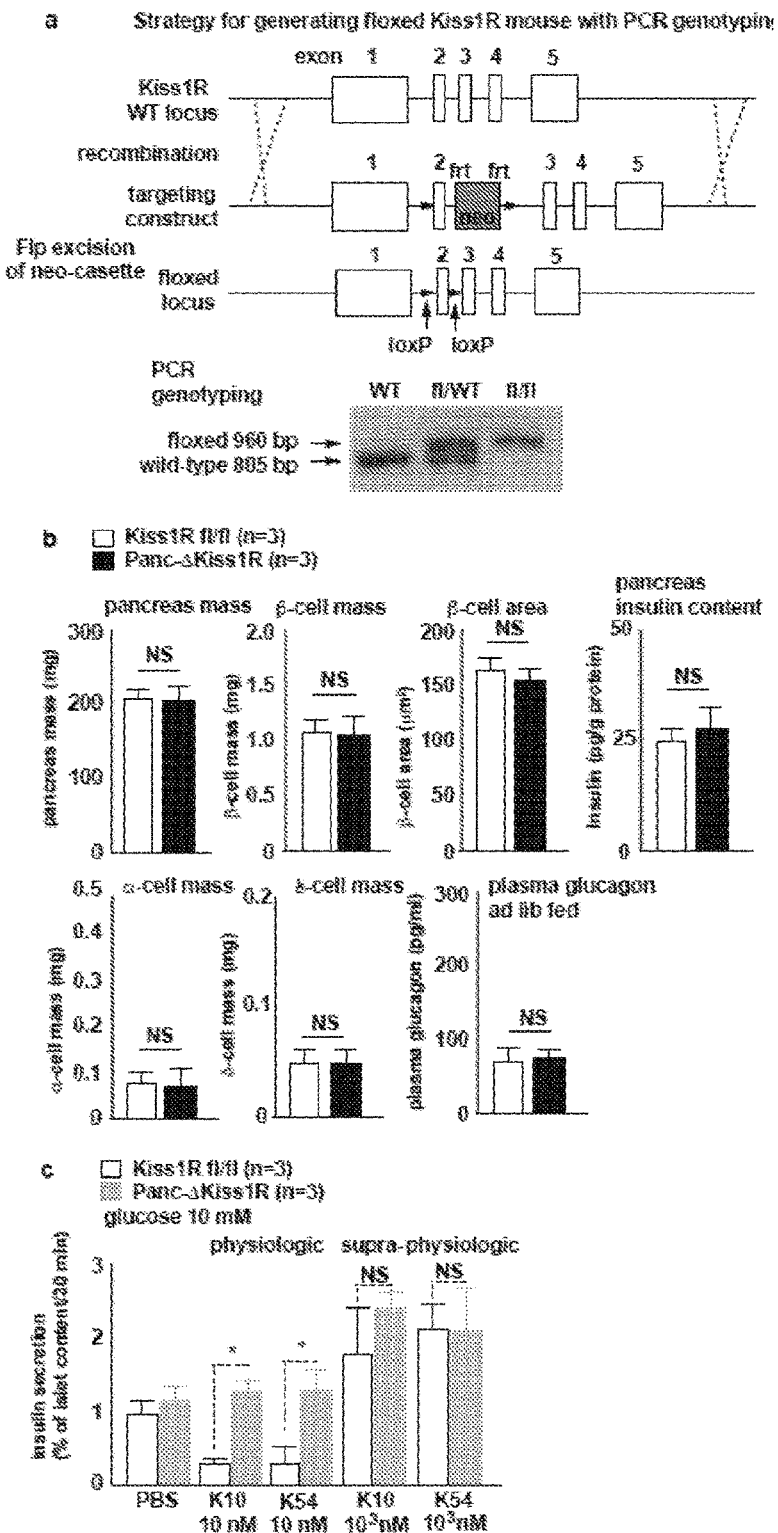

FIG. 11. Generation of Kiss1Rfl/fl mice using homologous recombination technology. Pancreas Kiss1R ablation does not affect pancreas morphometric parameters. Kisspeptin at nanomolar concentrations suppresses glucose stimulated insulin secretion from cultured islets in a Kiss1R-dependent manner. A (top) Schematic depicting Kiss1R WT locus, the targeting construct used for homologous recombination, the resulting floxed locus and (bottom) PCR genotyping for WT and floxed alleles. LoxP sites were inserted flanking exon 2. PCR genotyping differentiates WT and floxed alleles. B Panels show Pancreas mass, β-cell mass, individual β-cell area, pancreases insulin content, α-cell mass, δ-cell mass, and plasma glucagon levels in the fed state, respectively in Kiss1R fl/fl and in Panc-ΔKiss1R mice. Kiss1Rfl/fl and Panc-ΔKiss1R do not differ in pancreas morphometric parameters, insulin content or plasma glucagon levels (mean+SEM). C Glucose-stimulated insulin secretion during static incubation in 10 mM glucose of islets from Kiss1Rfl/fl and Panc-ΔKiss1R mice in response to vehicle (PBS) and to physiologic (10 nM) and supraphysiologic (103 nM) kisspeptin 10 (K10) concentrations (mean+SEM, * p<0.05). Physiologic K10 concentrations inhibit GSIS from Kiss1Rfl/fl and Panc-ΔKiss1R islets are resistant to K10 mediated GSIS suppression. At unusually high suprapysiologic K10 concentrations K10 stimulates GSIS in a Kiss1R-independent manner in both Kiss1Rfl/fl and Panc-ΔKiss1R islets.

Figure 12:
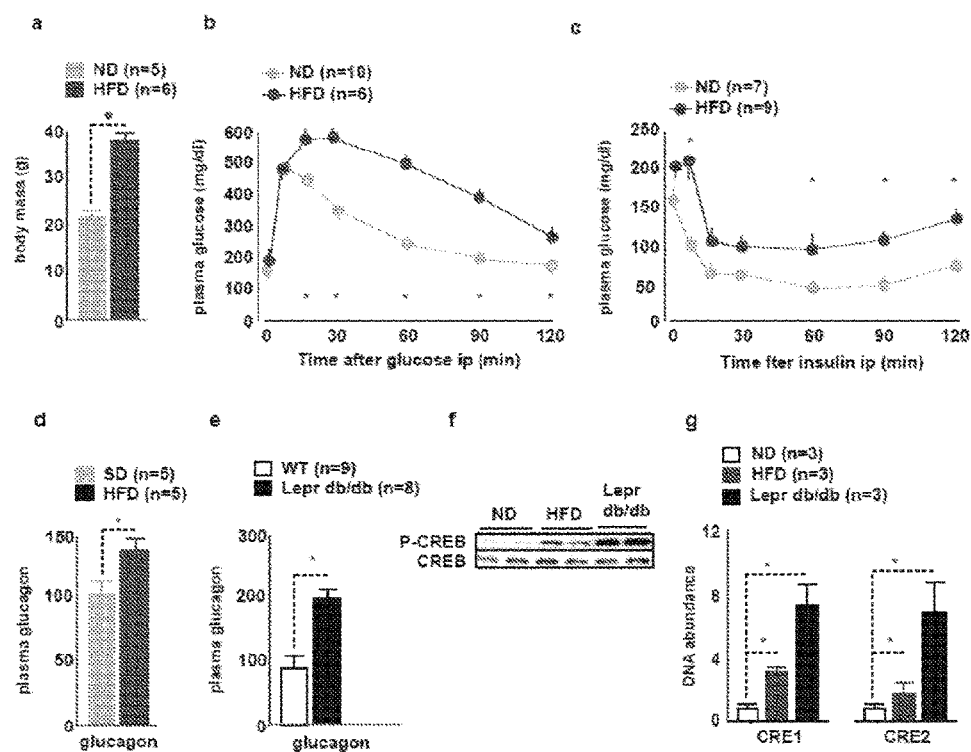

FIG. 12. High fat diet fed mice and $Lepr^{db/db}$ mice exhibit increased plasma glucagon levels, increased liver CREB phosphorylation and in vivo liver CREB occupancy of CRE1 and 2 within the Kiss1 promoter. A Body mass of male littermate mice after receiving for 8 weeks standard diet (SD) and high fat diet (HFD). HFD causes an increase in body weight (mean+SEM, * p<0.05). B Plasma glucose levels during (left) ip GTT and (right) during ip ITT in male mice after receiving for 8 weeks standard diet (SD) and high fat diet (HFD). HFD fed mice exhibit impaired glucose tolerance as well as reduced insulin tolerance (mean+SEM, * p<0.05). C Plasma glucagon levels in the fed state in male mice after receiving for 8 weeks standard diet (SD) and high fat diet (HFD). HFD fed mice exhibit elevated plasma glucagon levels as compared to mice kept on SD (mean+SEM, * p<0.05) D Plasma glucagon levels in the fed state in 3-4 week old male WT mice and in age matched male $^{db/db}$ mice. $Lepr^{db/db}$ mice exhibit elevated plasma glucagon levels as compared to WT mice (mean+SEM, * p<0.05). E Representative liver of pCREB and total CREB of WT mice kept on SD, in mice receiving 8 weeks of HFD and 3-4 week old male $Lepr^{db/db}$ mice. HFD fed mice and $Lepr^{db/db}$ mice show increased pCREB. Db/db mice show higher CREB phosphorylation status than HFD fed mice (mean+SEM). F Chromatin immunoprecipitation followed by qPCR to detect in vivo CREB occupancy on CRE1 and CRE2 half-sites within the Kiss1 promoter in liver samples of WT mice kept on SD, in mice receiving 8 weeks of HFD and 3-4 week old male $Lepr^{db/db}$ mice. HFD fed and $Lepr^{db/db}$ mice show increased CREB occupancy of both CRE1 and 2 half sites within the Kiss1 promoter (mean+SEM, * p<0.05).

Figure 13:
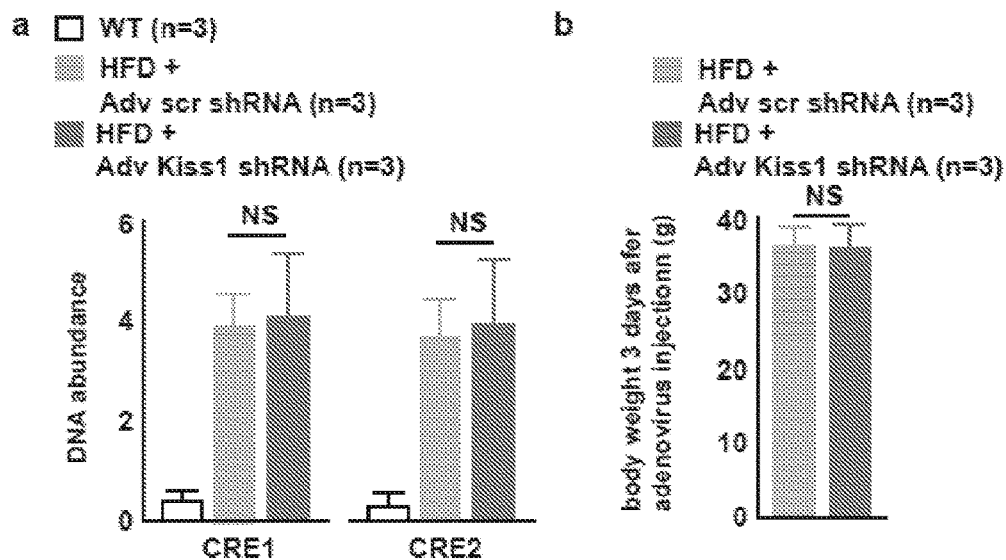
Figure 13:
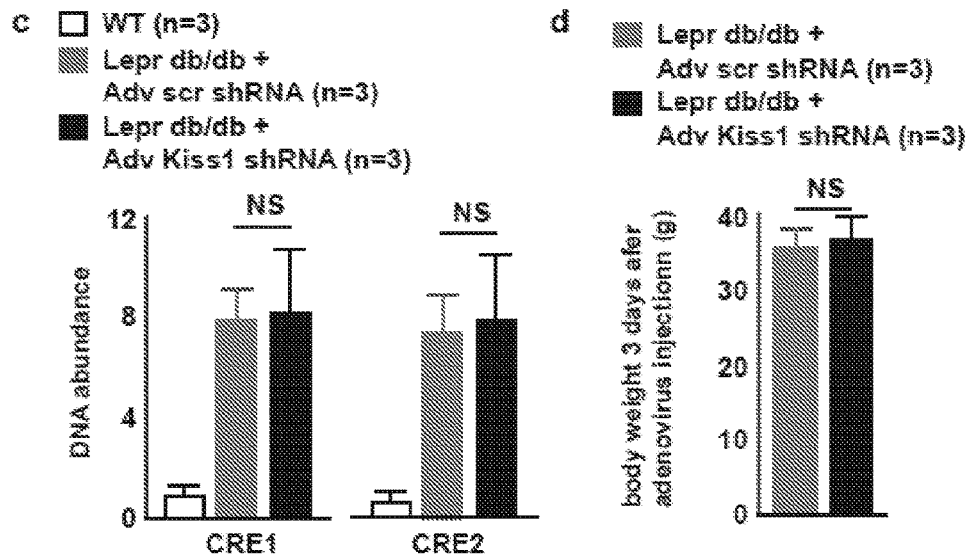

FIG. 13. In HFD fed and $Lepr^{db/db}$ mice shRNA-mediated Kiss1 knockdown does not alter in vivo CREB occupancy of CRE1 and 2 half-sites in Kiss1 promoter. shRNA-mediated Kiss1 knockdown as compared to scrambled shRNA treatment does not change body weight in HFD fed mice or $Lepr^{db/db}$ mice.

HFD fed mice. A Chromatin immunoprecipitation followed by qPCR to detect in vivo CREB occupancy on CRE1 and CRE2 half-sites within the Kiss1 promoter in liver samples from control mice kept on a standard diet (SD) and mice kept for 8 weeks on a HFD before treatment with Adv Kiss1-shRNA or control adenovirus scr-shRNA. Liver tissue was collected 3 days after adenovirus treatment. CREB occupancy on Kiss1 CRE half sites 1 and 2 in HFD fed mouse liver is increased as compared to liver from SD fed mice. Adenovirus mediated Kiss1 knockdown in HFD fed mice does not affect CREB occupancy of CRE 1 and 2 half-sites in the Kiss1 promoter (mean+SEM, * p<0.05). B Body weight in HFD fed mice 3 days after treatment with Adv-scr shRNA or Adv-Kiss1 shRNA. Body weight is similar in HFD fed mice and unaffected by Adv treatment (mean+SEM).

$Lepr^{db/db}$ mice. C Chromatin immunoprecipitation followed by qPCR to detect in vivo CREB occupancy on CRE1 and CRE2 half-sites within the Kiss1 promoter in liver samples from control WT and 4-5 week old $Lepr^{db/db}$ mice before treatment with Adv Kiss1-shRNA or control adenovirus scr-shRNA. Liver tissue was collected 3 days after adenovirus treatment. CREB occupancy on Kiss1 CRE half sites 1 and 2 in $Lepr^{db/db}$ mouse liver is increased as compared to liver from WT mice. Adenovirus mediated Kiss1 knockdown in $Lepr^{db/db}$ mice does not affect CREB occupancy of CRE 1 and 2 half-sites in the Kiss1 promoter (mean+SEM, * p<0.05). D Body weight in 4-5 week old $Lepr^{db/db}$ mice 3 days after treatment with Adv-scr shRNA or Adv-Kiss1 shRNA. Body weight is similar in L-Δprkar1a mice and unaffected by Adv treatment (mean+SEM).

Figure 14:
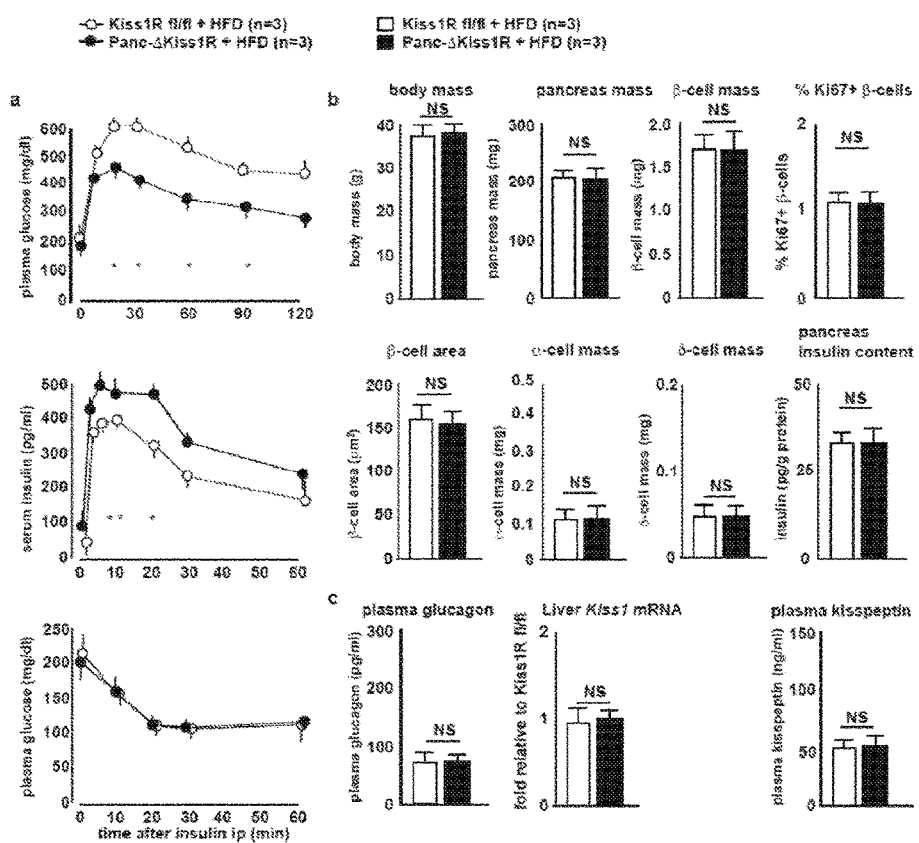

FIG. 14. High fat diet fed mice lacking pancreas Kiss1R have improved glucose tolerance owing to increased glucose stimulated insulin secretion. A (top) plasma glucose, (middle) serum insulin during ip GTT and (bottom) plasma glucose during ip ITT in 14 week old male Kiss1Rfl/fl mice and Panc-ΔKiss1R mice after receiving 8 weeks of HFD. Panc-ΔKiss1R mice have improved glucose tolerance as compared to Kiss1Rfl/fl counterparts. Insulin resistance as reflected by similar ITT is similar in Kiss1Rfl/fl and Panc-ΔKiss1R mice (mean+SEM). B Pancreas morphometry in 14 week old male Kiss1Rfl/fl mice and Panc-ΔKiss1R mice receiving after 8 weeks of HFD. Body mass, pancreas mass, β-cell mass and -size, % Ki67 positive β-cell reflecting β-cell proliferation activity, α-cell mass, δ-cell mass and pancreas insulin content are similar in Kiss1Rfl/fl mice and Panc-ΔKiss1R mice (mean+SEM). C Plasma glucagon, liver Kiss1 mRNA levels and plasma kisspeptin levels are similar in 14 week old male Kiss1Rfl/fl mice and Panc-ΔKiss1R mice receiving after 8 weeks of HFD (mean+SEM, * p<0.05).

Figure 15:
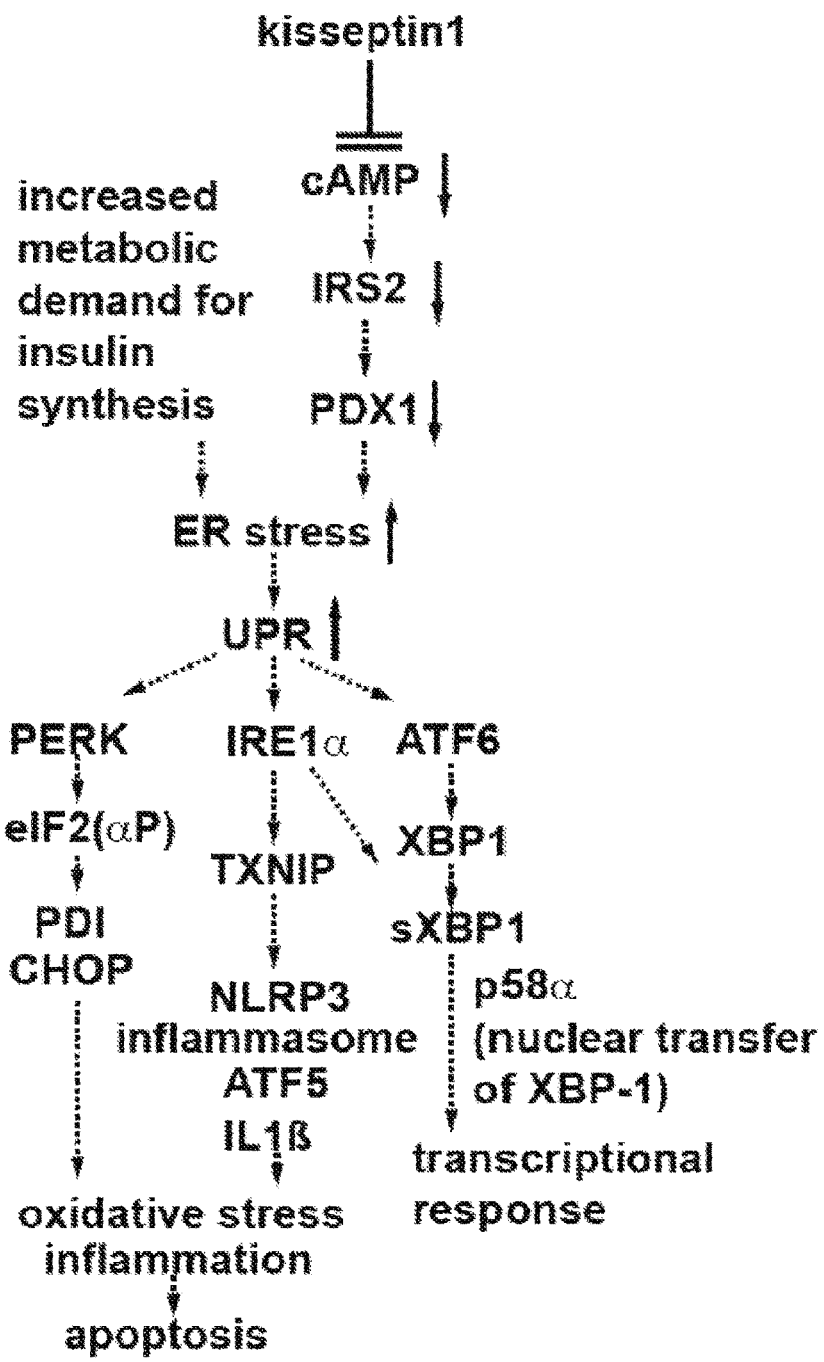

FIG. 15. Endoplasmic reticulum stress, unfolded protein response, β-cell dysfunction and -apoptosis.

Figure 16:
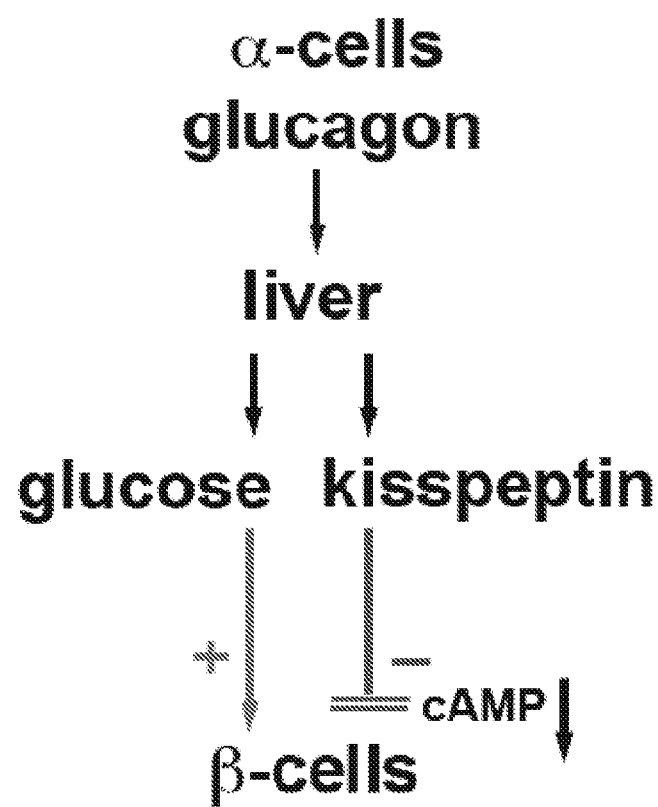

FIG. 16. Glucagon induced liver kisspeptin1 is linked to β-cell dysfunction, ER stress and UPR.

FIG. 17A-G. Experimental results utilizing floxed hepatic protein kinase A regulatory subunit 1A (prkar1a).

FIG. 18A-B. Mouse models of glucose intolerance and T2DM.

Figure 19:
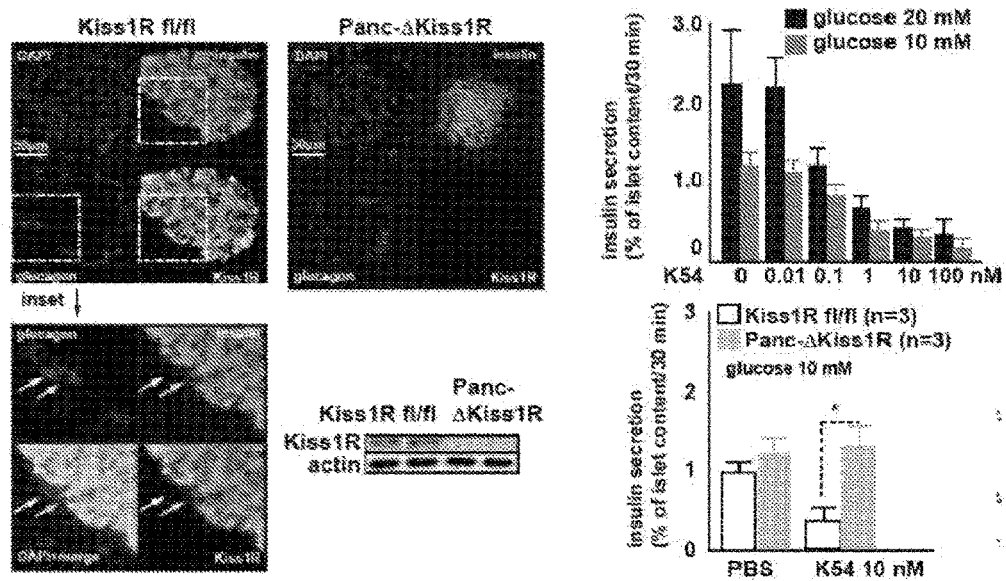

FIG. 19. Immunohistochemistry combined with confocal microscopy reveals kisspeptin receptor Kiss1R expression.

Figure 20:
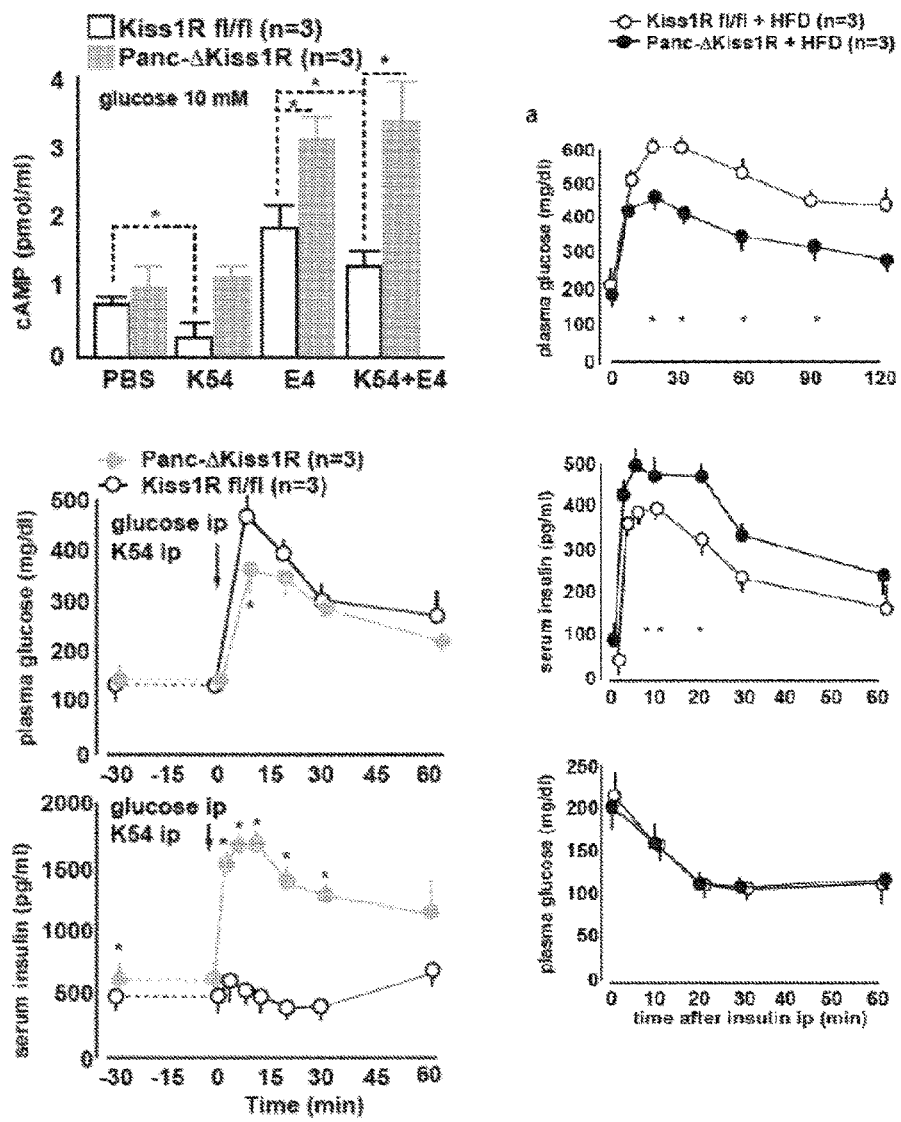

FIG. 20. Effects of Kiss1R agonist K54 on mouse islets and mice.

Figure 21:
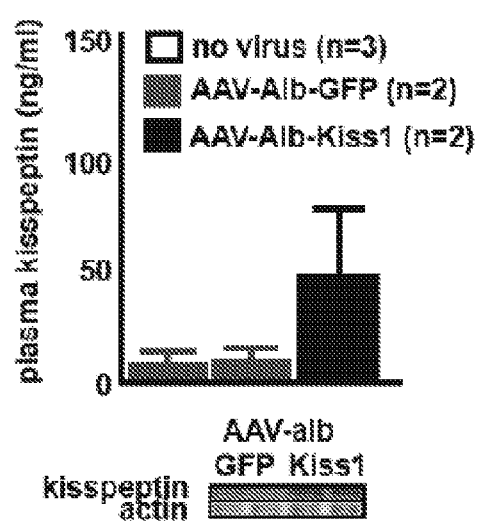

FIG. 21. In vivo model of isolated hepatic kisspeptin1 production. AAVA1b Kiss1 exhibit increased liver kisspeptin and plasma kisspeptin concentrations to a similar range found in DIO mice, whereas AAV-Alb-GFP treated mice did not show any change as compared to control mice without AAV treatment.

Figure 22:
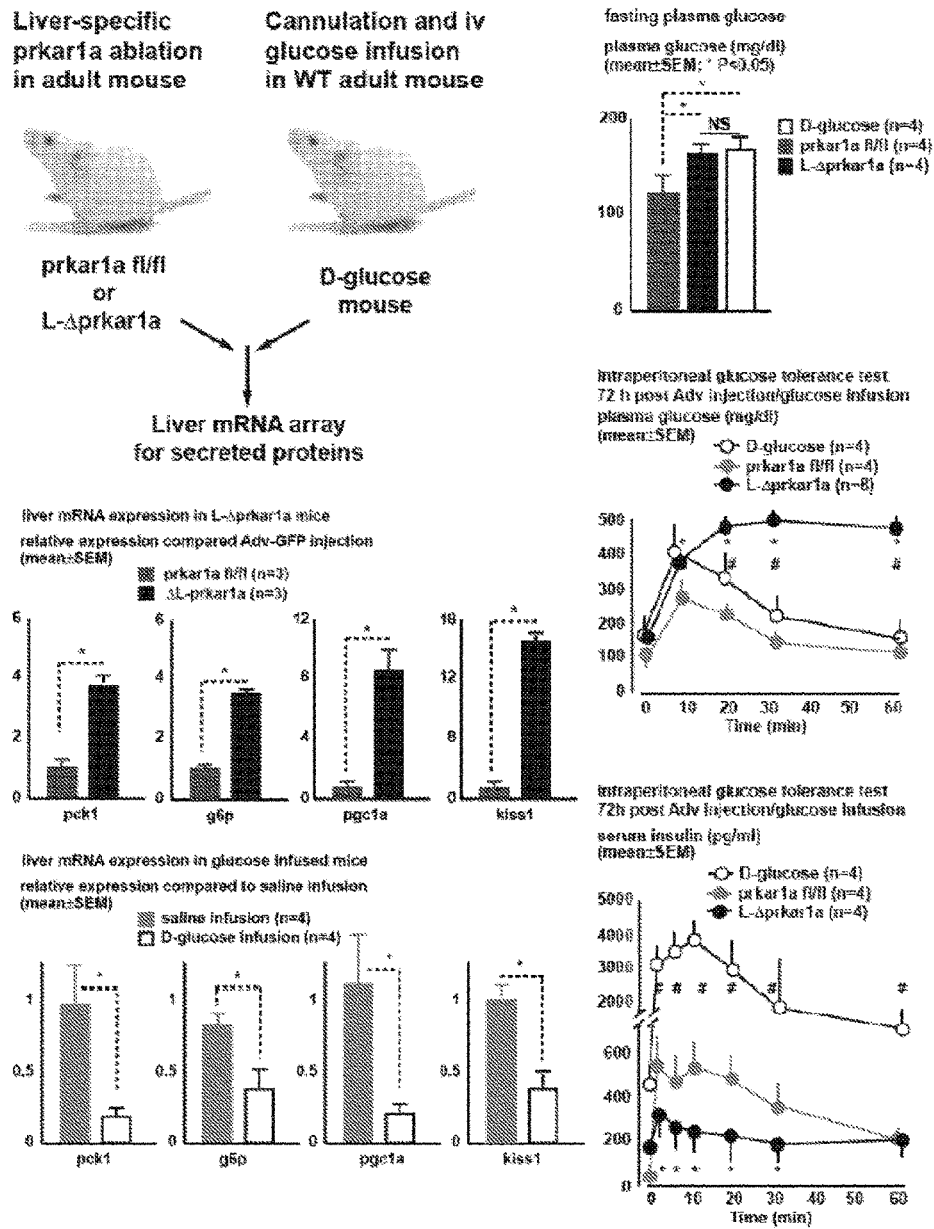

FIG. 22A-C. Top left: FIG. 22A; top right: FIG. 22B; bottom left: FIG. 22.C. Experimental results utilizing floxed hepatic protein kinase A regulatory subunit 1A (prkar1a).

Figure 23:
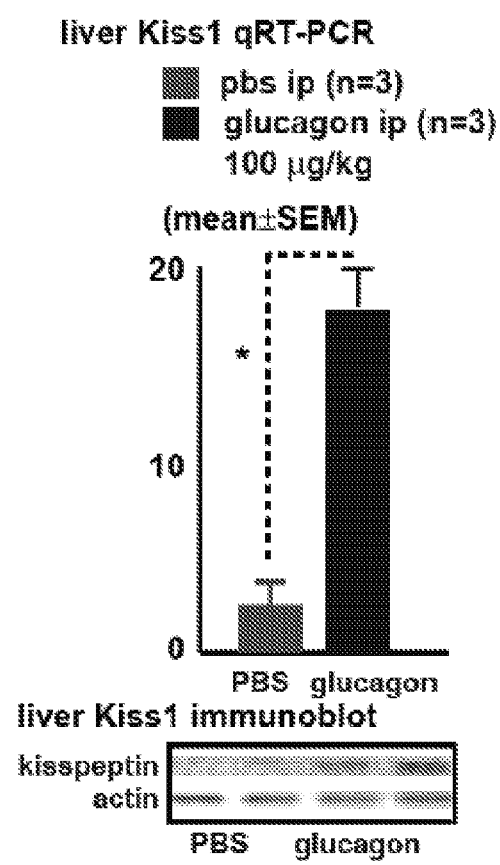

FIG. 23. Glucagon administration in normal mice increase hepatic Kiss1 expression.

Figure 24:
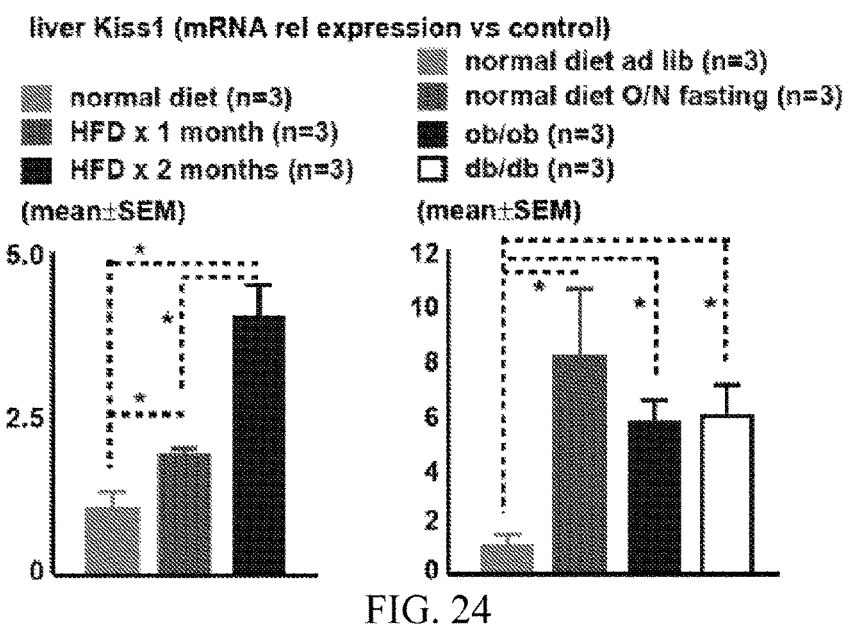

FIG. 24A (left panel)-B (right panel). Effect of diet and fasting of mice on Kiss1 expression.

Figure 25:
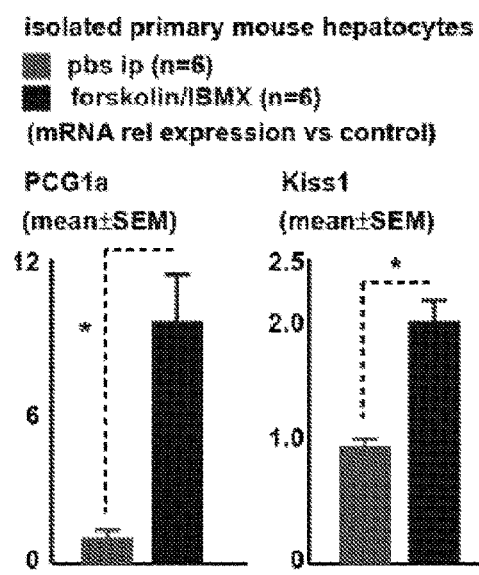

FIG. 25. Primary mouse hepatocytes treated with forskolin (100 μM)/IBMX (200 μM) to mimic glucagon cAMP-PKA signaling showed as expected increased Pgc1a and also increased Kiss1 expression.

Figure 26:
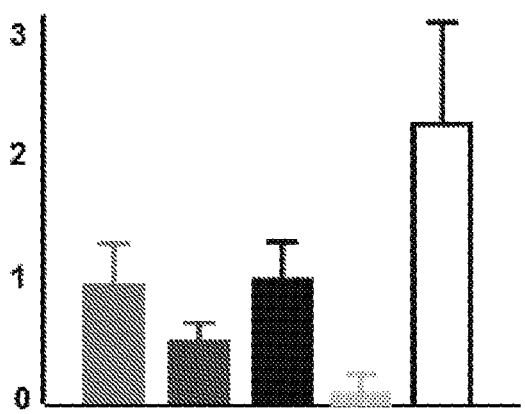

FIG. 26. GPR54 mRNA is high in liver, testes, kidney, skeletal muscle and islets.

Figure 27:
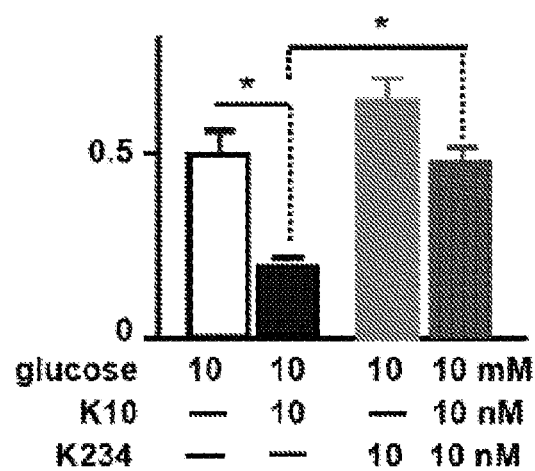

FIG. 27. K234 counteracts effects of k10.

Figure 28:
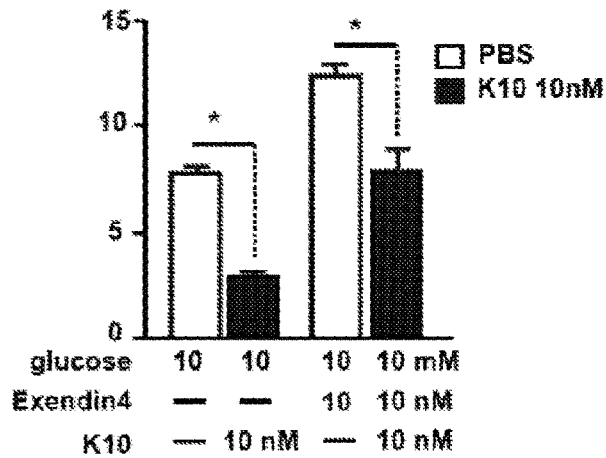

FIG. 28. K10 counteracts incretin Exendin4 (E4) effects.

Figure 29:
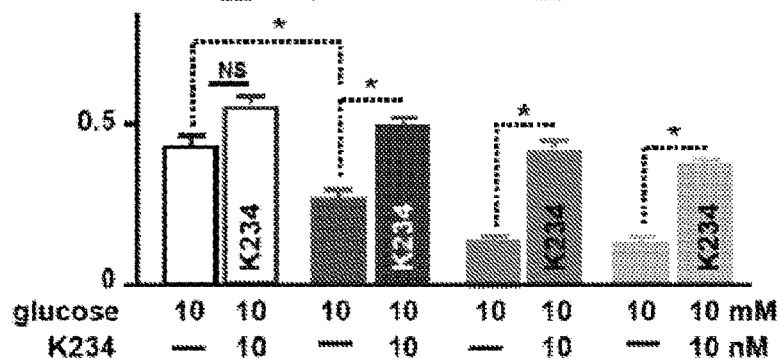

FIG. 29. K234 reverses effects of diabetic serum.

Figure 30:
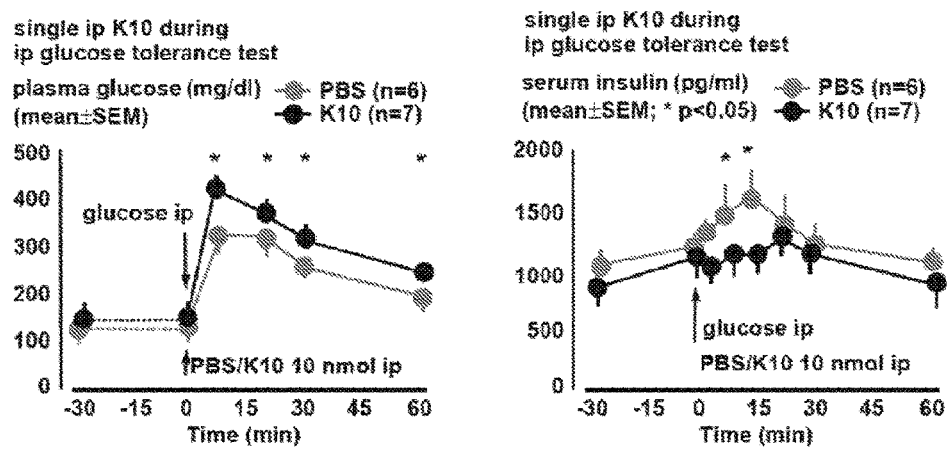

FIG. 30. K10 suppresses GSIS in vivo in WT mice.

Figure 31:
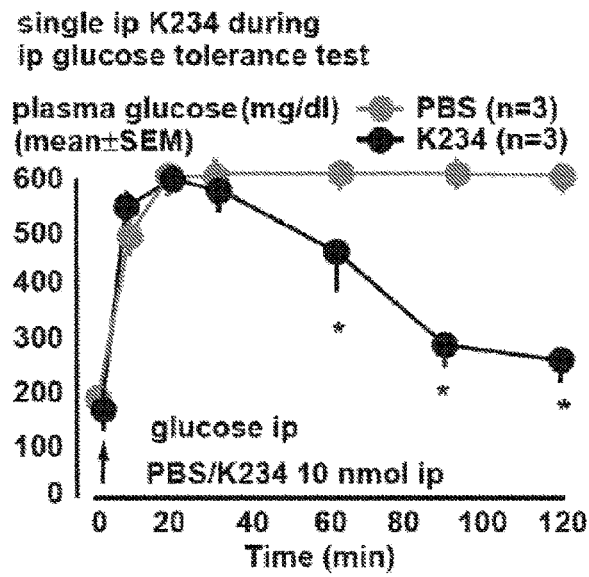

FIG. 31. K234 improves GTT in db/db mice.

Figure 32:
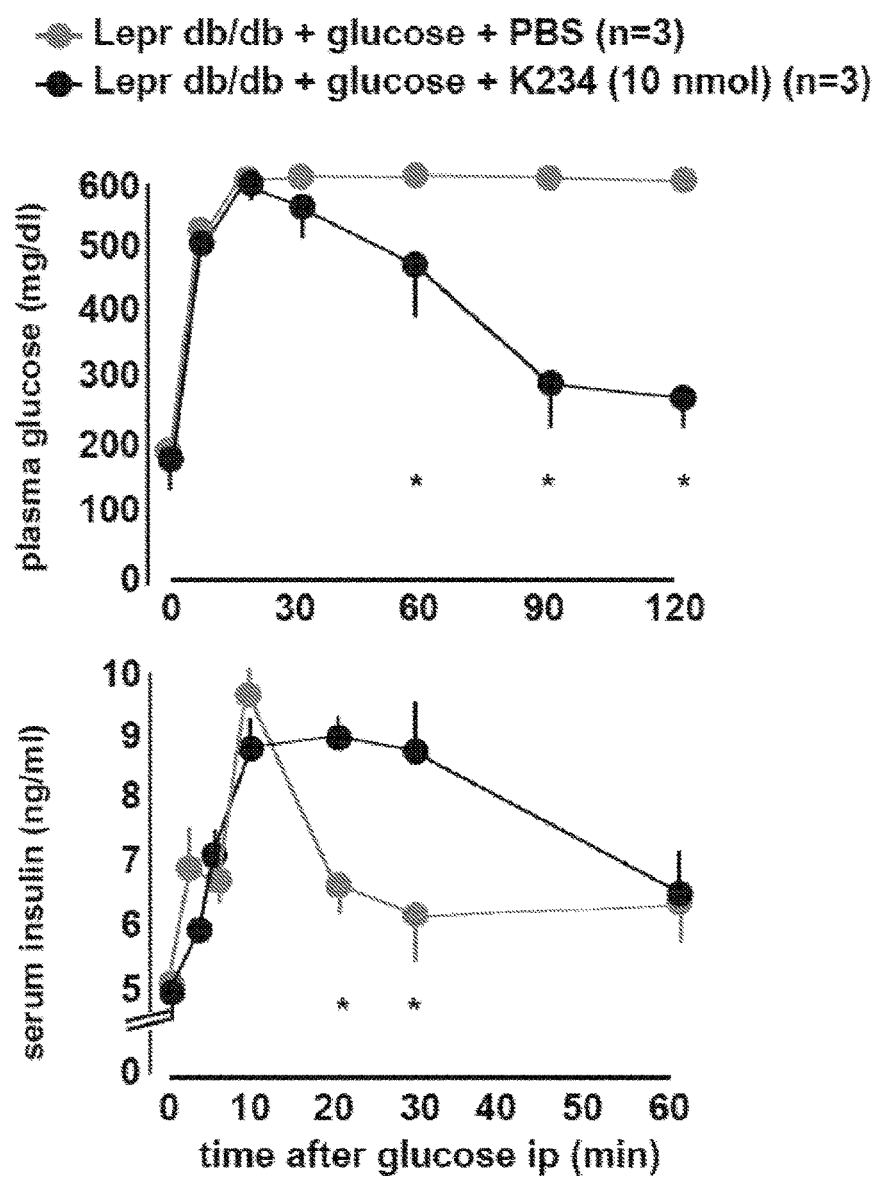
Figure 33:
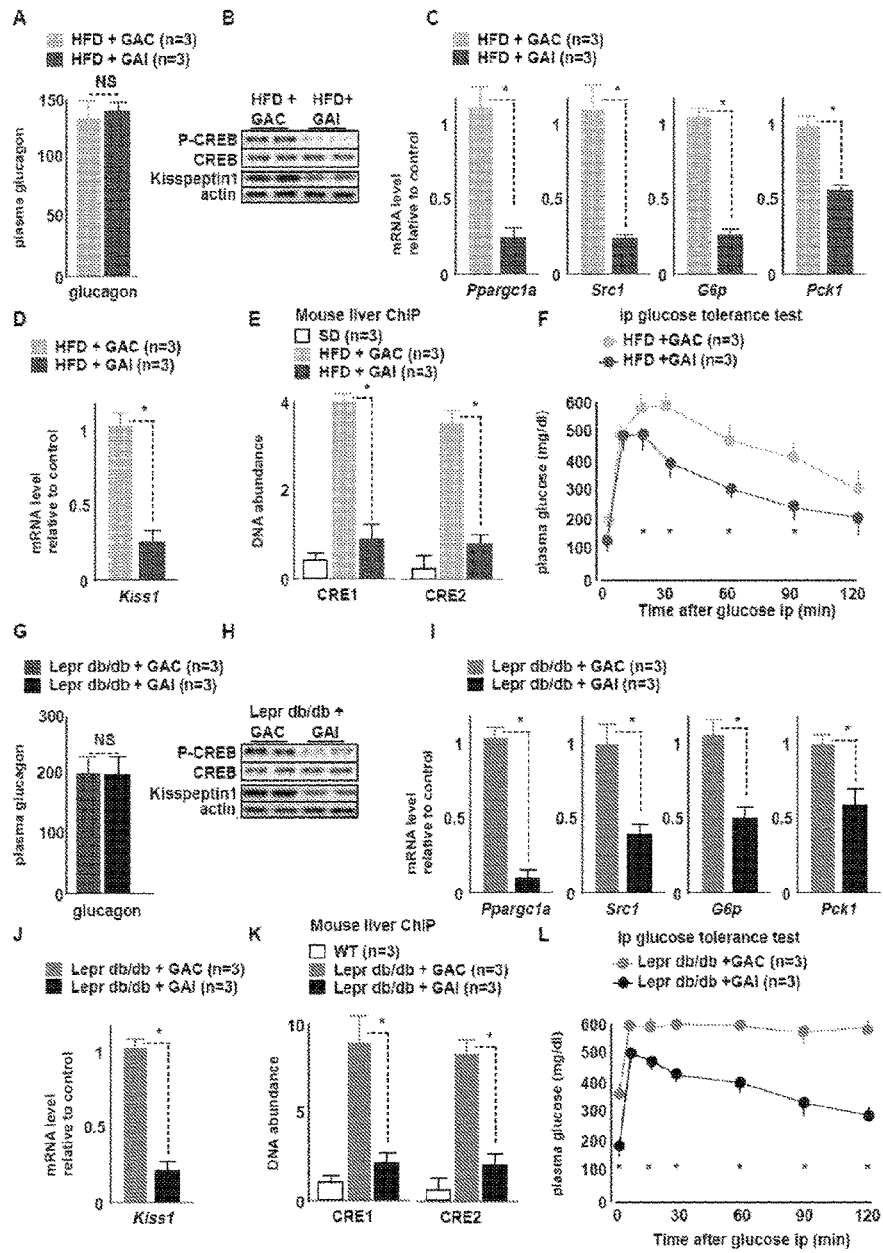

FIG. 32. Effect of Kisspeptin inhibitor K234 on plasma glucose and serum insulin levels.

FIG. 33A-L. Hyperlucagonemia Is Linked to Liver Kisspeptin1 Production in HFD Fed and $Lepr^{db/db}$ Mice (A-F) HFD-fed mice. (G-M) $Lepr^{db/db}$ mice. (A and G) Plasma glucagon levels in the fed state 60 min after treatment with GAI or GAC. Plasma glucagon levels remain unchanged after GAI or GAC treatment. (B and H) Representative liver IB for pCREB, total CREB and kisspeptin1 in GAI and GAC treated mice. Phospho-CREB is reduced in mice treated with GAI but not GAC. (C and I) qRT-PCR of indicated genes of the gluconeogenic program in livers of GAI- or GAC-treated mice. GAI but not GAC treatment downregulates Pparg1a, Src1, G6P, and Pck1 mRNA (mean±SEM; *p<0.05). (D and J) qRT-PCR of Kiss1 in livers of GAI- and GAC-treated mice. GAI but not GAC treatment downregulates liver Kiss1 mRNA (mean±SEM; *p<0.05). (E and K) In vivo ChIP of CREB occupancy on (left) CRE1 and (right) CRE2 half-sites of the Kiss1 promoter in livers of GAI- or GAC-treated SD mice, HFD and Leprdb/db mice. GAI reduces CREB occupancy on Kiss1 CRE1 and CRE2 to levels similar to those in control mice (mean±SEM; *p<0.05). (F and L) ipGTT in GAI- or GAC-treated mice. GAI treatment improves GT as compared to GAC treatment (mean±SEM; *p<0.05).

Figure 34:
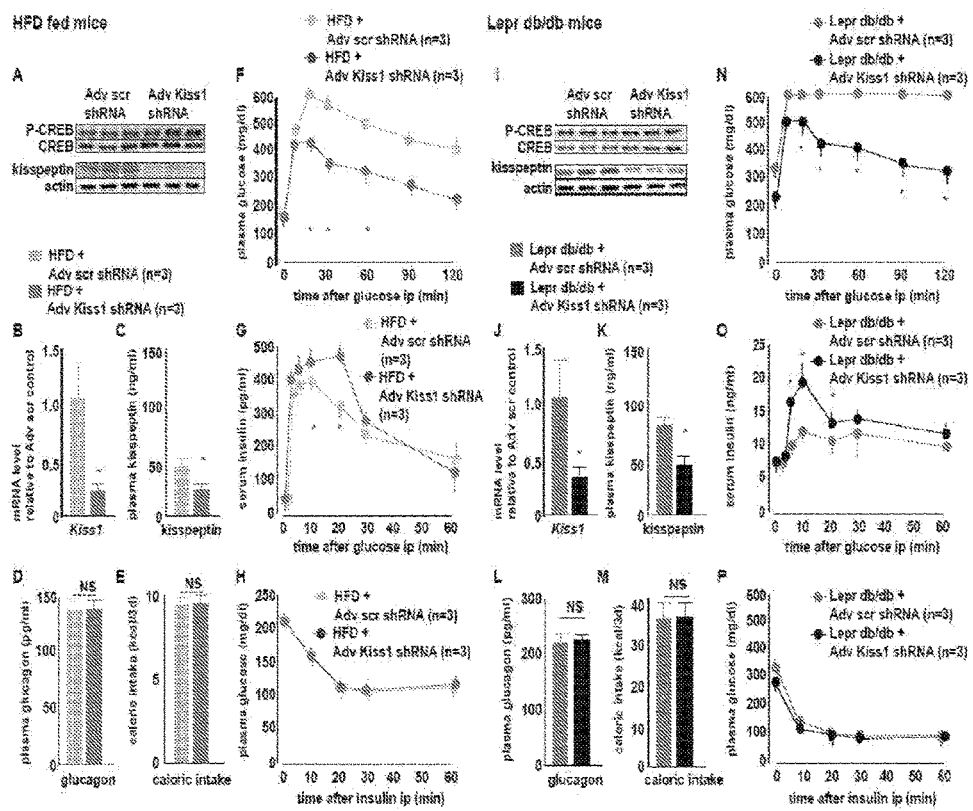

FIG. 34. Kiss1 shRNA Knockdown In Vivo in Livers of in HFD and $Lepr^{db/db}$ Mice Derepresses GSIS and Glucose Tolerance (A-H) HFD mice. (I-P) $Lepr^{db/db}$ mice. (A and I) Representative liver IB of pCREB, total CREB, and kisspeptin1 3 days after treatment with Adv-scr or Adv-Kiss1 shRNA. Liver pCREB is not affected, and liver kisspeptin1 protein is reduced by Kiss1 knockdown. (B and J) qRT-PCR of Kiss1 in livers 3 days after treatment with Adv-scr or Adv-Kiss1 shRNA. Adv-Kiss1 shRNA downregulates liver Kiss1 mRNA levels as compared to Adv-scr shRNA treatment (mean±SEM; *p<0.05). (C and K) Plasma kisspeptin1 levels 3 days after treatment with Adv-scr or Adv-Kiss1 shRNA. Liver Kiss1 knockdown reduces plasma kisspeptin1 (mean±SEM; *p<0.05). (D and L) Plasma glucagon levels 3 days after treatment with Adv-scr or Adv-Kiss1 shRNA. Liver Kiss1 knockdown does not change plasma glucagon levels (mean±SEM). (E and M) Caloric intake in during 3 days after treatment with Adv-scr or Adv-Kiss1 shRNA. Caloric intake is unaffected by Kiss1 knockdown (mean±SEM). (F and N) ipGTT 3 days after treatment with Adv-scr or Adv-Kiss1 shRNA. GT is improved after Kiss1 knockdown (mean±SEM; *p<0.05). (G and O) GSIS during ipGTT 3 days after treatment with Adv-scr or Adv-Kiss1 shRNA. GSIS is improved after Kiss1 knockdown (mean±SEM; *p<0.05). (H and P) i-p ITT 3 days after treatment with Adv-scr or Adv-Kiss1 shRNA. Insulin tolerance is not different after Kiss1 knockdown.

Figure 35:
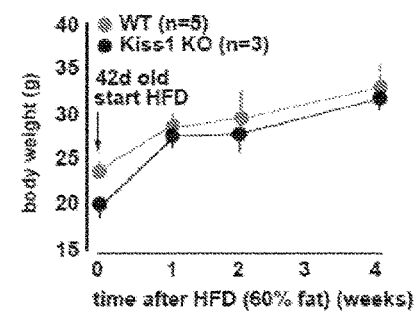
Figure 35:
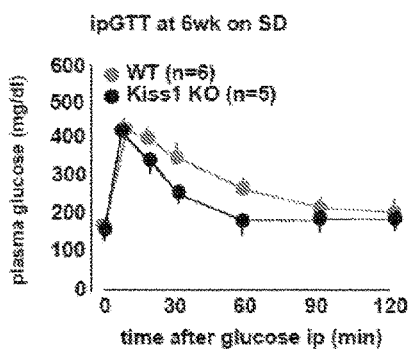
Figure 35:
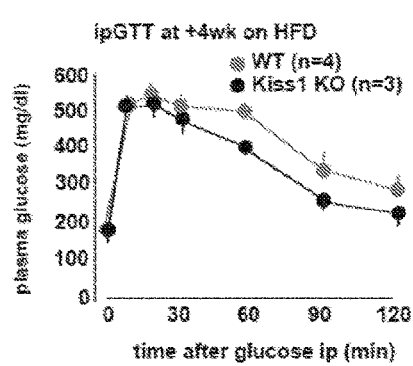
Figure 35:
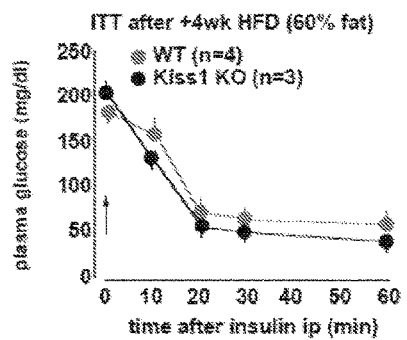

FIG. 35. Kiss-KO HFD2: Kiss-KO mice are resistant to high fat diet induced diabetes.

Figure 36:
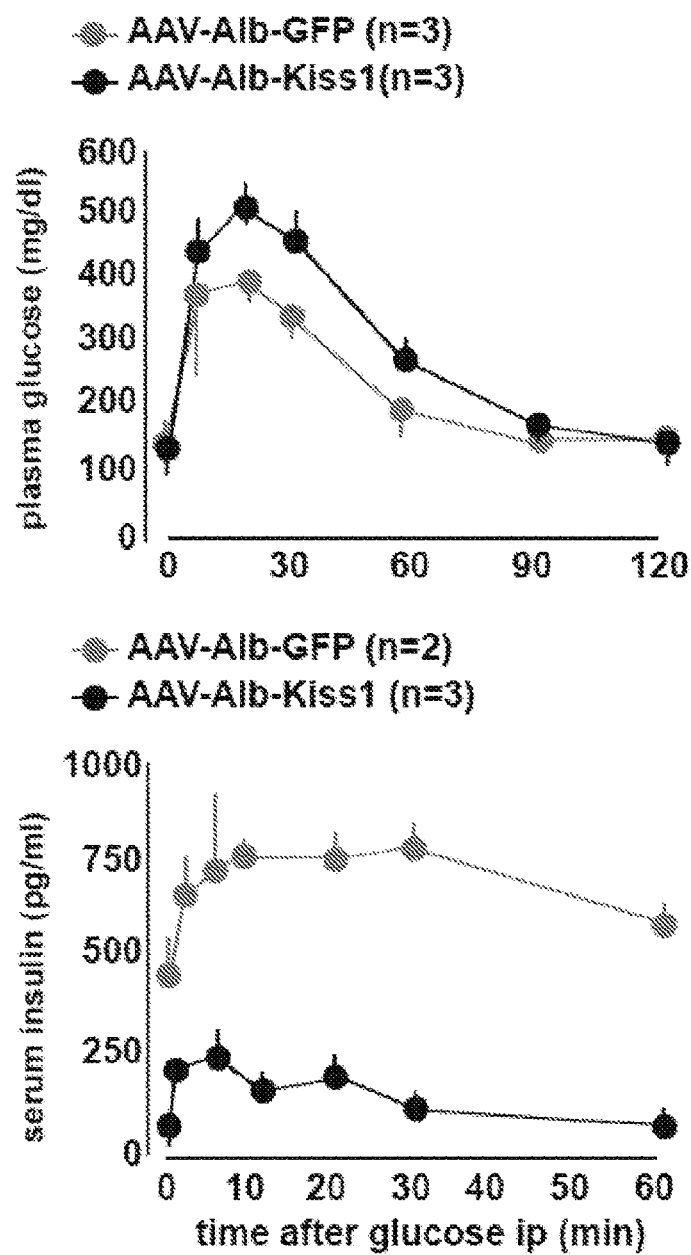

FIG. 36. AAV kiss1: AAV-Kiss1: Kisspeptin overexpression in the liver through adeno associated virus (Alb-Kiss1) induces glucose intolerance and suppresses insulin secretion.

Figure 37:
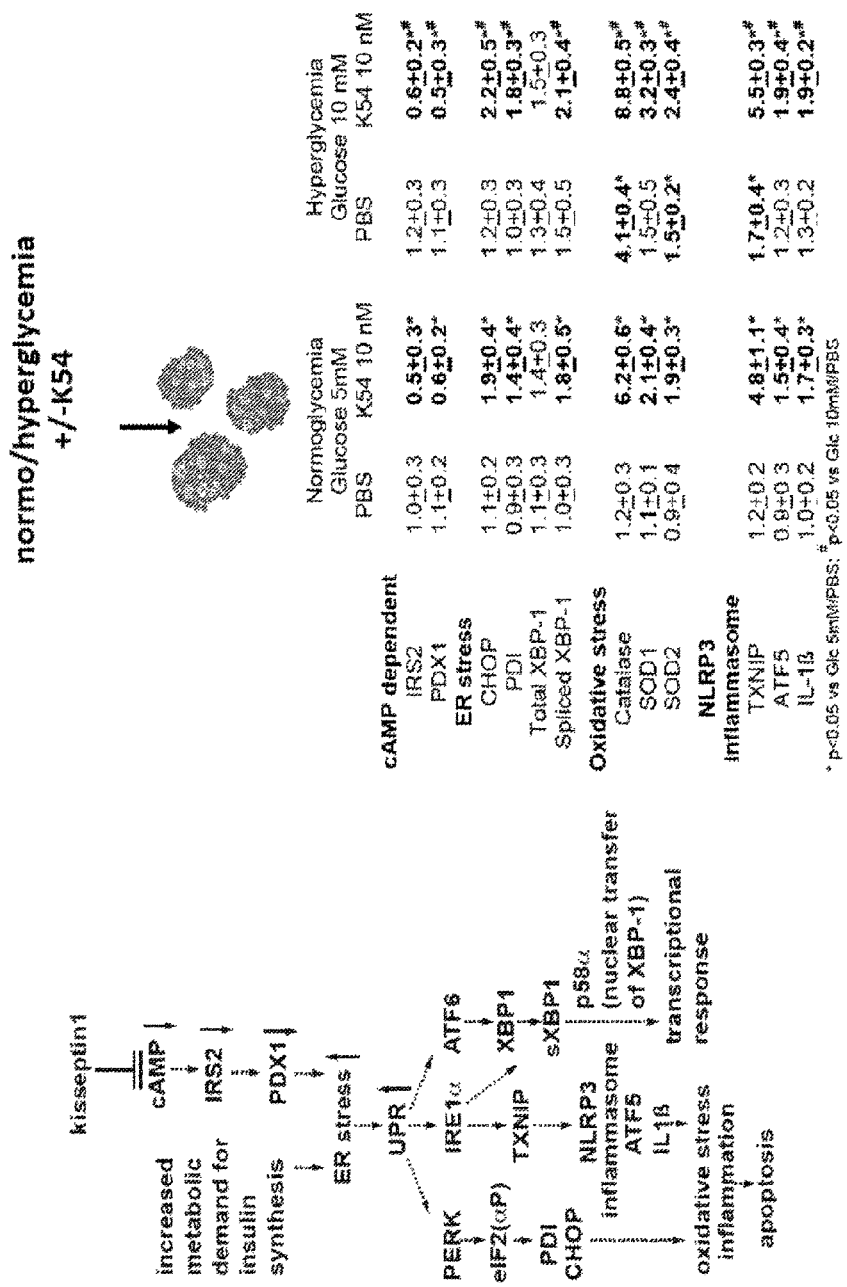

FIG. 37. Kiss54 incubation of islets: Kisspeptin induces ER stress and oxidative stress in islets.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Glucagon and insulin are secreted by pancreatic α and β cells, respectively, to precisely control blood glucose homeostasis. An early hallmark of type 2 diabetes mellitus (T2DM) is dysregulated glucagon secretion by pancreatic α cells. Nondiabetic humans exhibit postprandial suppression of blood glucagon, while individuals with T2DM lack this suppression and may even exhibit increased glucagon levels. In addition, studies in subsets of patients with T2DM suggest that elevated glucagon secretion occurs antecedent to β cell dysfunction (see D'Alessio [2011] and references therein).

Upon binding to its receptor Gcgr, glucagon activates cellular adenosine-30-50-cyclic monophosphate (cAMP)-protein kinase A (PKA) signaling to stimulate hepatic glucose production (HGP) and cause hyperglycemia (Chen et al., 2005). While hyperglycemia stimulates insulin secretion from β cells, transgenic upregulation of PKA activity in hepatocytes in mice results, as expected, in increased HGP and hyperglycemia but paradoxically in impaired GSIS (Niswender et al., 2005). Consistent with the idea that glucagon may be causally linked to β cell dysfunction are findings made during exogenous glucose infusion in rats, where insulin secretion only fails after blood glucagon levels rise and recovers upon glucagon inactivation by neutralizing antiserum (Jamison et al., 2011).

Based on these considerations for hyperglucagonemia and β cell dysfunction in T2DM, we reasoned that independent of HGP and hyperglycemia, glucagon signaling in the liver initiates a process that impacts on GSIS. We tested this hypothesis by comparing a mouse model of liver-specific PKA disinhibition (L-Δprkar1a mice, see below) with a model of hyperglycemia resulting from intravenous glucose infusion (D-glucose mice) combined with array-based gene expression analysis for secreted hepatic peptides, and we identified Kiss1, which encodes the neuropeptide kisspeptin1 to be upregulated in livers of L-Δprkar1a—but not in D-glucose-mice and to be directly stimulated by glucagon action via Gcgr on hepatocytes.

Kisspeptin1 has been described to be synthesized in the central nervous system and to regulate hypothalamic gonadotropin releasing hormone (GnRH) neurons and is processed to multiple biologically active, N-terminally truncated fragments, including kisspeptin 54 (K54), K14, K13, and K10, of which the latter exerts full biological effects (Seminara and Kaiser, 2005).

Immunometric assays for kisspeptin have provided conflicting information on kisspeptin levels in rodents and humans (Akinci et al., 2012; Cetkovic et al., 2012; Horikoshi et al., 2003; Logie et al., 2012), and mass-spectroscopy-based assays do not provide exact information on circulating concentrations and functional bioactivity of the complement of kisspeptin isoforms in biological samples (Liu et al., 2013). Therefore, we have used—in addition to immunoassays—a bioassay of kisspeptin1 action on GSIS from mouse islets, which either express Kiss1R or selectively lack Kiss1R to reliably measure functional kisspeptin concentrations.

Using this assay, we find that synthetic kisspeptin inhibits GSIS from cultured islets in a dose- and Kiss1R-dependent manner at nanomolar concentrations. Furthermore, mice rendered glucose intolerant by high-fat-content diet (HFD) or leptin receptor defective diabetic (Lepr$^{db/db}$) mice are hyperglucagonemic, exhibit increased liver kisspeptin1, and harbor in their circulation functional kisspeptin bioactivity equivalent to nanomolar concentrations of synthetic kisspeptin. In these mice, selective liver kisseptin1 knockdown derepresses GSIS and improves glucose tolerance (GT). Importantly, humans with T2DM also exhibit increased liver and plasma kisspeptin1 levels. Furthermore, mice selectively lacking pancreas Kiss1R, when fed a HFD, as compared to control counterparts, show improved GT owing to increased GSIS.

These observations identify the liver as a site of regulated kisspeptin1 synthesis, define a liver-to-islet endocrine circuit in glucoregulation, and suggest a pathogenic mechanism in T2DM, causally linking hyperglucagonemia via hepatic kisspeptin1 to insufficient insulin secretion. In addition, these findings extend a potential for kisspeptin1 antagonism as a therapeutic means to improve β cell function in diabetes mellitus.

I. Definitions

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term "about."

An "agonist" is a type of modulator and refers to an agent that binds a target and can activate one or more functions of the target. For example, an agonist of a protein can bind the protein and activate the protein in the absence of its natural or cognate ligand.

As used herein, an "antagonist" is a type of modulator and is used interchangeably with the term "inhibitor." In certain non-limiting embodiments, the term refers to an agent that binds a target (e.g., a protein) and can inhibit a one or more functions of the target. For example, an antagonist of an enzymatic protein can bind the protein and inhibit the enzymatic activity of the protein.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies. In specific embodiments, antibodies may be raised against Kisspeptin and/or GPR54 and used as Kisspeptin/GPR54 antagonists.

As used herein, the term "effective," means adequate to accomplish a desired, expected, or intended result. More particularly, a "therapeutically effective amount" as provided herein refers to an amount of a Kisspeptin/GPR54 modulator of the present invention, either alone or in combination with another therapeutic agent, necessary to provide the desired therapeutic effect, e.g., an amount that is effective to prevent, alleviate, or ameliorate symptoms of disease or prolong the survival of the subject being treated. In a specific embodiment, the term "therapeutically effective amount" as provided herein refers to an amount of a Kisspeptin/GPR54 modulator, necessary to provide the desired therapeutic effect, e.g., an amount that is effective to prevent, alleviate, or ameliorate symptoms of disease or prolong the survival of the subject being treated. In a particular embodiment, the disease or condition is diabetes. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The term "inhibitor" is a type of modulator and is used interchangeably with the term "antagonist." The term "inhibitor" includes any type of molecule or agent that directly or indirectly inhibits the expression or activity of a target gene or protein. An inhibitor can be any type of compound, such as a small molecule, antibody or antisense compound. In certain embodiments, the target gene or protein is Kisspeptin and/or GPR54. The term also includes agents that have activity in addition to Kisspeptin/GPR54 inhibitory activity.

As used herein, the term "modulate" indicates the ability to control or influence directly or indirectly, and by way of non-limiting examples, can alternatively mean inhibit or stimulate, agonize or antagonize, hinder or promote, and strengthen or weaken. Thus, the term "Kisspeptin/GPR54 modulator" refers to an agent that modulates the expressions and/or activity of Kisspeptin and/or GPR54. Modulators may be organic or inorganic, small to large molecular weight individual compounds, mixtures and combinatorial libraries of inhibitors, agonists, antagonists, and biopolymers such as peptides, nucleic acids, or oligonucleotides. A modulator may be a natural product or a naturally-occurring small molecule organic compound. In particular, a modulator may be a carbohydrate; monosaccharide; oligosaccharide; polysaccharide; amino acid; peptide; oligopeptide; polypeptide; protein; receptor; nucleic acid; nucleoside; nucleotide; oligonucleotide; polynucleotide including DNA and DNA fragments, RNA and RNA fragments and the like; lipid; retinoid; steroid; glycopeptides; glycoprotein; proteoglycan and the like; and synthetic analogues or derivatives thereof, including peptidomimetics, small molecule organic compounds and the like, and mixtures thereof. A modulator identified according to the invention is preferably useful in the treatment of a disease disclosed herein.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

"Optional" or "optionally" means that the subsequently described event or circumstance can or cannot occur, and that the description includes instances where the event or circumstance occurs and instances where it does not.

The terms "patient," "individual," or "subject" are used interchangeably herein, and refer to a mammal, particularly, a human. The patient may have a mild, intermediate or severe disease or condition. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates. In particular, the term also includes mammals diagnosed with a Kisspeptin/GPR54 mediated disease, disorder or condition.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules. In addition, as used herein, the term "polypeptide" refers to amino acids joined to each other by peptide bonds or modified peptide bonds, e.g., peptide isosteres, etc., and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristoylation, oxidation, pergylation, proteolytic processing, phosphorylation, prenylation, racemization, selenoylation, sulfation, and transfer-RNA mediated addition of amino acids to protein such as arginylation. See Proteins— Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983).

The terms "specifically binds to," "specific for," and related grammatical variants refer to that binding which occurs between such paired species as antibody/antigen, enzyme/substrate, receptor/agonist, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/ substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$M to $10^{-9}$ M, $10^{-10}$ M, $10^{-11}$ M, or $10^{-12}$ M.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In a specific embodiment, the disease or condition is diabetes.

II. Antagonists of Kisspeptin/GPR54

The present invention relates to the treatment of diabetes using antagonists of Kisspeptin and/or GPR54, or otherwise the inhibition of the ligand/receptor relationship of Kisspeptin and GPR54. In certain embodiments, the Kisspeptin/GPR54 antagonist is selected from the group consisting of a small molecule, a polypeptide, a nucleic acid molecule, a peptidomimetic, or a combination thereof. In a specific embodiment, the agent can be a polypeptide. In a more specific embodiment, the antagonist polypeptide can be a Kisspeptin polypeptide. In another embodiment, the polypeptide can be an antibody. In another embodiment, the agent can be a nucleic acid molecule. The nucleic acid molecule can, for example, be a Kisspeptin/GPR54 inhibitory nucleic acid molecule. The Kisspeptin/GPR54 inhibitory nucleic acid molecule can comprise a short hairpin or interfering RNA (shRNA or siRNA) molecule, a microRNA (miRNA) molecule, or an antisense molecule.

A. Kisspeptin Antagonist Peptides

Studies to date have focused primarily on kisspeptin actions in the hypothalamus and the pituitary, respectively, in regulating gonadotropin releasing hormone (GnRH) production and secretion as well as gonadotropin (luteinizing hormone (LH) and follicle stimulating hormone (FSH) release. Kiss1R is expressed in hypothalamic GnRH neurons and in gonadotrophs of the anterior pituitary gland. Kisspeptin-Kiss1R signaling plays a critical role in regulating the hypothalamic-pituitary-gonadal axis. Mutations in kisspeptin or Kiss1R are associated with reduced or absent gonadotropin production and delayed or absent puberty and infertility in humans as well as in mouse models.

Kisspeptin is encoded by the Kiss1 gene located on the long arm of chromosome 1 in both mouse and humans. The Kiss1 gene products in mouse (126 amino acids (aa) and humans (138 aa) share only approx. 52% sequence homology. Kisspeptin is further processed to the biologically active N-terminally truncated 54 amino-acid (aa) amidated protein kisspeptin 54 (K54, also known as metastin). However kisspeptin is further cleaved to 14, 13, and 10 aa N-terminally truncated fragments. The 10 carboxy-terminal aa of kisspeptin (K10) are necessary for binding to and activating the only known kisspeptin receptor KISS1R30; and the K10 sequence is highly conserved between human and mouse, varies only by one conserved amino acid [Tyr to Phe] and exerts the full biological effects of kisspeptin. The nucleotide and amino acid sequences of kisspeptin are known in the art and readily available. The present invention contemplates the use of peptide inhibitors/antagonists of kisspeptin and its derivatives including K54, K14, K13, and K10, including K234 (see SEQ ID NOS:36-37) and others described in U.S. Pat. No. 8,916,681 and U.S. Pat. No. 8,716,228. See also Roseweir et al., 784 ADVANCES IN EXP.MED. & BIOL. 159-86 (2013); Roseweir et al., 29 J. NEUROSCI. 3920-29 (2009). Miller et al., 1364 BRAIN RES. 81-9 (2010); Pineda et al., 151(2) ENDOCRIN. 722-30 (2010).

The kisspeptin receptor Kiss1R (=KISS1R, AXOR12, hOT7T175) consists of 5 exons and encodes a 395 aa protein in the mouse. KISS1R shares 82% homology between humans and mouse. Kiss1R belongs to the class A/1 of G-protein coupled receptor and is similar in sequence and structure to the galanin and ghrelin receptors. Both galanin and ghrelin receptors are expressed on pancreatic β-cells where their activation suppresses cyclic AMP (cAMP) synthesis and suppresses GSIS. This is a particular property of the ghrelin and galanin receptors on β-cells, where their binding with inhibitory G-proteins inhibits cAMP synthesis, while in other tissues, the same receptors signal through the Gq/11 pathway to stimulate intracellular calcium levels. To this end it is important to note that incretin hormones and incretin analogs (e.g. exendin-4) potentiate GSIS mainly via stimulating β-cell cAMP synthesis14. The present invention contemplates the use of GPR54/Kiss1R peptide antagonists including, but not limited to, the kisspeptin antagonists mentioned above, as well as GPR54 polypeptides (as a competitive inhibitor).

In certain embodiments, peptide sequences of the antagonist molecules of the present invention can be synthesized by the Fmoc-polyamide mode of solid-phase peptide synthesis. See Lu et al (1981) J. Org. Chem. 46, 3433. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used can be the acid-labile 4-hydroxymethyl-phenoxyacetic acid derivative. All amino acid derivatives can be added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesized. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

In other embodiments, the peptide sequence of the antagonist molecules of the present invention can be synthesized using liquid phase methodology, which is well known those skilled in the art of chemistry and biochemistry.

In further embodiments, the peptide sequence of the antagonist molecules may comprise or consist of peptidomimetic compounds. The term "peptidomimetic" refers to a compound that mimics the conformation and desirable features of a particular peptide as a therapeutic agent, but that avoids the undesirable features. For example, morphine is a compound which can be orally administered, and which is a peptidomimetic of the peptides enkephalin and/or endorphin.

In general, therapeutic applications involving peptides are limited due to lack of oral bioavailability and to proteolytic degradation, and are typically administered by injection. Typically, for example, peptides are rapidly degraded in vivo by exo- and endopeptidases, resulting in generally very short biological half-lives. Another deficiency of peptides as potential therapeutic agents is their lack of bioavailability via oral administration. Degradation of the peptides by proteolytic enzymes in the gastrointestinal tract is likely to be an important contributing factor. The problem is, however, more complicated because it has been recognized that even small, cyclic peptides or peptides comprising D-amino acids which are not subject to rapid metabolite inactivation nevertheless exhibit poor oral bioavailability. This is likely to be due to poor transport across the intestinal membrane and rapid clearance from the blood by hepatic extraction and subsequent excretion into the intestine. These observations suggest that multiple amide bonds may interfere with oral bioavailability. It is thought that the peptide bonds linking the amino acid residues in the peptide chain may break apart or be cleaved when the peptide drug is orally administered.

Accordingly, there are a number of different approaches to the design and synthesis of peptidomimetics. In one approach, such as disclosed by Sherman and Spatola, J. Am. Chem. Soc., 112: 433 (1990), one or more amide bonds can be replaced in an essentially isoteric manner by a variety of chemical functional groups. This stepwise approach has met with some success in that active analogues have been obtained. In some instances, these analogues have been shown to possess longer biological half-lives than their naturally-occurring counterparts. When replacing the peptide bond it is preferred that the new linker moiety has substantially the same charge distribution and substantially the same planarity as a peptide bond.

Retro-inverso peptidomimetics, in which the peptide bonds are reversed, can be synthesized by methods known in the art, for example such as those described in Mezi re et al (1997) J. Immunol. 159 3230-3237. This approach involves making pseudopeptides containing changes involving the backbone, and not the orientation of side chains. Retro-inverse peptides, which contain NH—CO bonds instead of CO—NH peptide bonds, are much more resistant to proteolysis. Retro-inverso peptidomimetics of certain GnRH peptides have been synthesized previously (Fromme, 2003, Endocrinology, 144:3262-9).

In another approach, a variety of un-coded or modified amino acids such as D-amino acids and N-methyl amino acids have been used to modify mammalian peptides. Alternatively, a presumed bioactive conformation has been stabilized by a covalent modification, such as cyclisation or by incorporation of .gamma.-lactam or other types of bridges. See, for example, Veber et al, Proc. Natl. Acad. Sci. USA, 75:2636 (1978) and Thursell et al, Biochem. Biophys. Res. Comm., 111:166 (1983).

In certain embodiments, a common theme among many of the synthetic strategies has been the introduction of some cyclic moiety into a peptide-based framework. The cyclic moiety restricts the conformational space of the peptide structure and this frequently results in an increased affinity of the peptide for a particular biological receptor. An added advantage of this strategy is that the introduction of a cyclic moiety into a peptide may also result in the peptide having a diminished sensitivity to cellular peptidases.

One approach to the synthesis of cyclic stabilized peptidomimetics is ring closing metathesis (RCM). This method involves steps of synthesizing a peptide precursor and contacting it with a RCM catalyst to yield a conformationally-restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in Protease Inhibitors, Barrett and Selveson, eds., Elsevier (1986), has been to design peptide mimics through the application of the transition state analogue concept in enzyme inhibitor design. For example, it is known that the secondary alcohol of staline mimics the tetrahedral transition state of the scissile amide bond of the pepsin substrate. However, the transition state analogue concept has no apparent relevance to hormone agonist/antagonist design.

In particular embodiments, it is not necessary that the amino acid residues in the peptide sequence are joined by standard peptide bonds. For example, as discussed above, the amino acid residues may be linked by reverse peptide bonds, or they may be joined together by other bonds which mimic the bond distance and spatial orientation of a standard peptide bond.

Peptide sequences of the agents of the invention may be purified following synthesis using methods known in the art, such as HPLC and chromatography.

The term "molecule" includes salts (e.g., organic or inorganic acid addition salts), esters and solvates of the molecules comprising or consisting of the antagonist peptide sequences. It will be appreciated that the term further includes derivatives that have the same biological function and/or activity as the relevant molecule. Moreover, for the purposes of this invention, the term also includes prodrugs of the relevant molecule (for example, esters). The term "prodrug" includes any composition of matter that, following oral or parenteral administration, is metabolized in vivo to form the relevant agent in an experimentally-detectable amount, and within a predetermined time of dosing.

The molecules of the invention may further consist of or comprise one or more moiety which is capable of targeting and/or localizing the molecule of the invention to a target cell and/or to increase the half-life (t½) of the molecule of the invention. Such moieties can therefore increase efficacy of the molecule of the invention. In some embodiments, one or more moiety may be included in a molecule of the invention when the molecule comprises or consists of a peptide sequence comprising or consisting of a D-amino acid as those amino acid residues are particularly amenable to modification.

In certain embodiments, the one or more moiety is a steroid hormone molecule (including, for example, progesterone, testosterone, estradiol or cortisol) and is conjugated to the side chain of a D-amino acid. Steroid hormone molecules are capable of binding to plasma proteins and have been shown to reduce the metabolic clearance of peptides (Ratcliffe et al., 2006, Endocrinology, 147:571-9).

For example, GnRH peptides conjugated to steroid hormones are described in WO2004/08725, incorporated herein by reference. Alternatively, the one or more moiety is a vitamin, such as vitamin B12 or vitamin D, and is conjugated to the NH2 terminus of the kisspeptin analogues or a suitable side chain of a natural or D-amino acid. Vitamins have been shown to improve the oral bioavailability of peptides (Russell-Jones et al., 1995, Bioconjug. Chem., 6:34-42; Russell-Jones et al., 1995, Bioconjug. Chem., 6:459-465).

In particular embodiments, the ability of the molecule of the invention to act as an antagonist of kisspeptin is not affected and/or significantly affected by the one or more moiety.

B. Antibodies to Kisspeptin and/or GPR54

In certain embodiments, the antagonist can be an antibody that binds Kisspeptin. In other embodiments, the antagonist can be an antibody that binds GPR54. The term antibody is used herein in a broad sense and includes both polyclonal and monoclonal antibodies. The term can also refer to a human antibody and/or a humanized antibody. Examples of techniques for human monoclonal antibody production include those described by Cole et al. (Monoclonal Antibodies and Cancer Therapy, Alan R. Liss, p. 77 (1985)) and by Boerner et al. (J. Immunol. 147(1):86-95 (1991)). Human antibodies (and fragments thereof) can also be produced using phage display libraries (Hoogenboom et al., J. Mol. Biol. 227:381 (1991); Marks et al., J. Mol. Biol. 222:581 (1991)). The disclosed human antibodies can also be obtained from transgenic animals. For example, transgenic mutant mice that are capable of producing a full repertoire of human antibodies, in response to immunization, have been described (see, e.g., Jakobovits et al., Proc. Natl. Acad. Sci. USA 90:2551-5 (1993); Jakobovits et al., Nature 362: 255-8 (1993); Bruggermann et al., Year in Immunol. 7:33 (1993)).

Various procedures known in the art may be used for the production of antibodies to Kisspeptin/GPR54, or a fragment, derivative, homolog or analog of the protein. Antibodies of the present invention include, but are not limited to, synthetic antibodies, polyclonal antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv) (including bi-specific scFvs), single chain antibodies Fab fragments, F(ab') fragments, disulfide-linked Fvs (sdFv), and anti-idiotypic (anti-Id) antibodies, and epitope-binding fragments of any of the above. In particular, antibodies of the present invention include immunoglobulin molecules and immunologically active portions of immunoglobulin molecules, e.g., molecules that contain an antigen binding site that immunospecifically binds to an antigen (e.g., one or more complementarity determining regions (CDRs) of an antibody).

Another embodiment for the preparation of antibodies according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics in rational design is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting antibodies disclosed herein, but with altered and even improved characteristics. More specifically, under this rational design approach, peptide mapping may be used to determine "active" antigen recognition residues, and along with molecular modeling and molecular dynamics trajectory analysis, peptide mimic of the antibodies containing antigen contact residues from multiple CDRs may be prepared.

In some embodiments, an antibody specifically binds an epitope of the Kisspeptin/GPR54 protein. It is to be understood that the peptide regions may not necessarily precisely map one epitope, but may also contain a Kisspeptin/GPR54 sequence that is not immunogenic. Methods of predicting other potential epitopes to which an immunoglobulin of the invention can bind are well-known to those of skill in the art and include, without limitation, Kyte-Doolittle Analysis (Kyte, J. and Dolittle, R. F., 157 J. MOL. BIOL. 105-32 (1982)); Hopp and Woods Analysis (Hopp, T. P. and Woods, K. R., 78 PROC. NATL. ACAD. SCI. USA 3824-28 (1981); Hopp, T. J. and Woods, K. R., 20 MOL. IMMUNOL. 483-89 (1983); Hopp, T. J., 88 J. IMMUNOL. METHODS 1-18 (1986)); Jameson-Wolf Analysis (Jameson, B. A. and Wolf, H., 4 COMPUT. APPL. BIOSCI. 181-86 (1988)); and Emini Analysis (Emini et al., 140 VIROLOGY 13-20 (1985)).

Amino acid sequence variants of the antibodies of the present invention may be prepared by introducing appropriate nucleotide changes into the polynucleotide that encodes the antibody or by peptide synthesis. Such modifications include, for example, deletions from, and/or insertions into and/or substitutions of, residues within the amino acid sequences of the antibody. Any combination of deletions, insertions, and substitutions may be made to arrive at the final construct.

Amino acid sequence insertions include amino-terminal and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of a polypeptide that increases the serum half-life of the antibody.

Another type of antibody variant is an amino acid substitution variant. These variants have at least one amino acid residue in the antibody molecule replaced by a different residue. For example, the sites of greatest interest for substitutional mutagenesis of antibodies include the hypervariable regions, but framework region (FR) alterations are also contemplated.

A useful method for the identification of certain residues or regions of the Kisspeptin/GPR54 antibodies that are preferred locations for substitution, i.e., mutagenesis, is alanine scanning mutagenesis. See Cunningham & Wells, 244 SCIENCE 1081-85 (1989). Briefly, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. The amino acid locations demonstrating functional sensitivity to the substitutions are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis may be conducted at the target codon or region and the expressed antibody variants screened for the desired activity.

Substantial modifications in the biological properties of the antibody can be accomplished by selecting substitutions that differ significantly in their effect on, maintaining (i) the structure of the polypeptide backbone in the area of the substitution, for example, as a sheet or helical conformation, (ii) the charge or hydrophobicity of the molecule at the target site, or (iii) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Conservative substitutions involve exchanging of amino acids within the same class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability, particularly where the antibody is an immunoglobulin fragment such as an Fv fragment.

Another type of substitutional variant involves substituting one or more hypervariable region residues of a parent antibody. Generally, the resulting variant(s), i.e., functional equivalents as defined above, selected for further development will have improved biological properties relative to the parent antibody from which they are generated. A convenient way for generating such substitutional variants is by affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed.

In order to identify candidate hypervariable region sites for modification, alanine-scanning mutagenesis may be performed to identify hypervariable region residues contributing significantly to antigen binding. Alternatively, or additionally, it may be beneficial to analyze a crystal structure of the antibody-antigen complex to identify contact points between the antibody and antigen. Such contact residues and neighboring residues are candidates for substitution according to the techniques elaborated herein. Once generated, the panel of variants is subjected to screening as described herein and antibodies with superior properties in one or more relevant assays may be selected for further development.

It may be desirable to modify the antibodies of the present invention, i.e., create functional equivalents, with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Caron et al., 176 J. EXP MED. 1191-95 (1992); Shopes, 148 J. IMMUNOL. 2918-22 (1992). Homodimeric antibodies with enhanced anti-tumor activity may also be prepared using heterobifunctional cross-linkers as described in Wolff et al., 53 CANCER RESEARCH 2560-65 (1993). Alternatively, an antibody can be engineered which has dual Fc regions and may thereby have enhanced complement lysis and ADCC capabilities. Stevenson et al., 3 ANTI-CANCER DRUG DESIGN 219-30 (1989).

To increase the serum half-life of an antibody, one may incorporate a salvage receptor binding epitope into the antibody (especially an immunoglobulin fragment) as described in, for example, U.S. Pat. No. 5,739,277. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Polynucleotide molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site directed) mutagenesis, PCR mutagenesis, and cassette mutagenesis of an earlier prepared variant or a non-variant version of the anti-Kisspeptin/GPR54 antibodies of the present invention.

C. Small Molecule Antagonists of Kisspeptin/GPR54

In other embodiments, a Kisspeptin and/or GPR54 antagonist is a small molecule. As used herein, the term "small molecule organic compounds" refers to organic compounds generally having a molecular weight less than about 5000, 4000, 3000, 2000, 1000, 800, 600, 500, 250 or 100 Daltons, preferably less than about 500 Daltons. A small molecule organic compound may be prepared by synthetic organic techniques, such as by combinatorial chemistry techniques, or it may be a naturally-occurring small molecule organic compound.

In certain embodiments, the antagonist can be the small molecules disclosed and described in U.S. Patent Application, Publication No. 20090156646 ("Pyridylphenol Compounds and Use Thereof); Kobayashi et al., 18 BIOORG. MED. CHEM. 5157-71 (2010) ("2-Acylamino-4,6-diphenylpyridine Derivatives as Novel GPR54 Antagonists with Good Brain Exposure and In Vivo Efficacy for Plasma LH Level in Male Rats"); and Kobayashi et al., 18(11) BIOORG. MED. CHEM. 3841-59 (2010) ("Synthesis and structure-activity-relationships of 2-acylamino-4,6-diphenylpridine Derivatives as Novel Antagonists of GPR54").

Kisspeptin/GPR54 antagonists for use in the present invention can be screened as described in WO 2004/087622 and include, but are not limited to, compounds able to inhibit the activation of GPR54 including compounds capable of interacting with Kisspeptin, to inhibit the binding of Kisspeptin, or to inhibit the activation of GPR54 resulting from the binding. Kisspeptin/GPR54 antagonists also include inhibitors of the expression of Kisspeptin and/or GPR54 such as for instance antisense oligonucleotides, or interfering RNAsi, or ribozymes, targeting the Kisspeptin and/or GPR54 genes.

Compound libraries may be screened for Kisspeptin/GPR54 antagonists. A compound library is a mixture or collection of one or more putative antagonists generated or obtained in any manner. Any type of molecule that is capable of interacting, binding or has affinity for Kisspeptin/GPR54 may be present in the compound library. For example, compound libraries screened using this invention may contain naturally-occurring molecules, such as carbohydrates, monosaccharides, oligosaccharides, polysaccharides, amino acids, peptides, oligopeptides, polypeptides, proteins, receptors, nucleic acids, nucleosides, nucleotides, oligonucleotides, polynucleotides, including DNA and DNA fragments, RNA and RNA fragments and the like, lipids, retinoids, steroids, glycopeptides, glycoproteins, proteoglycans and the like; or analogs or derivatives of naturally-occurring molecules, such as peptidomimetics and the like; and non-naturally occurring molecules, such as "small molecule" organic compounds generated, for example, using combinatorial chemistry techniques; and mixtures thereof.

A library typically contains more than one putative antagonist or member, i.e., a plurality of members or putative antagonists. In certain embodiments, a compound library may comprise less than about 50,000, 25,000, 20,000, 15,000, 10000, 5000, 1000, 500 or 100 putative antagonists, in particular from about 5 to about 100, 5 to about 200, 5 to about 300, 5 to about 400, 5 to about 500, 10 to about 100, 10 to about 200, 10 to about 300, 10 to about 400, 10 to about 500, 10 to about 1000, 20 to about 100, 20 to about 200, 20 to about 300, 20 to about 400, 20 to about 500, 20 to about 1000, 50 to about 100, 50 to about 200, 50 to about 300, 50 to about 400, 50 to about 500, 50 to about 1000, 100 to about 200, 100 to about 300, 100 to about 400, 100 to about 500, 100 to about 1000, 200 to about 300, 200 to about 400, 200 to about 500, 200 to about 1000, 300 to about 500, 300 to about 1000, 300 to 2000, 300 to 3000, 300 to 5000, 300 to 6000, 300 to 10,000, 500 to about 1000, 500 to about 2000, 500 to about 3000, 500 to about 5000, 500 to about 6000, or 500 to about 10,000 putative antagonists. In particular embodiments, a compound library may comprise less than about 50,000, 25,000, 20,000, 15,000, 10,000, 5,000, 1000, or 500 putative antagonists.

A compound library may be prepared or obtained by any means including, but not limited to, combinatorial chemistry techniques, fermentation methods, plant and cellular extraction procedures and the like. A library may be obtained from synthetic or from natural sources such as for example, microbial, plant, marine, viral and animal materials. Methods for making libraries are well-known in the art. See, for example, E. R. Felder, Chimia 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and references cited therein. Compound libraries may also be obtained from commercial sources including, for example, from Maybridge, Chem-Navigator.com, Timtec Corporation, ChemBridge Corporation, A-Syntese-Biotech ApS, Akos-SC, G & J Research Chemicals Ltd., Life Chemicals, Interchim S.A., and Spectrum Info. Ltd.

D. RNA Interference Compositions for Targeting Kisspeptin/GPR54 mRNAs

In one aspect of the present invention, the expression of Kisspeptin and/or GPR54 may be inhibited by the use of RNA interference techniques (RNAi). RNAi is a remarkably efficient process whereby double-stranded RNA (dsRNA) induces the sequence-specific degradation of homologous mRNA in animals and plant cells. See Hutvagner and Zamore, 12 CURR. OPIN. GENET. DEV. 225-32 (2002); Hammond et al., 2 NATURE REV. GEN. 110-19 (2001); Sharp, 15 GENES DEV. 485-90 (2001). RNAi can be triggered, for example, by nucleotide (nt) duplexes of small interfering RNA (siRNA) (Chiu et al., 10 MOL. CELL. 549-61 (2002); Elbashir et al., 411 Nature 494-98 (2001)), micro-RNAs (miRNA), functional small-hairpin RNA (shRNA), or other dsRNAs which are expressed in-vivo using DNA templates with RNA polymerase III promoters. See, e.g., Zeng et al., 9 MOL. CELL. 1327-33 (2002); Paddison et al., 16 GENES DEV. 948-58 (2002); Lee et al., 20 NATURE BIOTECHNOL. 500-05 (2002); Paul et al., 20 NATURE BIOTECHNOL. 505-08 (2002); Tuschl, 20 NATURE BIOTECHNOL. 440-48 (2002); Yu et al., 99(9) PROC. NATL. ACAD. SCI. USA, 6047-52 (2002); McManus et al., 8 RNA 842-50 (2002); Sui et al., 99(6) PROC. NATL. ACAD. SCI. USA 5515-20 (2002). One of ordinary skill in the art can design inhibitory nucleic acid molecules against kisspeptin1 using the readily available nucleic acid sequence thereof.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Animal Studies. Animal studies were approved by the local Institutional Animal use and Care Committee and were performed in 6- to 8-week-old C57Bl/6 male mice. Lepr$^{db/db}$ (Lepr$^{db/db}$; B6.BKS(D)-leprdb/J) mice were from Jackson Laboratories. Gcgrfl/fl were generated by homologous recombination technology (Supplemental Experimental Procedures). Intravenous glucose infusions were performed as described (Alonso et al., 2007).

Adenovirus Injection Studies. Adenovirus (Adv-CRE and Adv-GFP, University of Iowa) were injected into tail vein (109 plaque forming units/mouse in 13PBS). Adenovirus expressing shRNA under U6 promoter was generated (Life Technologies) to target the following mouse Kiss1 sequence: GCTCTCTCTCTTTGACCTAGG (SEQ ID NO:1).

Immunofluorescence Histology and Islet Morphometry. Pancreas immunofluorescence histology and morphometry and pancreas insulin content measurement were conducted as described (Song et al., 2011). Confocal imaging was performed on a Zeiss Axoivert. Antibodies are provided below.

Isolated Islet Studies. Islet isolation was performed by collagenase digestion, gradient centrifugation, and three rounds of microscope-assisted manual picking of islets. Static incubation studies were conducted as previously described with 20 handpicked, equal-sized islets were studied in each group (Song et al., 2011). After overnight culture (37_C, 5% CO2, and 95% O2 in humid chamber) of isolated islets in RPMI 1640 (Mediatech) containing 5 mM glucose, 1% each Na-Pyruvate, HEPES, Penicillin/Streptomycin, and 0.2% BSA, islets were switched to either 10 or 20 mM glucose containing RPMI 1640. Where indicated, Kisspeptin-10 (0-100 nM, and 1 mM), E4 (10 nM), or vehicle (PBS) was added. After 30 min incubation glucose concentrations, supernatant was taken for insulin measurements and pelleted islets were taken in acid ethanol (0.18M HCl in 70% ethanol) for insulin measurements in islets (ELISA, Alpco). Islet protein concentration was measured using the BCA method (Thermo Fisher). Dose response curves of GSIS inhibition by Kisspeptin-54 or Kisspeptin-10 (0-100 nM) to serve as a functional bioassay for plasma kisspeptin1 activity performed at six separate times provided intra-assay and interassay coefficient of variations of 7.3% and 9.2%, respectively.

IBs. IBs were performed as described (Song et al., 2011) in at least three different separately obtained experimental samples. Luminescence images of representative IBs are shown. Corresponding Actin IB show protein loading control.

Human Samples. The Institutional Review Board at Johns Hopkins University approved studies of deidentified human samples. Human tissue and serum samples were obtained from National Disease Research Interchange (NDRI) and Origene. Information on samples is provided in Supplemental Experimental Procedures.

Immunoassays. Kisspeptin1 ELISA for mouse (USCN Life Sciences) and human (Phoenix) were used according to manufacturers' instructions. The mouse ELISA kit failed to recognize kisspeptin in human samples and vice versa.

Statistics. Results are presented as average±SEM. Student's t test was used for single comparisons and ANOVA with Bonferroni adjustment for multiple to calculate differences between groups. A p value of <0.05 was considered significant and indicated with the * symbol.

Animals. Generation of Gcgrfl/fl and Kiss1Rfl/fl mice: Gcgrfl/fl were generated together with Ingenious Targeting Laboratories. A targeting construct for mouse Gcgr was generated by bacterial recombineering with a loxP sequence inserted upstream of the second exon. A second loxP containing cassette including neomycin resistance separately flanked by FLPe (FRT) recognition sequences (Rodriguez et al., 2000) inserted downstream of exon 10. Location of LoxP sites predicted after CRE-mediated recombination lack of any protein product to be generated (FIG. 10). To generate Kiss1Rfl/fl mice, a targeting construct was created as described (Na et al., 2013) and contained a loxP site upstream of the second exon and one loxP containing cassette including neomycin resistance separately flanked by FLPe (FRT) recognition sequences 3' of the second exon. Location of LoxP sites predicted after CRE-mediated recombination lack of the second transmembrane domain of Kiss1R (FIG. 11). The reproductive deficiency of gonadotrope-specific CRE-mediated Kiss1R ablation in Kiss1Rfl/fl mice has been separately reported (Novaira et al., 2013). Homologous recombination of targeting constructs in embryonic stem cells was achieved as described (Mortensen, 2006). Proper insertion was ascertained by PCR screening as well as Southern blot. Chimerae were generated after C57Bl/6 blastocyst injection and embryonic propagation in pseudo-pregnant females. Germline transmission was confirmed by PCR genotyping tail DNA extracts. The first offspring was interbred with Actin-FLPe deleted mice (Jackson Laboratories) (Rodriguez et al., 2000) to eliminate the neomycin cassette. Both Gcgrfl/fl and Kissrfl/fl mice were viable, fertile, transmitted the modified gene in Mendelian pattern and showed no obvious defects in body weight or metabolism. Mice were backcrossed at least 6 times into C57Bl/6 background. Primers used for genotyping mice are provided below.

TABLE 1

Primers used for PCR genotyping mice.

| | | |
|---|---|---|
| Prkar1a fl/fl | FW: | GCA GGC GAG CTA TTA GTT TA (SEQ ID NO: 2) |
| | RV: | CAT CCA TCT CCT ATC CCC TTT (SEQ ID NO: 3) |
| Kiss1R fl/fl | FW: | TTC GTG AAC TAC ATC CAG CAG (SEQ ID NO: 4) |
| | RV: | AGA GTG GCA CAT GTG GCT TG (SEQ ID NO: 5) |
| Gcgr fl/fl | FW: | TCA CCC GTG ATG ATC CCA TGT CTT (SEQ ID NO: 6) |
| | RV: | AGT GGC TCA CAG TGC CTA TTC AGA (SEQ ID NO: 7) |
| Insr fl/fl | FW: | GAT GTG CAC CCC ATG TCT G (SEQ ID NO: 8) |
| | RV: | CTG AAT AGC TGA GAC CAC AG (SEQ ID NO: 9) |
| Lepr$^{db/db}$ | FW: | AGA ACG GAC ACT CTT TGA AGT CTC (SEQ ID NO: 10) |
| | RV: | CAT TCA AAC CAT AGT TTA GGT TTG T (SEQ ID NO: 11) |
| | restriction enzyme digestion (RsaI) after PCR | |

To generate HFD fed glucose intolerant animals, 6-week old C57Bl/6J male mice were fed for 8 weeks a diet containing 60% calories as lipids (Bioserv). Controls were male littermates fed regular diet in parallel. For overnight fasting, animals were restricted access to food overnight from 6 pm until 9 am (=O/N fasted). A subset of mice was refed by allowing unrestricted access to food after overnight fasting for 4 hours before analysis (refed). Mice without any restriction to food (=ad lib fed) were allowed unrestricted access to food at all times.

Intraperitoneal glucose tolerance (ipGTT) and insulin tolerance (ipITT) tests were performed according to standard protocols (Song et al., 2013; Song et al., 2011). After 9 am-3 pm fasting, animals were administered 20% D-glucose (via ip injection), insulin 0.5 U/kg i.p. (Novolin), glucagon (100 µg/kg i.p. (Sigma)). K54 (Gly-Thr-Ser-Leu-Ser-Pro-Pro-Pro-Glu-Ser-Ser-Gly-Ser-Arg-Gln-Gln-Pro-Gly-Leu-Ser-Ala-Pro-His-Ser-Arg-Gln-Ile-Pro-Ala-Pro-Gln-Gly-Ala-Val-Leu-Val-Gln-Arg-Glu-Lys-Asp-Leu-Pro-Asn-Tyr-Asn-Trp-Asn-Ser-Phe-Gly-Leu-Arg-Phe-NH$_2$ (SEQ ID NO:34), 10 nmol; Calbiochem), or K10 (Tyr-Asn-Trp-Asn-Ser-Phe-Gly-Leu-Arg-Phe-NH2 (SEQ ID NO:35), 10 nmol; Calbiochem) was administered simultaneously with glucose during ipGTT. The glucagon receptor antagonist GAI (N-(3-Cyano-6-(1,1-dimethylpropyl)-4,5,6,7-tetrahydro-1-benzothien-2-yl)-2-ethylbutanamide (Qureshi et al., 2004) and its non-active analogue were administered (50 mg/kg i.p. in DMSO) in HFD fed and Lepr$^{db/db}$ mice 60 min before i. GTT. Intraperitoneal pyruvate converstion (1 g/kg i.p.) test (ipPCT) in ΔL-Prkar1a mice was performed in the fed state (9 am) to avoid any confounding effects of fasting-induced elevated endogenous glucagon levels. Tail-vein blood was collected at the indicated times in figures for glucose and insulin measurements. Serum insulin was measured using mouse magnetic bead panel (Millipore, Luminex). Plasma for glucagon measurements was drawn from mice in the fed state at 9 am, unless otherwise noted for fasting studies. Plasma glucagon (Alpco) and kisspeptin1 (USCN Life Sciences Inc. E92559Ra) were measured by ELISA according to manufacturer's instructions including dilution of samples. Because kisspeptin1 ELISA detects K10 and does not differentiate between the various bioactive kisspeptin1 breakdown products, the plasma concentrations measured with ELISA are provided according to manufacturers' instructions and were not converted into SI units.

All animal studies were performed at least in triplicate. For studies involving standard (Taconic) and high fat diet (60% calories from saturated fat; Bioserv) care was taken to assign littermates to different diets and to perform tests in age matched animals. Animals were randomized to different treatments described herein. Replicates were obtained testing different individual animals and not by repeat testing the same animal. Animal tests and sample measurements (e.g., ELISA) from animal tests were performed in a blinded manner.

Adenovirus (Adv-CRE and Adv-GFP, University of Iowa Genetics Core) were injected into tail vein (109 plaque forming units/mouse in 1×PBS). Adv-CRE injection into mice carrying a floxed stop codons upstream of YFP at the Rosa26 locus (Jackson Laboratories) showed 95% of hepatocytes are transduced with CRE recombinase. Occasional recombination was found in lung tissue but not in brain, heart, kidney, pancreas, islet, spleen, muscle confirming strong liver targeting by injected adenovirus (not shown). Immunoblots of islets, hypothalamus, adipose tissue, and skeletal muscle in L-Δprkar1a, L-ΔGcgr, L-ΔInsr mice confirmed that, Prkar1a, Gcgr, and Insr were expressed at unchanged levels relative to control (Adv-GFP treated counterparts) and that corresponding floxed genes had not been ablated in these tissues by Adv-CRE treatment.

In Vivo Cannulation and Perfusion. For catheterization, mice were anesthetized with inhaled 2% isoflurane. Microrenathane catheters (Braintree Scientific) were inserted in the left femoral artery and vein, sutured in place, stabilized with superglue (Henkel), tunneled subcutaneously to the upper back by threading through a blunt needle, taped to a wire attached to posterior cervical muscles for stiffness (A-M-Systems), and connected to a 360° dual channel swivel designed for mice (Instech, Plymouth Meeting). Mice received infusions of 0.9% sodium chloride or 50% dextrose. Detailed protocols are provided in reference (Alonso et al., 2007).

Immunohistochemistry and Pancreas Morphometrical Analysis. At least 3 Bouin's-fixed and paraffin embedded pancreas sections/mouse 150 µM apart were immunostained and analyzed for islet/β-, α- and δ-cell mass as described (Song et al., 2011). Confocal imaging was performed on a fluorescence microscope (Zeiss) equipped with confocal and digital image capturing capabilities.

Gene Expression Analysis. Microarray expression profiles were generated using the Illumina MouseRef-8 v2 BeadChips (Illumina, San Diego, Calif.) by the Genome Sciences Laboratory at the University of Virginia. Biotin-labeled cRNA was synthesized by the total prep RNA amplification kit from Ambion (Austin, Tex.). cRNA was quantified and normalized to 150 ng/ul, and then 750 ng was hybridized to each BeadChip. The image data was then acquired by scanning the chips on an Illumina iScan. The raw idat files were uploaded into the Illumina Genomestudio software and the data exported for analysis. Sample and control probe signal intensities were exported from GenomeStudio. These files were imported into R version 2.15.0, quantile normalized, and log 2 transformed using the Bioconductor beadarray package, version 2.6.0, and Illumina probe IDs were annotated using the Bioconductor illuminaMousev2.db package, version 1.16.0. The BioConductor array QualityMetrics package, version 3.12.0 was used to perform quality assessment. For examining differential gene expression, a linear model was with empirical-Bayes moderated standard errors using the limma package, version 3.14.11. Gene-set enrichment analysis (GSEA) was used to examine differential expression results for enriched pathways (Smyth, 2004; Subramanian et al., 2005). SignalP 4.0 was used with the default parameters to determine which differentially expressed genes contained a cellular export signal based on the amino acid sequence (Petersen et al., 2011). A cut-off for False discovery rate-corrected P<0.05 and log 2 Fold Change (FC)>2 was used to identify a significant change in gene expression. Array results of interest were validated by quantitative RT-PCR (qRT-PCR).

RT-PCR. RNA was isolated using Illustra RNAspin combined with removal of DNA by DNAseI digestion (GE Healthcare). QPCR was carried out following standard procedures using SYBR green (BioRad) using mouse primers indicated in Table1. Expression levels were calculated using the 2-ΔΔCT method with 18S rRNA as internal control (Livak and Schmittgen, 2001). PCR primers are provided below.

TABLE 2

| Primers used for quantitative PCR. | | |
|---|---|---|
| Kiss1 | Kiss1 F: | GCATACCGCGATTCCTTTTT (SEQ ID NO: 12) |
| | Kiss1 R: | AGCTGCTGCTTCTCCTCTGT (SEQ ID NO: 13) |
| Gcgr | GCGR F: | TGCTGTTTGTCATCCCCTG (SEQ ID NO: 14) |
| | GCGR R: | CAGGAAGACAGGAATACGCAG (SEQ ID NO: 15) |
| Kiss1R | Gpr54 F: | GCAAATTCGTCAACTACATCCAG (SEQ ID NO: 16) |
| | Gpr54 R: | GGGAACACAGTCACATACCAG (SEQ ID NO: 17) |

TABLE 2-continued

Primers used for quantitative PCR.

| | | | |
|---|---|---|---|
| sRNA | 18S-F: | GCAATTATTCCCCATGAACG | (SEQ ID NO: 18) |
| | S-R: | GGCCTCACTAAACCATCCAA | (SEQ ID NO: 19) |
| Actin | Act F: | AGCCATGTACGTAGCCATCC | (SEQ ID NO: 20) |
| | Act R: | CTCTCAGCTGTGGTGGTGAA | (SEQ ID NO: 21) |
| Ppargc1a | Pgc1 F: | CAGCCTCTTTGCCCAGATCT | (SEQ ID NO: 22) |
| | Pgc1 R: | CCGCTAGCAAGTTTGCCTCA | (SEQ ID NO: 23) |
| Src1 | Src1 F: | AGGAGTGATAGAGAAGGAGTCG | (SEQ ID NO: 24) |
| | Src1 R: | TGATTGTAACCCAAGTAGCTGG | (SEQ ID NO: 25) |
| Pck1 | Pck1 F: | CTGCATAACGGTCTGGACTTC | (SEQ ID NO: 26) |
| | Pck1 R: | CAGCAACTGCCCGTACTCC | (SEQ ID NO: 27) |
| G6P | G6p F: | CGACTCGCTATCTCCAAGTGA | (SEQ ID NO: 28) |
| | G6p R: | GTTGAACCAGTCTCCGACCA | (SEQ ID NO: 29) |
| For ChIP assay | | | |
| Kiss1pr CRE1 | KCRE1 F: | TGTCGTCTTTGGCTTCCT | (SEQ ID NO: 30) |
| | KCRE1 R: | TGCACCTAGGGTAGCAC | (SEQ ID NO: 31) |
| Kiss1pr CRE2 | KCRE2 F | AGGCGAGTGCCTTGAAC | (SEQ ID NO: 32) |
| | KCRE2 R: | CCACTTTCTTCTGGACTTGGA | (SEQ ID NO: 33) |

Islet studies. Islet isolation was performed by collagenase digestion, gradient centrifugation and three rounds of microscope-assisted manual picking of islets (Song et al., 2011). Static incubation studies were conducted as previously described with 20 hand-picked equalized islets were studied in each group. Islets were cultured in RPMI 1640 medium (Invitrogen) containing 10 or 20 mM D-glucose (as indicated) and supplemented with 0.2% bovine serum albumin, 1% each Na-Pyruvate, HEPES, Penicillin/Streptomycin. After 30 min incubation glucose concentrations, supernatant was taken for insulin measurements and pelleted islets were taken in acid ethanol (0.18M HCl in 70% ethanol) for insulin measurements in islets (Alpco). Islet protein concentration was measured using the BCA method (Thermo Fisher).

Insulin secretion during static incubation. After overnight culture (37 C, 5% CO2, 95% O2 in humid chamber) of isolated islets in RPMI 1640 (Mediatech) containing 5 mM glucose, 1% each Na-Pyruvate, HEPES, Penicillin/Streptomycin and 0.2% bovine serum albumin (BSA), islets were switched to either 10 or 20 mM glucose containing RPMI 1640. Where indicated, Kisspeptin-10 (K10) or Kisspeptin-54 (K54) (0-100 nM, and 1 µM), E4 (10 nM) or vehicle (PBS) was added. After 30 min incubation glucose concentrations, supernatant was taken for insulin measurements and pelleted islets were taken in acid ethanol (0.18M HCl in 70% ethanol) for insulin measurements in islets (ELISA, Alpco). Islet protein concentration was measured using the BCA method (Thermo Fisher). Dose response curves of GSIS inhibition by Kisspeptin-54 or -10 (0-100 nM) to serve as a functional bioassay for plasma kisspeptin1 activity performed at 6 separate times provided intra-assay and interassay coefficient of variations of 7.3% and 9.2%, respectively.

For studies with plasma incubation, a final concentration of plasma was 1% or 10% (vol/vol). Plasma was treated with a protease inhibitor cocktail containing 4-(2-Aminoethyl) benzenesulfonyl fluoride hydrochloride (1 mM), Aprotinin (0.8 µM), bestatin (50 µM), (1S,2S)-2-(((S)-1-((4-Guanidinobutyl)amino)-4-methyl-1-oxopentan-2-yl)carbamoyl)cyclopropanecarboxylic acid (15 µM), EDTA (5 µM), leupeptin (20 µM), pepstatin A (10 µM) (Liu et al., 2013) (Thermo-Fisher), K54, K10, E4 were added at the concentrations indicated in the relevant figures. Islets were taken in 0.18M HCL/70% ethanol to extract and measure total islet insulin content. cAMP concentrations were measured in islet extracts using ELISA (Enzo Life Sciences).

Perifusion studies were performed as previously published (Song et al., 2013; Song et al., 2011) with slight modifications. The perifusate was Krebs ringer buffer (KRB) (37 C, pH 7.4) containing 0.2% BSA fraction V, 24 mM sodium bicarbonate and was gassed with 95% air and 5% CO2. Perifusion (1 ml/min) occurred for the first 30 minutes with a KRB containing 3 mM glucose for equilibration, after which time the perifusate was collected in 1 ml fractions. After additional 10 minutes, glucose in the perifusate was increased to 10 mM. Where indicated, K10 (10 nM) or E4 (10 nM) was added to the perifusate. Insulin was measured in selected individual eluent fractions at 30, 35, 40, 42, 45, 50, 55, 60 min (Alpco ELISA). The first 10 minutes after increasing glucose was defined as first phase, the period thereafter was defined as second phase of insulin secretion. At the end of the perifusion protocol, 30 mM KCL was administered into the perifusate to depolarize β-cells. Insulin levels were normalized to total islet protein, which was spectrophotometrically determined (Eppendorf) after completion of the perifusion protocol.

Cell Culture Studies. Mouse primary hepatocytes were isolated and cultured as described (He et al., 2009). H2.35 hepatoma cell line was cultured and transfected as described (He et al., 2009). 1 kb of the 5' untranslated region of the mouse Kiss1 gene were cloned by PCR into pGL4. The CRE half sites (TGCAT) within the promoter region were mutated by site directed mutagenesis to (TATGT). Luciferase activity was measured in cell lysates using a luminometer (Berthold) after treatment each for 2 hours with forskolin/IBMX (100 µM each) or glucagon (200 pg/ml) or/and insulin (2000 pg/ml). Dominant-negative A-CREB (Ahn et al., 1998) and WT CREB were from Addgene. Constitutively active CREB Y134F (Du et al., 2000) was generated by site directed mutagenesis of WT CREB.

Protein Immunoblots. Immunoblots (IB) were performed with 40-50 µg protein taken in lysis buffer (Cell Signaling). Representative blots are shown. Actin IB of corresponding samples are shown for protein loading references. Chromatin immunoprecipitation studies were performed as described (Song et al., 2011). Antibodies used are listed below.

TABLE 3

Primary antibodies used for immunoblots and immunohistochemistry.

| Antibody | Vendor | Cat. No. | Fold Dilution |
|---|---|---|---|
| Mouse anti-Actin | Millipore | MAB1501 | 4000 |
| Mouse anti-PKA[RI] | BD Transduction Laboratories | 610165 | 500 |
| Mouse anti-PKA[RIa] | BD Transduction Laboratories | 610609 | 250 |
| Mouse anti-PKA[RIIa] | BD Transduction Laboratories | 612242 | 2000 |
| Mouse anti-PKA[RIIB] | BD Transduction Laboratories | 610625 | 2000 |
| Mouse anti-PKA[C] | BD Transduction Laboratories | 610980 | 2000 |
| Rabbit anti-CREB-1 | Santa Cruz | sc-58 | 100 |
| Rabbit anti- Ser133-Phospho CREB | Abcam | ab30651 | 500 |
| Rabbit anti Kisspeptin10 | Millipore | AB9754 | 400 |
| Rabbit anti-Kiss1R | Phoenix Pharmaceuticals | H-001-64 | 200 |
| Rabbit anti glucagon receptor | Novus biological | NBP1-00850 | 400 |
| Mouse anti-insulin receptor | Abcam | ab69508 | 1000 |
| Guinea-pig anti-insulin | DAKO | A0564 | 1000 |
| Rabbit anti-glucagon | Zymed | 18-0064 | 550 |
| Rabbit anti-somatostatin | DAKO | A0566 | 200 |

Human Studies. Tests on de-identified human samples were approved by the Johns Hopkins University Institutional Review Board. Liver tissue from humans without diabetes mellitus and with T2DM were obtained from Origene and National Disease Research Interchange (NDRI). Serum samples from humans without and with T2DM were from NDRI. Samples from T2DM were from poorly controlled diabetics, not receiving insulin or metformin treatment. Details of samples are provided below.

TABLE 4

Human liver tissue and islet information

| Tissue | Source | Gender | Age | Diagnosis | Treatment | Cause of Death |
|---|---|---|---|---|---|---|
| Liver | NDRI OD26532 | Female | 65 y | T2DM x2 weeks, HTN | none | CV stroke |
| Liver | NDRI OD26278 | Male | 94 y | T2DM x 31 y | glipizide, lisinopril | Resp. failure |
| Liver | NDRI OD2072 | Male | 78 y | T2DM untreated | none | Cardiac arrest |
| Liver | Origene CP565754 | Not provided | Not provided | Normal, no T2DM | none | Not provided |
| Liver | Origene CP565527 | Not provided | Not provided | Normal, no T2DM | none | Not provided |
| Liver | Origene CP565735 | Not provided | Not provided | no T2DM | none | Not provided |
| Islet protein | NDRI OD18253 | Female | 40 y | Normal, no T2DM | none | CV stroke |
| Islet protein | NDRI OD1860 | Male | 65 y | Normal, no T2DM | none | CV stroke |
| Islet protein | NDRI OD40157 | Male | 27 y | Normal, no T2DM | none | trauma |

Results

Disinhibited PKA Activity in Liver Causes Impaired GSIS Independent of Hyperglycemia. To mimic upregulated glucagon-cAMP-PKA signaling in vivo in mouse liver independently of glucagon action in other tissues, we selectively disinhibited liver PKA catalytic (PKAc) activity by ablating hepatic PKA regulatory subunit 1A (Prkar1a) using the CRE/LoxP method. Mice homozygous for floxed Prkar1a (Prkar1afl/fl mice) (Kirschner et al., 2005) were treated by tail vein injection with adenovirus driving CRE recombinase under control of the CMV promoter (Adv-CRE) to generate mice selectively lacking liver Prkar1a (L-Δprkar1a mice). Control mice received adenovirus expressing GFP (Adv-GFP).

Figure 1:
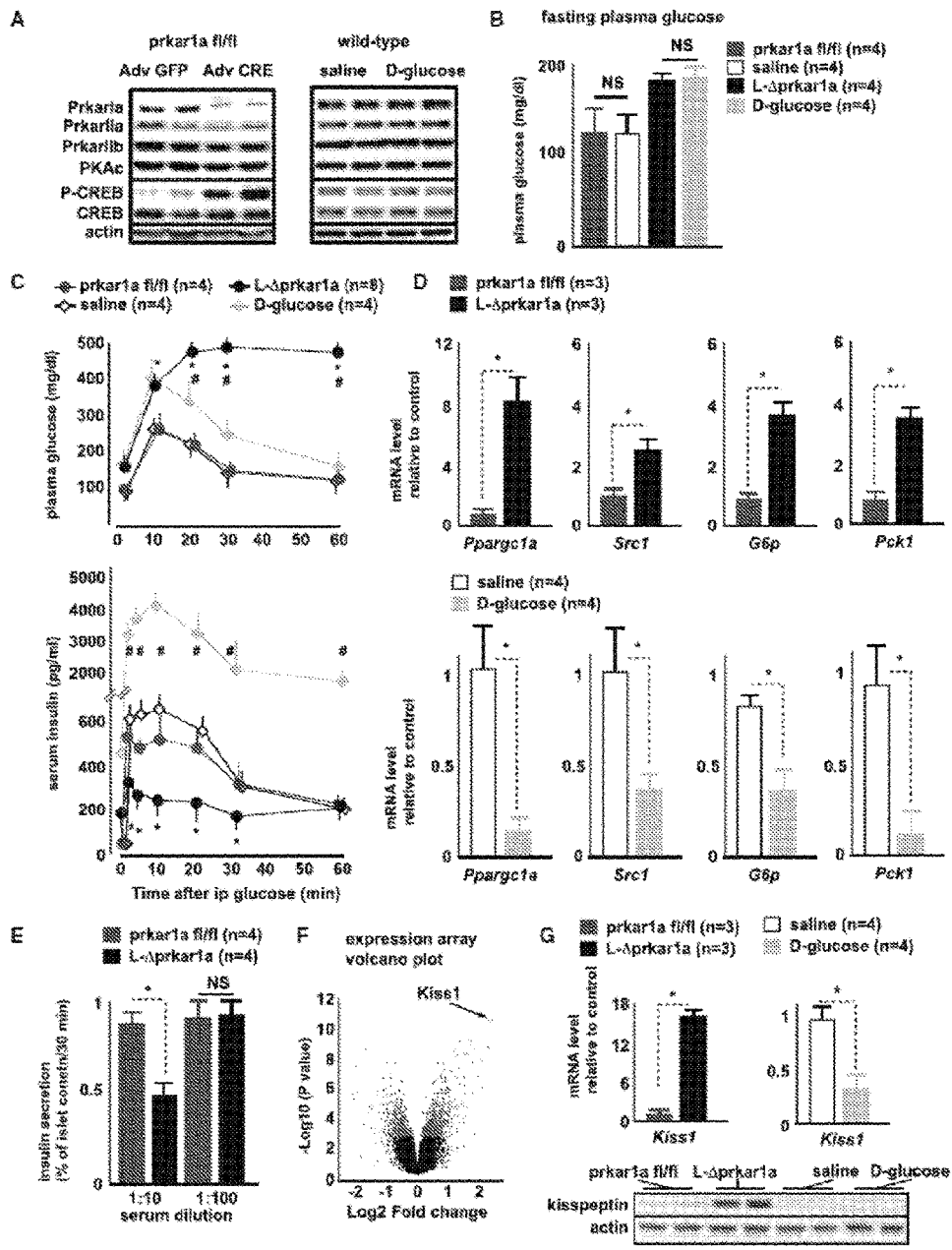
FIG. 1. Comparison between L-Δprkar1a and D-Glucose Mice Identifies Kiss1 (A) (Left) Representative liver IB of prkar1afl/fl and L-Δprkar1a 4 days after adenovirus treatment. L-Δprkar1a mice show Prkar1a ablation and increased *pCREB (right). Liver IB from saline and D-glucose mice shows unaltered Prkar subtypes, Pkac, and pCREB. (B) Fasting glucose levels in prkar1afl/fl, L-Δprkar1a, saline, and D-glucose mice. Prkar1afl/fl and saline mice have similar fasting glucose; D-glucose infusion achieves fasting glucose similar to L-Δprkar1a mice (mean±SEM; *p<0.05). (C) (Top) plasma glucose and (bottom) serum insulin during ipGTT in prkar1afl/fl, L-Δprkar1a, saline, and D-glucose mice. L-Δprkar1a mice exhibit impaired GT (top) and GSIS (bottom). D-glucose mice have mildly impaired GT and robust GSIS. Prkar1a fl/fl and Sal-mice have similar GT and GSIS (mean±SEM; *p<0.05). (D) qRT-PCR of indicated genes of gluconeogenic program in prkar1afl/fl, L-Δprkar1a, Sal-, and D-glucose-mouse livers. (Top) Gluconeogenic program is upregulated in L-Δprkar1a as compared to prkar1afl/fl mice; (bottom) gluconeogenic program is downregulated in D-glucose as compared to saline mice (mean±SEM; *p<0.05). (E) GSIS of WT mouse islets cultured in serum-free media conditioned with plasma of prkar1afl/fl or L-Δprkar1a mice. Prkar1afl/fl plasma does not affect GSIS. L-Δprkar1a plasma at 1:10 but not at 1:100 dilution suppresses GSIS (mean±SEM; *p<0.05). (F) Volcano plot of gene expression analysis of liver from prkar1afl/fl and L-Δprkar1a mice. Significant upregulation of Kiss1 transcript is detected in L-Δprkar1a mice. (G) (Top) qRT-PCR of Kiss1 transcript and (bottom) IB in liver tissue from mice with indicated liver genetic complement or intravenous infusion. L-Δprkar1a liver shows increased Kiss1 transcript and kisspeptin protein. D-glucose mice show Kiss1 downregulation as compared to controls (mean±SEM; *p<0.05).
Figure 8:
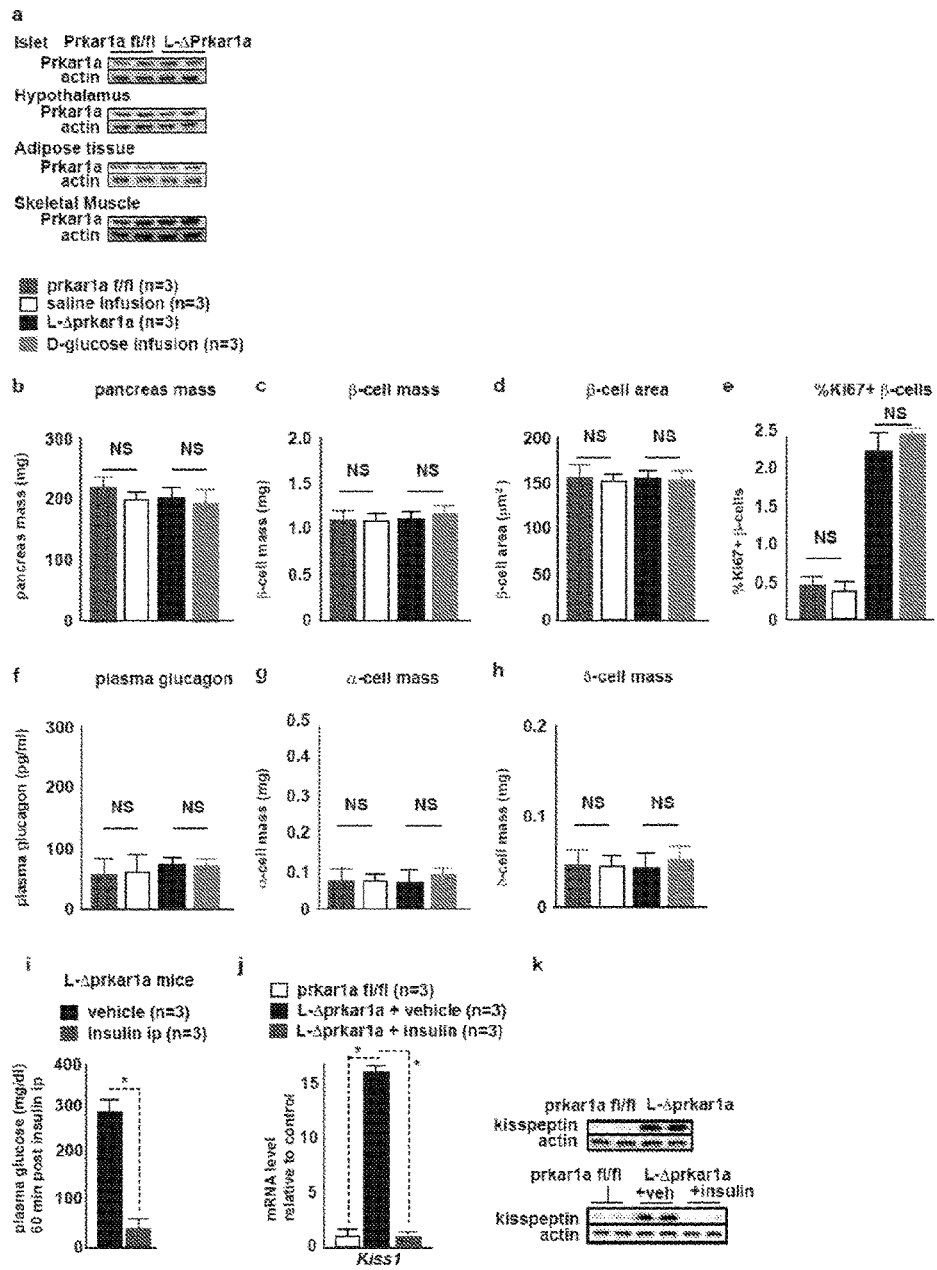
FIG. 8. Pancreas morphometric parameters and plasma glucagon levels are similar in prkar1afl/fl and saline-infused as well as in L-Δprkar1a and D-glucose infused mice (A-G). A: Representative IB of prkar1a in islets, hypothalamus, adipose tissue and skeletal muscle in prkar1afl/fl and L-Δprkar1a. Actin IB is shown for protein loading control, B Pancreas mass, C β-cell mass, D individual β-cell area, E Percent Ki67 positive β-cells, F plasma glucagon levels, G α-cell mass, and H δ-cell mass, respectively in prkar1afl/fl and saline-infused as well as in L-Δprkar1a and D-glucose infused mice. A: Adv-CRE treatment does affect prkar1a expression outside of the liver (see also FIG. 1A) B-G: β-cell proliferation is increased in L-Δprkar1a 4 days after receiving Adv-CRE treatment as compared to prkar1afl/fl mice; and β-cell proliferation is similarly increased in mice receiving 4 days of D-glucose infusions as compared to saline-infused mice. All other parameters are similar in all groups of mice (mean+SEM, *p<0.05).

Liver extracts harvested four days after injection from Adv-CRE injected mice revealed a 90% reduction in Prkar1a protein (FIG. 1A), while other Prkar isoforms and Pkac levels remained unaltered. As expected, L-Δprkar1a mice, as opposed to controls, exhibited increased hepatic phosphorylation of cAMPresponse element binding protein (CREB) at serine 133 (pCREB), an established PKAc target (Gonzalez and Montminy, 1989) (FIG. 1A). Adv-CRE treatment did not affect Prkar1a expression in islet, hypothalamus, adipose tissue, and skeletal muscle (FIG. 8A available online). Liver-specific PKA disinhibition stimulated within 4 days hepatic expression of transcriptional coactivators (Ppargc1a and Src1) and rate-limiting enzymes (G6p and Pck1) of the gluconeogenic pathway (Louet et al., 2010), which resulted in fasting hyperglycemia and notably also in insufficient insulin secretion to correct glycemia during intraperitoneal glucose tolerance tests (ipGTT) (FIGS. 1C and 1D).

To assess whether hyperglycemia during 4 days is directly associated with impaired GSIS, we generated a model of chronic hyperglycemia without hepatic PKA-CREB activation. Wild-type (WT) mice were intravenously infused during 4 days with D-glucose (D-glucose mice) to achieve fasting glucose levels to match those measured in L-Δprkar1a mice (FIG. 1B). Mice infused with saline served as controls (saline mice). D-glucose mice exhibited no change in liver pCREB (FIG. 1A) and reduced gene expression of the gluconeogenic program (FIG. 1D). In contrast to L-Δprkar1a mice, D-glucose mice showed increased GSIS and only mildly impaired GT (FIG. 1C). Both L-Δprkar1a and D-glucose mice showed similar increases in β cell proliferation, as assessed by Ki67 expression (FIG. 8E); albeit, pancreas morphometric parameters or plasma glucagon levels in L-Δprkar1a and D-glucose-infused mice did not change during the short 4 day protocols (FIG. 8B-S1H), excluding differences in b or a cell mass or in glucagon action to account for the differences in glucose homeostasis.

Selective PKA Disinhibition in Liver Induces Secreted Neuropeptide Kiss1. The liver secretes factors that regulate pancreatic a or β cell growth and that, in part, have been identified by liver gene expression analyses (El Ouaamari et al., 2013; Longuet et al., 2013; Yi et al., 2013). We reasoned that the liver may also secrete a factor(s) that regulates β cell function and that may be altered in L-Δprkar1a mice. We therefore treated isolated WT mouse islets with serum-free media conditioned with plasma extracted from L-Δprkar1a or control mice and examined GSIS at 10 mM glucose. Plasma in 1:10 dilution from L-Δprkar1a, but not from control, mice suppressed GSIS (FIG. 1E). 1:100 diluted L-Δprkar1a plasma did not suppress GSIS in this functional bioassay. These observations suggested that PKA signaling in the liver generates a secreted molecule(s) that suppresses β cell GSIS in a dose-dependent fashion (FIG. 1E).

To identify this PKA-regulated factor, we analyzed by microarray L-Δprkar1a and control mouse livers for differentially expressed genes encoding secreted proteins. We identified a single candidate transcript encoding kisspeptin1 (Kiss1) (FIG. 1F) to be elevated in liver tissue of L-Δprkar1a mice (p<10_11; log 2FC=2.17). Quantitative RT-PCR (qRT-PCR) and immunoblots (IBs) of liver tissue confirmed increased hepatic kisspeptin1 production in L-Δprkar1a mice (FIG. 1G). Conversely, liver Kiss1 was reduced by 50% in D-glucose mice (FIG. 1G).

Glucagon Stimulates Hepatic Kiss1 Expression Via Gcgr and cAMP-PKA-CREB Signaling. We next examined whether glucagon directly stimulates hepatic kisspeptin1 production. Glucagon treatment (200 pg/ml) of primary mouse hepatocytes stimulated within 2 hr Kiss1 expression and protein (FIGS. 2A-2C). As expected, the gluconeogenic gene Pck1, an internal control, was also stimulated by glucagon (FIG. 2A). Consistent with glucagon-activated cAMP-PKA signaling, mouse hepatocytes treated for 2 hr with the adenylyl cyclase activator forskolin (fsk) plus the phosphodiesterase inhibitor 3-isobutyl-1-methylxanthine (IBMX) exhibited increased Kiss1 expression (FIG. 2B).

A luciferase reporter plasmid containing 1 kb of the mouse Kiss1 promoter element transfected into mouse H2.35 hepatoma cells showed transcriptional activation in response to glucagon or to fsk/IBMX treatment (FIG. 9A). The mouse Kiss1 promoter contains two putative functional cAMP response element (CRE) half-sites (TGACT) (Zhang et al., 2005) located at _127 and _758 bp upstream of the Kiss1 transcription start site. Mutation of either of the CRE half-sites decreased the transcriptional responses to glucagon or to fsk/IBMX, and combined mutation of both CRE half-sites further decreased the responses (FIG. 9A).

In accordance with CREB mediating cAMP-stimulated Kiss1 transcription, cotransfection in H2.35 cells with constitutively active CREB Y134F stimulated Kiss1 reporter activity as long as CRE 1 and CRE2 sites were intact, while dominant negative CREB inhibitor A-CREB blocked reporter stimulation by fsk/IBMX (FIGS. 9B and 9C). Consistent with these findings is robust cAMP-PKA-CREB responsiveness of the human Kiss1 promoter, which contains a functional CRE half-site at _45 bp proximal to the transcription start site (Zhang et al., 2005). Chromatin of mouse liver extracts using nonspecific versus CREB specific antiserum combined with qPCR of CRE half-site sequences (in vivo chromatin immunoprecipitation), confirmed in vivo CREB occupancy of both CRE half-sites within the Kiss1 promoter (FIG. 9D).

Intraperitoneal (ip) glucagon (16 mg/kg) but not PBS, treatment in mice increased hepatic kisspeptin1 production 30 min after injection (FIGS. 2D and 2E). Physiologic endogenous glucagon secretion provoked by overnight fasting (FIG. 9E) resulted in increased hepatic kisspeptin1 production when compared to ad-libitum-fed mice (FIGS. 2F and 2G). Fasted and subsequently refed mice exhibited a reduction in blood glucagon levels (FIG. 9D) and also of liver Kiss1 mRNA and kisspeptin1 protein (FIGS. 2F and 2G). Kiss1 transcript was also detectable by qRT-PCR at low levels in spleen, kidney, skeletal muscle, and epididymal fat tissue. In these tissues, Kiss1 expression remained unchanged during fasting (data not shown), indicating that the liver is the main site where Kiss1 expression is regulated by metabolic cues.

To confirm the role of the liver glucagon receptor in mediating in vivo effects of glucagon on hepatic kisspeptin1 production, we generated floxed glucagon receptor (Gcgrfl/fl) mice (FIG. 10A), in which we conditionally ablated liver Gcgr by Adv-CRE delivery (L-ΔGcgr mice) (FIG. 10B). Adv-GFP injected Gcgrfl/fl mice served as controls. Adv-CRE treatment did not ablate Gcgr in islet, hypothalamus, and adipose tissue (FIG. 10B). Deprivation of hepatic glucagon signaling in L-ΔGcgr mice resulted in reduced fasting glucose levels, improved GT, and unchanged insulin tolerance (FIGS. 10C and 10D). L-ΔGcgr mice showed, as compared to controls, slightly but not significantly reduced liver kisspeptin1 expression (FIG. 2H,I). Importantly, in L-ΔGcgr mice, kisspeptin production did not change in response to ip glucagon treatment or after overnight fasting (FIGS. 2J and 2K). Plasma kisspeptin levels in Gcgrfl/fl and L-ΔGcgr mice reflected respectively, changes in liver kisspeptin production in response to glucagon treatment or fasting (FIGS. 9G and 9H). Furthermore, L-ΔGcgr mice showed, as compared to controls, significantly dampened liver CREB phosphorylation and CREB occupancy of the Kiss1 promoter CRE half-sites in response to glucagon treatment or to overnight fasting (FIGS. 10E and 10F).

Glucagon and Insulin Counterregulate Liver Kisspeptin1 Expression. In the liver, insulin counteracts glucagon action on cAMP-CREB regulated genes (He et al., 2009). Accordingly, in vitro insulin treatment (2000 pg/ml) of mouse hepatocytes reduced basal Kiss1 expression and, as expected, also reduced Pck1 expression (FIG. 2A). Insulin treatment dampened glucagon stimulated Kiss1 and Pck1 expression in mouse hepatocytes (FIG. 2A). Changes in Kiss1 expression were qualitatively reflected in corresponding changes in kisspeptin1 protein levels in response to glucagon and insulin treatment, respectively (FIG. 2C).

To verify that in vivo insulin effects on liver Kiss1 expression are directly mediated by liver insulin receptors and to examine whether isolated hepatic insulin resistance may modulate Kiss1 expression, we generated mice with liver-specific insulin receptor deficiency by Adv-CRE treatment of floxed insulin receptor (Insrfl/fl) mice (Bruning et al., 1997) (L-ΔInsr mice; FIG. 2L). Importantly, Insr expression in islets, hypothalamus, adipose tissue, and skeletal muscle was not different between Insrfl/fl and L-ΔInsr mice (FIG. 9F). Hepatic ablation of insulin receptor by Adv-CRE in mice did not change liver Kiss1 mRNA or protein levels (FIGS. 2M-2O). Conversely, glucagon treatment of L-ΔInsr mice, as compared to Insrfl/fl mice, dramatically increased liver Kiss1 transcript and kisspeptin protein (FIGS. 2N and 2O). Plasma kisspeptin1 levels in Insrfl/fl and L-ΔInsr mice, respectively, reflected the changes in liver kisspeptin production (FIG. 9I).

Consistent with these observations of insulin counterregulation of PKA-mediated Kiss1 stimulation, in vivo ip insulin (1 IU/kg) administration in L-Δprkar1a mice to supplement relatively deficient endogenous serum insulin concentrations and to achieve blood glucose reduction, decreased hepatic Kiss1 mRNA and protein levels within 60 min (FIGS. 8I-8K).

These findings indicate that—as is established for cAMP CREB-responsive gluconeogenic genes-insulin at sufficiently high concentrations antagonizes glucagon stimulation of Kiss1 expression. Further, in vivo disruption of the hepatic insulin receptor (i.e., liver insulin resistance) alone does not derepress liver kisspeptin1 production absent additional glucagon signaling. These findings also indicate that the liver is the predominant source of circulating kisspeptin1, which is subject to hormonal regulation.

Kisspeptin1 Knockdown in L-Δprkar1a Mice Ameliorates GSIS Despite Continued Gluconeogenesis. To verify that in L-Δprkar1a mice hepatic kisspeptin1 is directly linked to impaired GSIS, we knocked down hepatic kisspeptin1 in L-Δprkar1a mice by administering adenovirus expressing Kiss1-specific shRNA (Adv-Kiss1 shRNA) or a control scrambled shRNA adenovirus (Adv-scr shRNA). Within 3 days of treatment, Adv-Kiss1-shRNA-treated mice showed reduced hepatic Kiss1 mRNA and plasma kisspeptin (FIG. 3A). In contrast, gluconeogenesis, as reflected by mRNA of the gluconeogenic genes (FIG. 3B) as well as functional conversion of ip administered gluconeogenic precursor pyruvate to glucose in the fed (nonfasting) state (ip pyruvate conversion test) was similar between Adv-Kiss1 shRNA and control Adv-scr-shRNA-treated L-Δprkar1a mice and also significantly increased as compared to WT mice (FIG. 3D). Furthermore, liver CREB phosphorylation and CREB occupancy of the endogenous Kiss1 promoter was similar in Adv-scr shRNA and Adv-Kiss1-shRNA-treated L-Δprkar1a mice (FIGS. 3B and 3C), indicating that PKA signaling per se is not differentially affected by Kiss1-specific versus scr shRNA treatment.

Despite ongoing upregulated hepatic gluconeogenesis (FIGS. 3B-3D), Kiss1 knockdown in L-Δprkar1a mice increased in vivo GSIS and improved GT (FIGS. 3F and 3G). ipITT (FIG. 3E), food intake, and body weight (FIGS. 3H and 3I) were similar in Adv-Kiss1 and Adv-scr-shRNA-treated L-Δprkar1a mice, excluding differences in insulin sensitivity or caloric intake in Adv-Kiss1 versus Adv-scr-shRNA-treated animals as mechanisms, respectively, for improved GT or for a compensatory increase in insulin secretion in the face of altered insulin resistance.

Kisspeptin Impairs GSIS at Nanomolar Concentrations Via Interaction with its Receptor Kiss1R on Pancreatic βCells. The Kiss1R shares 82% homology between humans and mouse (Ohtaki et al., 2001). IB confirmed Kiss1R expression in protein extracts of mouse islets, in INS1 and Min6 insulinoma cells, and in human islets (FIG. 4A). Immunohistochemistry combined with confocal imaging of mouse pancreas localized Kiss1R expression to insulin-producing pancreatic β cells but not to α cells (FIG. 4B), indicating that kisspeptin1-Kiss1R signaling likely occurs directly on β cells.

To specifically investigate the functional role of Kiss1R on β cells in mediating kisspeptin1 action on GSIS, we generated mice lacking pancreatic Kiss1R by interbreeding PDX1-CRE (Lammert et al., 2001) and floxed Kiss1R (Kiss1rfl/fl) (Novaira et al., 2013) mice to yield Panc-DKiss1R mice (FIG. 11A). Analysis of pancreata revealed similar morphometric parameters and insulin content in control and Panc-DKiss1R mice (FIG. 11B). Panc-DKiss1R mice, as compared to Kiss1rfl/fl controls, exhibited similar plasma glucagon levels (FIG. 11B), slightly elevated fasting serum insulin levels, similar glucose levels, and similar GT during ipGTT (FIG. 4C). In contrast, treatment with K54 (10 nmol ip) suppressed GSIS in Kiss1rfl/fl mice but did not affect GSIS in Panc-DKiss1R mice (FIG. 4D). Together with the confocal microscopic observation, which localized Kiss1R within the endocrine pancreas restricted to β cells (FIG. 4B), these results indicate that kisspeptin1 suppresses GSIS by direct action via its receptor on β cells.

Synthetic K54 suppressed GSIS in a dose-dependent manner and at concentrations as low as 0.1 nM from Kiss1Rfl/fl mouse islets that were cultured in serum-free media containing either 10 or 20 mM glucose (FIG. 4E, top), whereas Panc-DKiss1R mice were impervious to K54-mediated GSIS suppression (FIG. 4E, bottom). K10 tested at concentrations equimolar to K54 was equally effective in suppressing GSIS in vivo and in vitro (not shown).

Kisspeptin at different concentrations has been reported to either suppress or stimulate GSIS. Kisspeptin isoforms at nM concentrations suppress GSIS (Silvestre et al., 2008; Vikman and Ahre'n, 2009). In contrast, GSIS stimulation has been reported only at kisspeptin concentrations in the range of $10^3$ nM (i.e., 1 mM) (Bowe et al., 2012; Hauge-Evans et al., 2006), which is unusually high for a hormone.

To examine the effects of such high kisspeptin concentrations on GSIS, we treated islets with $10^3$ nM (equals 1 mM) K54 or K10 and found GSIS stimulation from both Kiss1Rfl/fl and Panc-DKiss1R islets (FIG. 11C). These findings, using selective genetic Kiss1R ablation suggest that kisspeptin at very high concentrations may stimulate GSIS in a Kiss1R-independent mechanism raising the possibility of off-target effects on GSIS of supraphysiologic kisspeptin concentrations.

Kisspeptin Suppresses Islet cAMP Synthesis and Antagonizes Incretin Hormone Glucagon-Like Peptide-1 Receptor-Mediated GSIS Potentiation. GSIS is potentiated by increased cAMP concentrations in β cells (Drucker, 2006). Kiss1R belongs to Class I/A of G protein coupled receptors and shares structural similarities with the galanin receptor, activation of which suppresses cAMP synthesis in β cells (Lee et al., 1999; Tang et al., 2012). We reasoned that kisspeptin1 may also modulate β cell cAMP levels. WT mouse islets kept at 10 mM glucose and treated with K54 (10 nM) contained lower cAMP concentrations as compared to PBS-treated islets (FIG. 4F). K54 also impaired islet cAMP production in response to the long-acting incretin hormone analog exendin-4 (E4) (FIG. 4F)—a widely used antidiabetic agent that binds and activates on β cells the receptor for the incretin hormone glucagon-like peptide-1 (GLP-1) and potentiates GSIS by stimulating β cell cAMP synthesis (Drucker, 2006). Conversely, Panc-DKiss1R islets exhibited slightly increased baseline and E4-induced cAMP concentrations, which were not affected by K54 treatment (FIG. 4F). Consistent with an antagonism between K54 and E4, respectively, on β cell function, K54 dose-dependently suppressed E4-potentiated GSIS from mouse islets cultured at 10 mM glucose (FIG. 4F, bottom). Perifusion studies of isolated mouse islets revealed that both K54 and K10 suppressed first (0-10 min after glucose stimulation) and second phases of GSIS (FIGS. 4G and 4H) as well as E4-potentiated GSIS (FIGS. 4G and 4H). KCl-induced (30 mM) depolarization of Kiss1Rfl/fl and Panc-DKiss1R islets after perifusion stimulated release of equal amounts of insulin, indicating that insulin exocytosis mechanisms distal to the regulatory β cell ATP-dependent potassium channel (KATP channel) are not impaired in Panc-DKiss1R islets (FIG. 4G).

These observations indicate that kisspeptin1 reduces β cell cAMP production and renders β cells resistant to incretin action on cAMP synthesis and GSIS potentiation.

Mouse Models of Impaired GT and DM Exhibit Increased Liver Kisspeptin1 Production. We next examined the relevance of glucagon and kisspeptin1 production in the context of DM. Mice receiving for 8 weeks a HFD developed glucose intolerance and insulin resistance as compared to standard diet (SD)-fed controls (FIGS. 12A and 12B) and, importantly, exhibited increased plasma glucagon levels in the fed state (FIG. 12C) and an increase in liver Kiss1 expression (FIG. 5A).

In the hypothalamus, Kiss1 expression is modulated by leptin signaling (Smith et al., 2006). Furthermore, leptin inhibits GSIS via its receptor on β cells (Kieffer et al., 1997). Therefore, to elucidate the relevance of hyperglucagonemia on liver Kiss1 and GSIS independent of leptin effects, we also examined mice homozygous for the inactivating leptin receptor db mutation ($Lepr^{db/db}$ mice).

$Lepr^{db/db}$ as compared to WT mice exhibited hyperglucagonemia in the fed state (FIG. 12D) and significantly increased liver Kiss1 expression (FIG. 5A). Both plasma glucagon and liver Kiss1 mRNA levels were greater in magnitude in $Lepr^{db/db}$ as compared to those found in HFD mice. Accordingly, kisspeptin1 immunoreactivity was detectable at low levels in liver of SD mice and was increased both in HFD and in $Lepr^{db/db}$ liver tissue (FIG. 5A). Both HFD-fed mice and $Lepr^{db/db}$ liver tissue showed higher CREB phosphorylation (FIG. 12F) and in vivo CREB occupancy on both CRE half-sites within the Kiss1 promoter (FIG. 12G).

Plasma from HFD-fed and diabetic $Lepr^{db/db}$ mice-as compared to SD fed WT mice-exhibited higher kisspeptin1 concentrations as determined by ELISA (FIG. 5B). Kiss1Rfl/fl islets cultured in serum-free media conditioned with plasma from HFD or from $Lepr^{db/db}$ mice exhibited impaired GSIS. In contrast, Panc-DKiss1R islets resisted GSIS inhibition by plasma of HFD or $Lepr^{db/db}$ mice. GSIS suppression from WT islets cultured in serum-free media conditioned with HFD or $Lepr^{db/db}$ plasma (FIG. 5C)—when compared with GSIS suppression by synthetic K54 (FIG. 4H)—indicated that the functional plasma kisspeptin concentrations in HFD and $Lepr^{db/db}$ mice to be equivalent to 0.5-1 nM and 7-10 nM of K10, respectively.

We further examined the relevance of liver kisspeptin in the context of human T2DM. Kisspeptin1 immunoreactivity was detectable at variable intensity by immunoblot of liver samples from humans with T2DM but not from nondiabetic humans (FIG. 5D). Accordingly, circulating kisspeptin1 immunoreactivity was increased in serum from humans with T2DM, as compared to nondiabetic individuals (FIG. 5E). Media conditioned with serum from T2DM, but not from nondiabetic, individuals suppressed GSIS from Kiss1Rfl/fl but not from Panc-DKiss1R islets (FIG. 5F). These observations indicate that—akin to rodent models of DM-in human T2DM liver kisspeptin1 expression is increased and that circulating kisspeptin suppresses GSIS.

Liver Kiss1 Upregulation is Linked to Hyperglucagonemia in DM. We determined whether hyperglucagonemia is linked to liver kisspeptin production in HFD and $Lepr^{db/db}$ mice by administering a single dose of the selective Gcgr antagonist (GAI) or an inactive analog (GAC) (Qureshi et al., 20 μM) 60 min before an ipGTT. GAI-treated as compared to GAC-treated (FIGS. 6F-6M) mice exhibited improved basal glycemia as well as GT. GAI treatment led to a reduction in liver gluconeogenic gene (FIGS. 6C-6I) and in Kiss1 expression (FIGS. 6D-6J) and to corresponding reductions in liver pCREB (FIGS. 6B-6H) and CREB occupancy of CRE 1 and 2 in the Kiss1 promoter (FIGS. 6E-6K). Circulating plasma glucagon levels remained unchanged after GAI or GAC treatment in both HFD fed (FIG. 6A) and $Lepr^{db/db}$ mice (FIG. 6G), respectively.

Thus, in the context of glucose intolerance and DM, hyperglucagonemia significantly contributes to hepatic kisspeptin1 production. Further, as demonstrated in $Lepr^{db/db}$ mice, hepatic Kiss1 regulation occurs independently of leptin.

Liver Kisspeptin1 Knockdown in Diabetic Mice Ameliorates GSIS and GT. We next examined the contribution in DM of hepatic kisspeptin1 toward impaired GSIS by liver-selective shRNA-mediated Kiss1 knockdown. Adv-Kiss1 but not -scr shRNA treatment in HFD or $Lepr^{db/db}$ mice (5-6 weeks of age), respectively, reduced within 3 days liver kisseptin1 production (FIGS. 7A-7H) and Kiss1 mRNA (FIGS. 7B-7I) as well as plasma kisspeptin1 (FIGS. 7C-7J). Plasma glucagon (FIGS. 7D-7K), liver pCREB (FIG. 7A,H), and liver CREB occupancy on Kiss1 promoter CRE sites (FIGS. 13A-13C) remained similar in Adv-Kiss1 and Adv-scr-shRNA-treated littermates. Liver kisspeptin1 knockdown in both HFD and $Lepr^{db/db}$ mice resulted in improved in vivo GT (FIGS. 7E-7M) and increased GSIS (FIGS. 7F-7N). Caloric intake (FIGS. 7E-7K), body weight (FIGS. 13B-13D), and insulin tolerance (FIGS. 7G-7O) were not different in Adv-Kiss1 and Adv-scr-shRNA-treated counterparts, ruling out changes in insulin sensitivity after Kiss1 knockdown as a mechanism for improvements in GSIS and GT.

These observations indicate that in DM, liver kisspeptin1 negatively impacts GSIS, which can be derepressed by inhibiting hepatic kisspeptin1 production.

Selective Pancreas Kiss1R Ablation Ameliorates Insulin Secretion and GT in HFD Mice. To directly assess the relevance of kisspeptin-Kiss1R signaling on GSIS in the context of DM, we examined the effects of conditional pancreas Kiss1R ablation in HFD fed mice. Kiss1Rfl/fl and Panc-DKiss1R mice, placed on a HFD for 8 weeks, exhibited similar weight gain (FIG. 14). Liver kisspeptin1 immunoreactivity, plasma kisspeptin, and glucagon levels were similar in HFD mice independent of pancreas Kiss1R status (FIG. 14). Importantly, Panc-DKiss1R showed, as compared to Kiss1Rfl/fl littermates, slightly lower fasting blood glucose and improved GT (FIG. 14). HFD-fed Panc-DKiss1R showed, relative to controls, both increased fasting insulin and in vivo GSIS. No differences were found in insulin tolerance, islet, β cell or a cell mass, or pancreas insulin content between Panc-DKiss1R and Kiss1Rfl/fl littermates (FIG. 14), excluding changes in peripheral insulin action or β cell mass to account for improved GSIS and GT in HFD-fed Panc-DKiss1R mice.

DISCUSSION

The present findings using genetically defined mouse models suggest a trihormonal regulatory circuit between pancreatic α cells, hepatocytes, and β cells and assign kisspeptin1 an unexpected role in liver to islet endocrine signaling. In addition, the findings indicate in T2DM a sequential link between hyperglucagonemia and impaired β cell function via liver-derived kisspeptin1.

Figure 2:
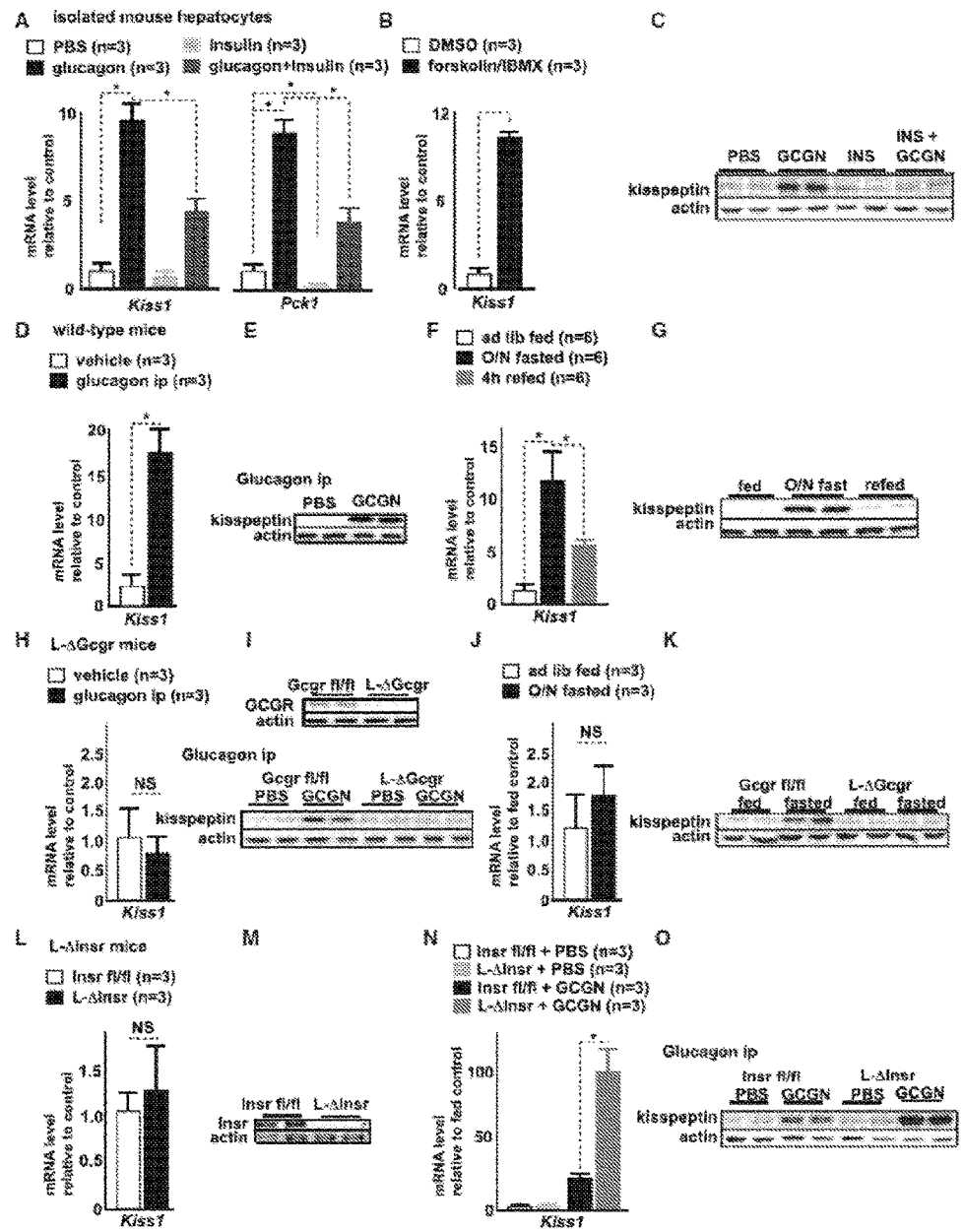
FIG. 2. Glucagon and Insulin Counterregulate Liver Kiss1 Expression (A) qRT-PCR of Kiss1 and Pck1 in isolated mouse hepatocytes exposed to indicated treatment. Glucagon stimulates and insulin suppresses both genes (mean±SEM; *p<0.05). (B) qRT-PCR of Kiss1 in isolated mouse hepatocytes exposed to vehicle (DMSO) or fsk/IBMX. cAMP stimulation stimulates Kiss1 expression (mean±SEM; *p<0.05). (C) Representative IB of cultured mouse hepatocytes after treatment with PBS, glucagon, insulin, or INS plus GCGN. Glucagon stimulates kisspeptin; insulin treatment has little effect on already low kisspeptin. Insulin counterregulates glucagon stimulation of kisspeptin. (D) qRT-PCR of Kiss1 in liver tissue of WT mice after in vivo ip treatment with vehicle (PBS) or glucagon. Glucagon treatment stimulates Kiss1 in liver (mean±SEM; *p<0.05). (E) Representative liver IB in WT mice after in vivo ip treatment with PBS or glucagon. Glucagon increases liver kisspeptin1 (mean±SEM; *p<0.05). (F) qRT-PCR of Kiss1 in liver of ad-lib-fed, O/N-fasted, and refed WT mice. Fasting stimulates liver Kiss1 expression; refeeding suppresses elevated Kiss1 (mean±SEM; *p<0.05). (G) Liver IB from ad-lib-fed, O/N-fasted, and refed WT mice. Fasting stimulates liver kisspeptin1. (H) qRT-PCR of Kiss1 in liver of L-ΔGcgr mice after ip PBS or glucagon. Glucagon does to stimulate Kiss1 in L-ΔGcgr mice (mean±SEM; *p<0.05). (I) (Top) Representative liver IB from Gcgrfl/fl and L-ΔGcgr mice. L-ΔGcgr lack GCGR. (Bottom) Liver IB from Gcgrfl/fl and L-ΔGcgr mice after ip treatment with PBS or glucagon. Baseline kisspeptin1 is similar in Gcgrfl/fl and L-ΔGcgr mouse liver. Glucagon treatment stimulates kisspeptin1 in Gcgrfl/fl but not in L-ΔGcgr mice. (J) qRT-PCR of Kiss1 in liver of ad lib fed and O/N fasted L-ΔGcgr mice. O/N fast does not stimulate Kiss1 in L-ΔGcgr mouse liver (mean±SEM; *p<0.05). (K) Representative liver IB from ad-lib-fed and O/N-fasted Gcgrfl/fl and L-ΔGcgr mice. Baseline kisspeptin1 is similar in Gcgrfl/fl and L-ΔGcgr livers. Fasting stimulates kisspeptin1 in Gcgr fl/fl but not in L-ΔGcgr liver. (L) qRT-PCR of Kiss1 in liver of Insrfl/fl and L-ΔInsr mice. Liver Insr ablation does not affect Kiss1 expression (mean±SEM; *p<0.05). (M) Representative liver IB of Insrfl/fl and L-ΔInsr mice. L-ΔInsr liver lacks insulin receptor immunoreactivity. (N) qRT-PCR of Kiss1 in liver of Insrfl/fl and L-ΔInsr mice after ip treatment with vehicle PBS or glucagon. Glucagon stimulates Kiss1 in Insrfl/fl mice and more so in L-ΔInsr liver (mean±SEM; *p<0.05). (O) Representative liver IB of Insrfl/fl and L-ΔInsr mice after ip PBS or glucagon. Glucagon stimulates stronger liver kisspeptin1 production in L-ΔInsr than in Insrfl/fl liver.
Figure 4:
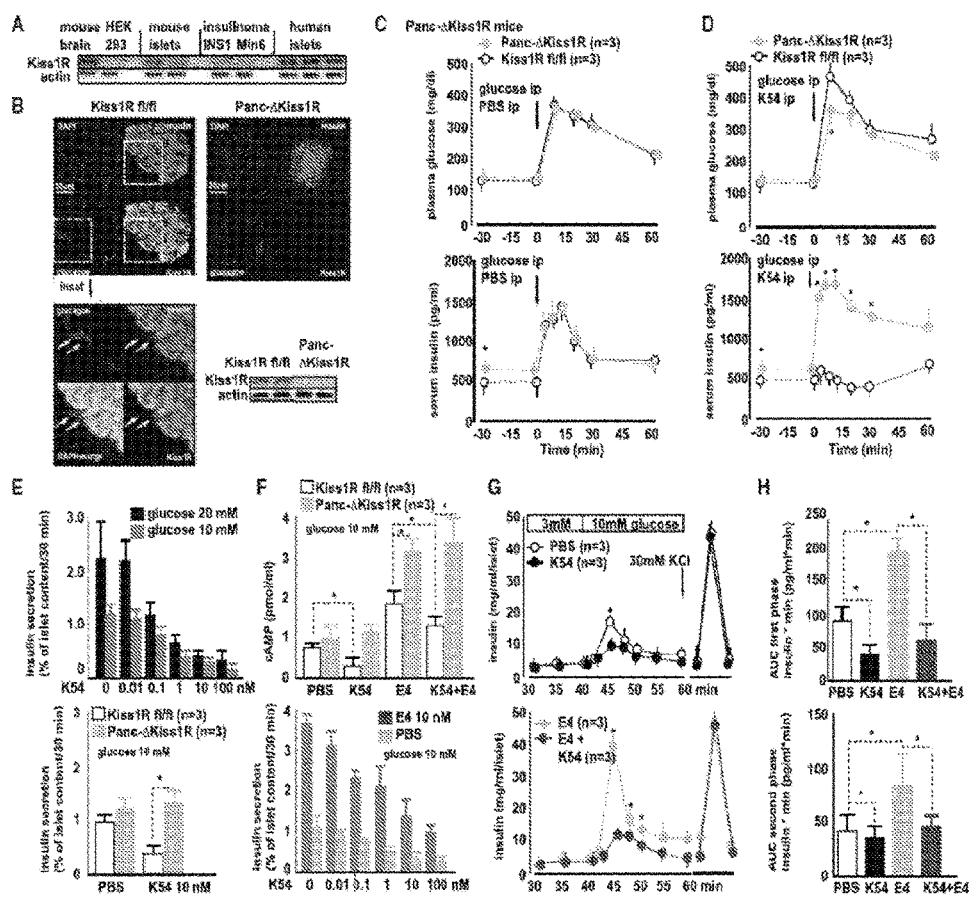
FIG. 4. Kisspeptin1 at Nanomolar Concentrations Inhibits GSIS in a Kiss1R-Dependent Manner (A) Representative IB for Kiss1R mouse brain, HEK293T cells, mouse islets, INS1 rat insulinoma cells, Min6 mouse insulinoma cells, and human islets. Mouse brain, mouse islets, insulinoma cells, and human islets express Kiss1R. HEK293T cells do not express Kiss1R. (B) (Left) Immunohistochemistry for insulin, glucagon, and Kiss1R in pancreas from Kiss1Rfl/fl mice. Kiss1R immunoreactivity colocalizes with insulin-positive β cells but not with glucagon-positive α cells. Showing 203 magnification. Pseudocoloring is as follows: red for glucagon, green for insulin, yellow for Kiss1R, and blue for nucleus counterstain with DAPI (left bottom) inset of previous image at 403 magnification. (Right top) Immunohistochemistry for insulin, glucagon, and Kiss1R in pancreas from Panc-DKiss1R mice. Kiss1R immunoreactivity is lacking in Panc-DKiss1R islet. (Right bottom) Representative islet IB from Kiss1Rfl/fl and Panc-DKiss1R mice. Kiss1R is absent in Panc-DKiss1R islets. (C) ipGTT in Kiss1Rfl/fl and Panc-DKiss1R mice during ip coinjection of PBS and glucose. (Top) GT is similar in Kiss1Rfl/fl and Panc-DKiss1R mice. (Bottom) Baseline fasting glucose is slightly elevated in Panc-DKiss1R mice as compared to Kiss1Rfl/fl littermates. In vivo GSIS is similar in Kiss1Rfl/fl and Panc-DKiss1R mice (mean±SEM; *p<0.05). (D) ipGTT in Kiss1Rfl/fl and Panc-DKiss1R mice during ip coinjection of 10 nM K54 and glucose. K54 impairs GT (top) and GSIS (bottom) in Kiss1Rfl/fl but not in Panc-DKiss1R mice (mean±SEM; *p<0.05). (E) (Top) Dose response curve of K54 and K10 inhibition of GSIS from WT mouse islets during static at 10 or 20 mM glucose. Both K54 and K10 inhibit GSIS in a dose-dependent manner from 0 to 100 nM at both 10 and 20 mM glucose; (bottom) GSIS from Kiss1R fl/fl and Panc-DKiss1R islets treated with PBS K10 or K54. K10 or K54 (both 10 nM) inhibit GSIS from Kiss1R fl/fl but not from Panc-DKiss1R islets. (F) cAMP synthesis and GSIS in response to K54 and to incretin analog exendin-4 (E4) in Kiss1R fl/fl and Panc-DKiss1R islets. (Top) K54 impairs cAMP synthesis in Kiss1Rfl/fl but not in Panc-DKiss1R islets. E4 stimulates cAMP synthesis similarly in both Kiss1Rfl/fl and in Panc-DKiss1R islets. K10 reduces E4-stimulated cAMP levels in Kiss1Rfl/fl but not in Panc-DKiss1R islets. (Bottom) During static incubation of mouse islets, K54 impairs GSIS and also E4 potentiation of GSIS from islets in a dose-dependent manner (mean±SEM; *p<0.05). (G) Islet perifusion assay in WT islets in response to K54 and to E4. (Top) K54 impairs both first and second phases of GSIS and (bottom) E4-potentiated first and second phase GSIS; end of perifusion shows similar insulin release upon KCL induced depolarization (mean±SEM; *p<0.05). (H) Area under the curve (AUC) of (top) first and (bottom) second phase GSIS from WT mouse islets treated with PBS, K54, E4, or K54+E4. K54 inhibits both first and second phases of GSIS and E4 potentiated GSIS (mean±SEM; *p<0.05).

Hyperglucagonemia, which occurs early during development of T2DM, upregulates kisspeptin1 production by the liver (FIG. 2). Kisspeptin1 in turn functions as a hormone to suppress GSIS (FIG. 4). Thus, in T2DM the β cell is exposed to two counteracting stimuli elicited by glucagon action on the liver. Glucagon-induced HGP and hyperglycemia stimulate, whereas kisspeptin1 production inhibits, GSIS.

The physiologic relevance of opposing actions of hepatic cAMP-CREB signaling on β cell function remains to be fully explored. Teleological considerations render plausible a survival mechanism in that hepatic cAMP-CREB-induced kisspeptin1 serves as a (among other mechanisms) safeguard against insulin secretion and hypoglycemia during fight and flight reactions, should these occur during and interrupt prandial nutrient absorption-when insulin secretion otherwise would be elevated. To this end, it is likely that epinephrine, another fight and flight mediator, which activates liver cAMP signaling (Sherline et al., 1972), may also participate in liver Kiss1 regulation.

Figure 3:
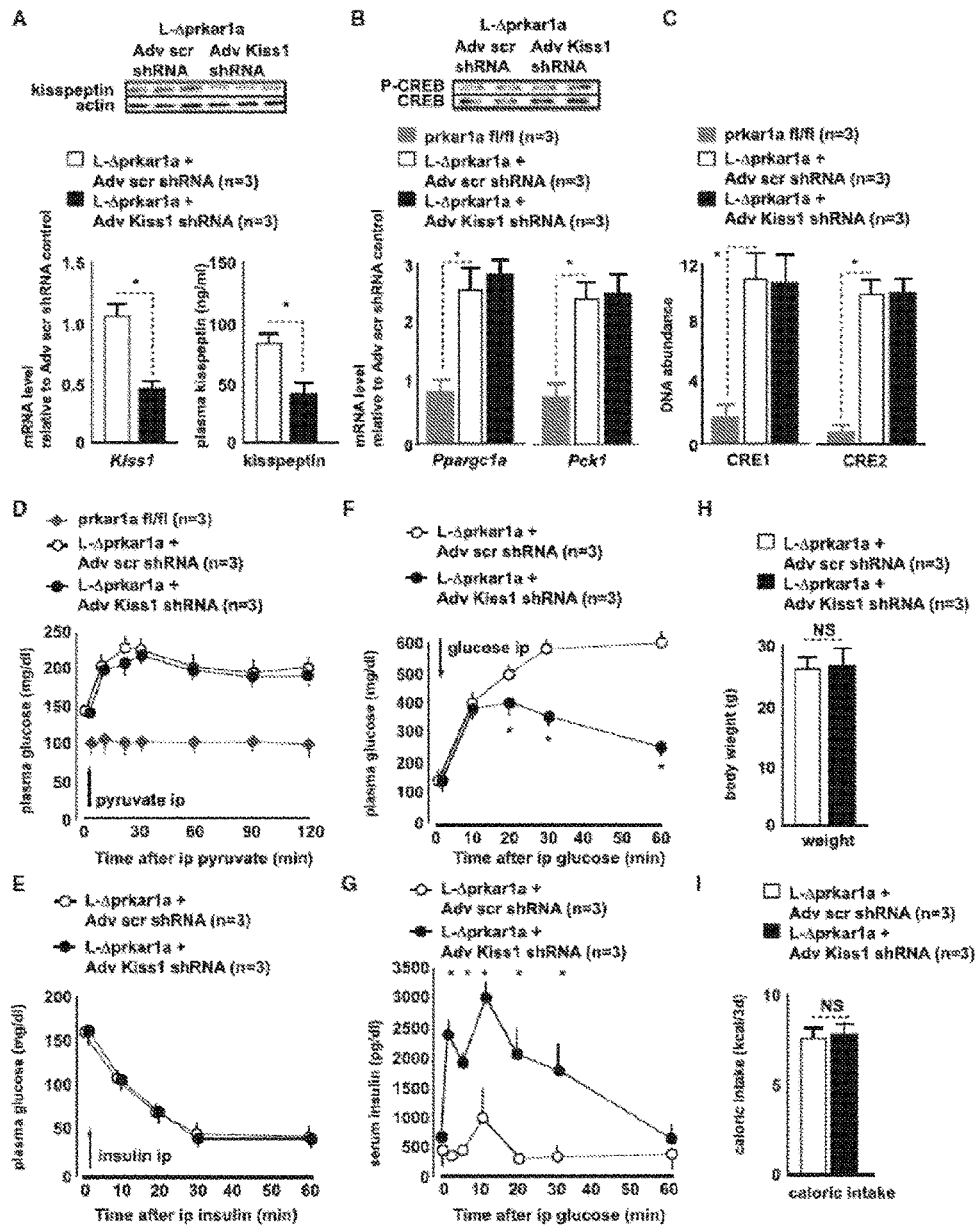
FIG. 3. In L-Δprkar1a Mice Liver Kiss1 Knockdown Derepresses GSIS and Ameliorates Glucose Tolerance despite Continued Upregulated Gluconeogenesis (A) (Top) Liver kisspeptin1 IB, (bottom left) liver qRT-PCR of Kiss1 mRNA, and (bottom right) plasma kisspeptin1 in L-Δprkar1a mice 3 days after Adv-scr or Adv-Kiss1 shRNA treatment. Liver kisspeptin1 protein, Kiss1 mRNA, and plasma kisspeptin1 are reduced after Kiss1 Kiss1 L-Δprkar1a mice (mean±SEM; *p<0.05). (B) (Top) pCREB and total CREB IB. (Bottom) qRT-PCR of Ppargc1a and Pck1 in liver of L-Δprkar1a mice 3 days after Adv-scr shRNA or Adv-Kiss1 shRNA treatment. CREB phosphorylation and total CREB protein are unaffected by Kiss1 knockdown in L-Δprkar1a liver. Ppargc1a and Pck1 mRNA levels are upregulated in L-Δprkar1a as compared to prkar1afl/fl livers and are unaffected by liver Kiss1 knockdown in L-Δprkar1a mice (mean±SEM; *p<0.05). (C) In vivo chromatin immunoprecipitation (ChIP) of CREB occupancy on CRE1 and CRE2 within the Kiss1 promoter in liver samples. CREB occupancy on Kiss1 CRE1 and CRE2 in L-Δprkar1a liver is increased as compared to prkar1afl/fl liver and unaffected by Kiss1 knockdown in L-Δprkar1a mice (mean±SEM; *p<0.05). (D) ip PCT in fed prkar1afl/fl and L-Δprkar1a mice 3 days after Adv-scr or Adv-Kiss1 shRNA treatment. Gluconeogensis activity is increased in L-Δprkar1a as compared to prkar1afl/fl mice. Gluconeogenesis activity in L-Δprkar1a mice is unaffected by Kiss1 knockdown (mean±SEM; *p<0.05). (E) ip ITT in L-Δprkar1a mice 3 days after treatment with Adv-scr or Adv-Kiss1 shRNA. Peripheral insulin sensitivity in L-Δprkar1a mice is unaffected by Kiss1 knockdown (mean±SEM; *p<0.05). (F) ipGTT in L-Δprkar1a mice 3 days after treatment with Adv-scr or Adv-Kiss1 shRNA. L-Δprkar1a mice with Kiss1 knockdown show improved GT as compared to controls (mean±SEM; *p<0.05). (G) Serum insulin during ipGTT in L-Δprkar1a mice 3 days after treatment with Adv-scr or Adv-Kiss1 shRNA. GSIS is augmented in L-Δprkar1a mice after liver Kiss1 knockdown as compared to controls (mean±SEM; *p<0.05). (H) Body weight in L-Δprkar1a mice 3 days after treatment with Adv-scr or Adv-Kiss1 shRNA. Body weight in L-Δprkar1a mice is unaffected by Kiss1 knockdown. (I) Caloric intake in L-Δprkar1a mice during 3 days after treatment with Adv-scr or Adv-Kiss1 shRNA. Caloric intake in L-Δprkar1a mice is unaffected by Kiss1 knockdown.

It is important to note that our studies using genetically defined Kiss1R-deficient islets reveal that kisspeptin applied at supraphysiologic doses in the micromolar range stimulates GSIS, likely due to effects which are not mediated by the bona-fide Kiss1R (FIG. 11C). This observation of Kiss1R-independent effects at high doses of kisspeptin, which are unusually high for a hormone, may in part explain the contradictory observations on GSIS between physiologic and supraphysiologic kisspeptin1 concentrations (Bowe et al., 2012; Hauge-Evans et al., 2006; Silvestre et al., 2008; Vikman and Ahre' n, 2009). Our studies suggest that Kiss1R signaling in β cells suppresses cAMP and inhibits GSIS. An intravenous bolus K10 in the nonhuman primate *Macaca mulatta* is reported to stimulate GSIS, albeit circulating kisspeptin concentrations were not measured in that study (Wahab et al., 2011). Based on the studies herein, humans with T2DM exhibit increased liver kisspeptin1 immunoreactivity and increased circulating kisspeptin, and their plasma suppresses GSIS from mouse islets in a Kiss1R-dependent manner (FIGS. 3 and 4). Future studies on the interplay between glucagon and kisspeptin1 in humans will need to carefully examine the dose response of kisspeptin1 on GSIS combined with reliable measurements of circulating functional kisspeptin1 isoforms.

Our observations further suggest that in T2DM GSIS is insufficient to overcome the coexisting inhibition on β cells exerted by kisspeptin1. This mechanism results in inadequate insulin secretion to meet metabolic demands and aggravates β cell dysfunction and hyperglycemia. Clinical observations indicate that in T2DM, although incretin GLP-1 is normally secreted, endogenous GLP-1 is insufficient to achieve physiologic GSIS potentiation. Furthermore, treatment with dipeptidyl-peptidase IV inhibitors, which inhibit GLP-1 degradation and increase endogenous GLP-1 concentrations by 2-fold, or treatment with long-acting GLP-1 analog E4 restore β cell function in T2DM. These observations have led to the concept of reduced GLP-1 sensitivity of β cells in T2DM (Meier and Nauck, 2008). Antagonism by K54 on E4-induced GSIS potentiation (FIGS. 4E and 4F) suggests that increased circulating kisspeptin1 levels in T2DM may at least in part contribute to the diminished response to endogenous GLP-1 in T2DM subjects.

Thus, our findings uncover the liver as a site of regulated kisspeptin production and provide mechanistic and causal underpinnings for the following common observations made in clinical T2DM: (a) relative hyperglucagonemia, (b) insufficient insulin secretion to regulate glycemia, and (c) diminished response to endogenously secreted GLP-1 and restoration of β cell function by pharmacologic GLP-1 receptor agonism.

In a broader context, neutralizing circulating kisspeptin1 or antagonism of Kiss1R on β cells are appealing avenues to augment GSIS and improve glucose homeostasis in T2DM. In this regard, Kiss1R antagonists, which would not cross the blood-brain barrier and interfere with hypothalamic reproductive functions of kisspeptin1, would be particularly advantageous. Another important aspect is that plasma kisspeptin1 activity may serve as a biomarker to identify T2DM patients who would benefit most from aggressive b-cell-targeted therapy.

Ongoing Efforts to Understand T2DM Pathogenesis.

Both pancreatic β-cell dysfunction and hyperglucagonemia are hallmarks of type 2 diabetes mellitus (T2DM). However, the mechanistic relationship between hyperglucagonemia and β-cell dysfunction is poorly understood. Early in the pathogenesis of T2DM, glucagon levels are abnormally elevated, and while glucagon levels are normally suppressed after a meal intake, individuals with T2DM lack postprandial glucagon suppression or exhibit an increase in glucagon levels. In addition, activating glucagon-PKA signaling in vivo in liver results in impaired glucose stimulated insulin secretion (GSIS). Furthermore, β-cells-responding to increased metabolic demand in T2DM (insulin resistance, hyperglycemia)-increase insulin synthesis and secretion. Increased protein synthesis, elicits cellular endoplasmic stress (ERS) and unfolded protein response (UPR) which, when unresolved, activate the NLRP3 inflammasome and initiate β-cell apoptosis.

The present inventors seek to further understand of T2DM pathogenesis. In particular, present inventors aim to examine further the role of the newly discovered liver-derived hormone kisspeptin1 in causing β cell dysfunction as well as inducing B cell ERS/UPR and potential loss of β-cell mass.

To examine the role of hepatic glucagon receptor-cAMP-PKA signaling in β-cell dysfunction, we inducibly disinhibited cAMP-PKA signaling in vivo in adult mouse liver by ablating liver PKA regulatory subunit 1A (prkar1a) (L-Δprkar1a mice). Upregulation of hepatic PKA signaling resulted in increased hepatic gluconeogenesis, hyperglycemia but suppressed GSIS. Conversely, identical hyperglycemia achieved by continuous exogenous glucose infusion (D-glucose mice) was associated with increased GSIS. Differential hepatic gene expression analysis identified the gene encoding the neuropeptide kisspeptin1 (Kiss1) and its protein product to be markedly elevated in L-Δprkar1a but not in control or in D-glucose liver and plasma. In addition, T2DM mouse models with hyperglucagonemia: diet induced obese and glucose intolerant (DIO) and $Lepr^{db/db}$ diabetic mice also exhibited increased hepatic Kiss1 mRNA and liver and plasma kisspeptin1. Treatment with glucagon of isolated mouse hepatocytes stimulated Kiss1 mRNA and protein product. We detected the kisspeptin receptor Kiss1R at high levels in mouse pancreatic β-cells. In vivo administration of synthetic kisspeptin suppressed GSIS in WT mice but not in mice lacking pancreas Kiss1R. Acute shRNA-mediated liver Kiss1 knockdown improved glucose tolerance in DIO and $Lepr^{db/db}$ mice owing to increased GSIS. Kisspeptin reduced GSIS and cAMP production in isolated cultured wild-type (WT) mouse islets but not in Kiss1R ablated islets. In addition, prolonged (48 h) in vitro treatment of WT islets with kisspeptin potently increased markers of endoplasmic reticulum stress (ERS) and unfolded protein response (UPR) even at normoglycemia (5 mM glucose), suggesting a mechanism of provoking ER stress and UPR in β-cells independent of increased pro-insulin biosynthesis in response to hyperglycemia or insulin resistance.

In certain embodiments, without being limited hereto, we propose a novel endocrine hepato-pancreatic regulatory mechanism of pancreatic β-cell function. Hyperglucagonemia in T2DM induces not only hepatic gluconeogenesis but also synthesis and secretion of kisspeptin1. Glucose stimulates, while kisspeptin1 inhibits GSIS. Further, we propose that kisspeptin1 not only impairs GSIS but also induces ERS and UPR in β-cells independently of increased β-cell demand on pro-insulin biosynthesis. We now propose to address conduct the following:

To test the hypothesis that kisspeptin1 suppresses GSIS by interaction via its receptor Kiss1R on β-cells, we examine whether Kiss1 ablation ameliorates impaired GSIS in L-Δprkar1a, DIO and Lepr$^{db/db}$ mice; whether β-cell selective Kiss1R ablation ameliorates GSIS and glucose tolerance in L-Δprkar1a, DIO and Lepr$^{db/db}$ mice; whether kisspeptin1 alters β-cell response (GSIS potentiation and/or proliferation) to incretin hormones glucagon-like peptide-1 (GLP-1) and to glucose-dependent insulinotropic peptide (GIP); and whether kisspeptin1 modulates glucagon secretion via Kiss1R on α-cells.

To test the hypothesis that kisspeptin1 action on islets in vitro and in vivo in mice induces in β-cells endoplasmic reticulum stress (ERS) and an unfolded protein response (UPR), we examine: whether effectors of the UPR are upregulated by kisspeptin1 action on β-cells and whether the untoward UPR consequences of inflammation and apoptosis markers are increased by kisspeptin1; whether β-cell Kiss1R ablation in DIO and Lepr$^{db/db}$ mice will protect them from ERS, UPR and β-cell dysfunction and apoptosis, and whether mice lacking the UPR mediators TXNIP or CHOP (or their isolated islets) are protected from ERS/UPR and β-cell apoptosis induced by kisspeptin1.

To test the hypothesis that circulating kisspeptin1 is elevated in human T2DM, that kisspeptin1 impairs GSIS and response to incretins, and/or induces ERS/UPR in human islets, we examine kisspeptin1, insulin, glucagon levels in the post-absorptive state and during an oral glucose tolerance test in humans with and without T2DM; whether Kiss1R is present on human pancreatic endocrine cells and its co-localization with insulin or other hormones, C) the interplay of kisspeptin1 and GLP-1 or GIP receptor activation on cAMP synthesis and GSIS potentiation in human islets, and D) whether kisspeptin1 impairs GSIS and induces ERS/UPR in isolated and cultured human islets.

As described herein, we have inducibly disinhibited cAMP-PKA signaling in vivo in adult mouse liver by ablating hepatic protein kinase A regulatory subunit 1A (prkar1a) by adenovirus mediated hepatic CRE recombinase transduction in floxed prkar1a mice (L-Δprkar1a mice)23. Control animals were treated with an adenovirus expressing GFP (=prkar1a fl/fl) (FIG. 3A). To exclude effects secondary to CRE overexpression in liver, we also treated Rosa26-Stoplox EGFP mice with Adv-CRE as additional controls (=R26-stp-EGFP). Adv-CRE ablated prkar1a in liver tissue but not in skeletal muscle, islet, adipose tissue or hypothalamus (FIG. 3B).

Figure 17:
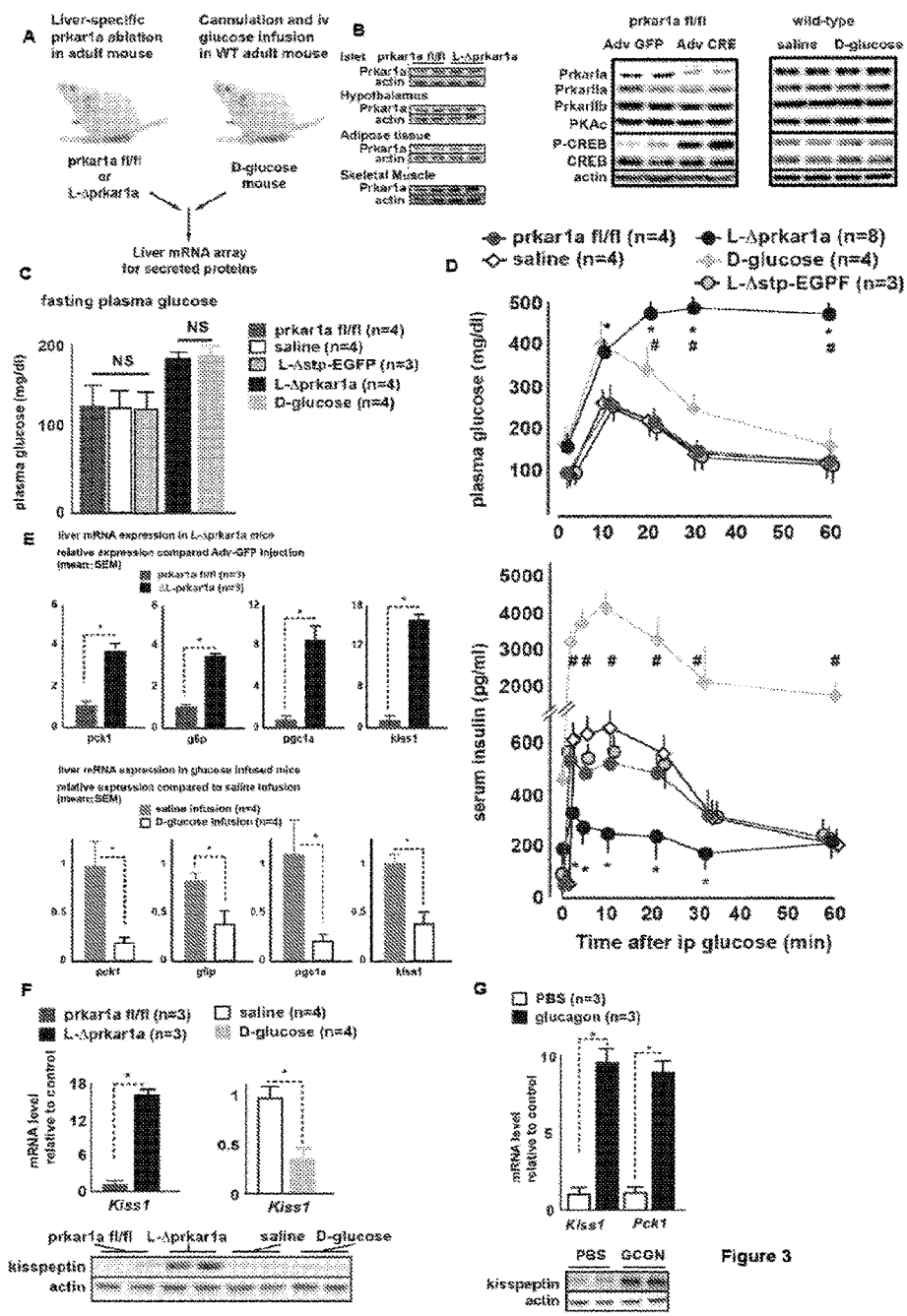

Upregulation of hepatic cAMP-PKA signaling within 3 days stimulated hepatic gluconeogenesis causing increase in fasting glucose levels and insufficient insulin secretion to correct glycemia (FIG. 17C,D). Both control groups showed little change in their glucose homeostasis, excluding CRE-mediated artifacts or "inflammation" effects secondary to adenovirus treatment as reasons for altered liver function (FIG. 3D). Conversely, identical baseline fasting glycemia achieved in mice by continuous exogenous glucose infusion for 3 days 24 (D-glucose mice) (FIG. 3D) was associated with increased insulin secretion and relatively mild impairment of glucose tolerance despite continued exogenous glucose infusions (FIG. 3C). Differential hepatic gene expression analysis between these two mouse models identified the gene encoding the neuropeptide kisspeptin-1 (Kiss1) to be markedly elevated in L-Δprkar1a but not in D-glucose mice (FIG. 3E).

Figure 18:
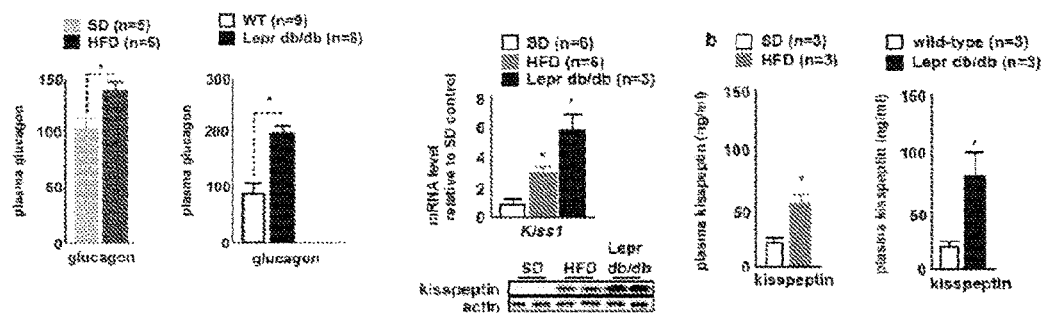

Glucagon treatment of isolated WT mouse hepatocytes increased kisspeptin mRNA and protein, confirming that glucagon directly regulates kisspeptin synthesis in hepatocytes (FIG. 17F). Mouse models of glucose intolerance and T2DM: DIO and Lepr$^{db/db}$ mice exhibited hyperglucagonemia (FIG. 4, left), increased hepatic Kiss1 gene expression (FIG. 4 middle) as well as circulating kisspeptin levels (FIG. 18 right). In DIO mice low amounts of Kiss1 transcript was detectable in adipose tissue, but were completely absent in Lepr$^{db/db}$ adipose tissue (not shown).

Figure 5:
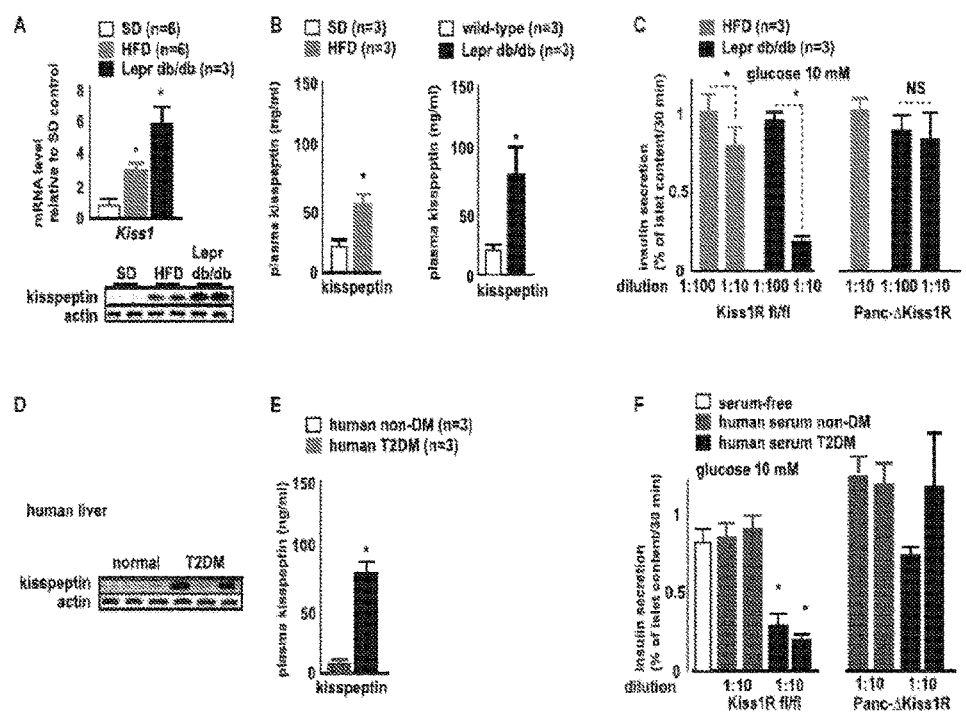
FIG. 5. Liver Kisspeptin1 Expression and Plasma Kisspeptin Levels Are Elevated in Mouse Models of DM and in Humans with T2DM (A) (Top) qRT-PCR for Kiss1 in liver tissue and (bottom) liver IB for kisspeptin1 in SD, HFD-fed, and Lepr$^{db/db}$ mice. Both Kiss1 mRNA and kisspepetin1 protein are increased in HFD-fed mice and found at higher levels in $^{db/db}$ mouse livers (mean±SEM; *p<0.05). (B) Plasma kisspeptin1 in SD, HFD-fed, and Lepr$^{db/db}$ mice. Plasma kisspeptin1 is increased in (left) HFD fed and (right) in Lepr$^{db/db}$ mice as compared to SD fed littermates (mean±SEM; *p<0.05). (C) GSIS from cultured (left) Kiss1Rfl/fl and (right) Panc-DKiss1R mouse islets in media conditioned with plasma from HFD fed and Lepr$^{db/db}$ mice. GSIS from Kiss1Rfl/fl is suppressed during culture in media conditioned with HFD fed or $^{db/db}$ plasma at 1:10 dilution but not at 1:100 dilution. GSIS from Panc-DKiss1R islets is unaffected by media conditioned with plasma of HFD fed or Lepr$^{db/db}$ mice (mean±SEM; *p<0.05). (D) Representative liver IB for kisppeptin1 in humans without DM and humans with T2DM. Humans with T2DM exhibit varying degrees of kisspeptin immunoreactivity in liver tissue. (E) Plasma kisspeptin1 in humans without DM and with T2DM. Plasma kisspeptin1 levels are elevated in humans with T2DM as compared to humans without diabetes (mean±SEM; *p<0.05). (F) GSIS from cultured (left) Kiss1Rfl/fl and (right) Panc-DKiss1R mouse islets in media conditioned with plasma from humans with T2DM and without DM. GSIS from Kiss1Rfl/fl but not from Panc-DKiss1R islets is suppressed during culture in media conditioned with T2DM plasma (mean±SEM; *p<0.05).
Figure 6:
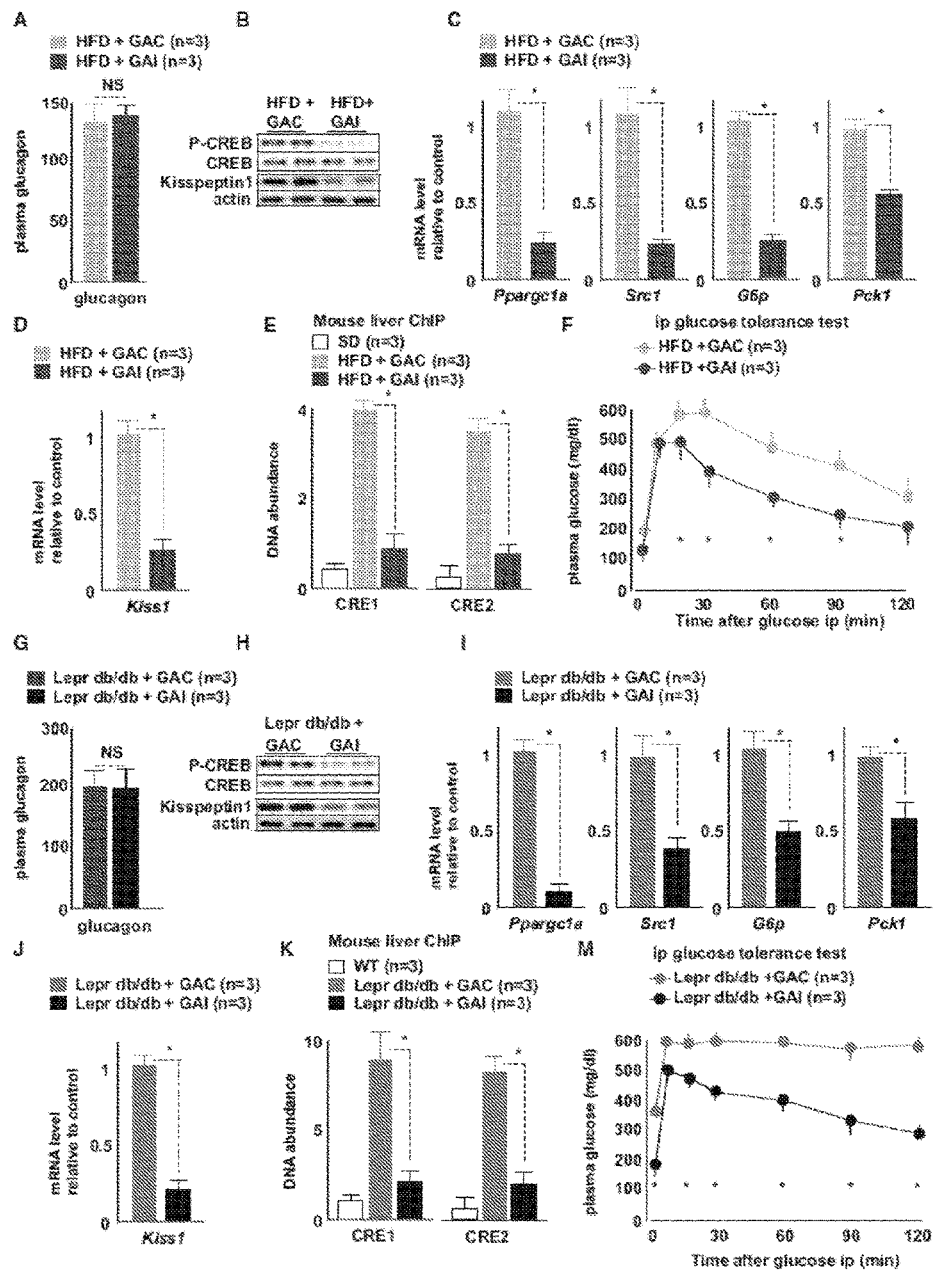
FIG. 6. Hyperlucagonemia Is Linked to Liver Kisspeptin1 Production in HFD Fed and Lepr$^{db/db}$ Mice (A-F) HFD-fed mice. (G-M) Lepr$^{db/db}$ mice. (A and G) Plasma glucagon levels in the fed state 60 min after treatment with GAI or GAC. Plasma glucagon levels remain unchanged after GAI or GAC treatment. (B and H) Representative liver IB for pCREB, total CREB and kisspeptin1 in GAI and GAC treated mice. Phospho-CREB is reduced in mice treated with GAI but not GAC. (C and I) qRT-PCR of indicated genes of the gluconeogenic program in livers of GAI- or GAC-treated mice. GAI but not GAC treatment downregulates Ppargla, Src1, G6P, and Pck1 mRNA (mean±SEM; *p<0.05). (D and J) qRT-PCR of Kiss1 in livers of GAI- and GAC-treated mice. GAI but not GAC treatment downregulates liver Kiss1 mRNA (mean±SEM; *p<0.05). (E and K) In vivo ChIP of CREB occupancy on (left) CRE1 and (right) CRE2 half-sites of the Kiss1 promoter in livers of GAI- or GAC-treated SD mice, HFD and Leprdb/db mice. GAI reduces CREB occupancy on Kiss1 CRE1 and CRE2 to levels similar to those in control mice (mean±SEM; *p<0.05). (F and L) ipGTT in GAI- or GAC-treated mice. GAI treatment improves GT as compared to GAC treatment (mean±SEM; *p<0.05).
Figure 7:
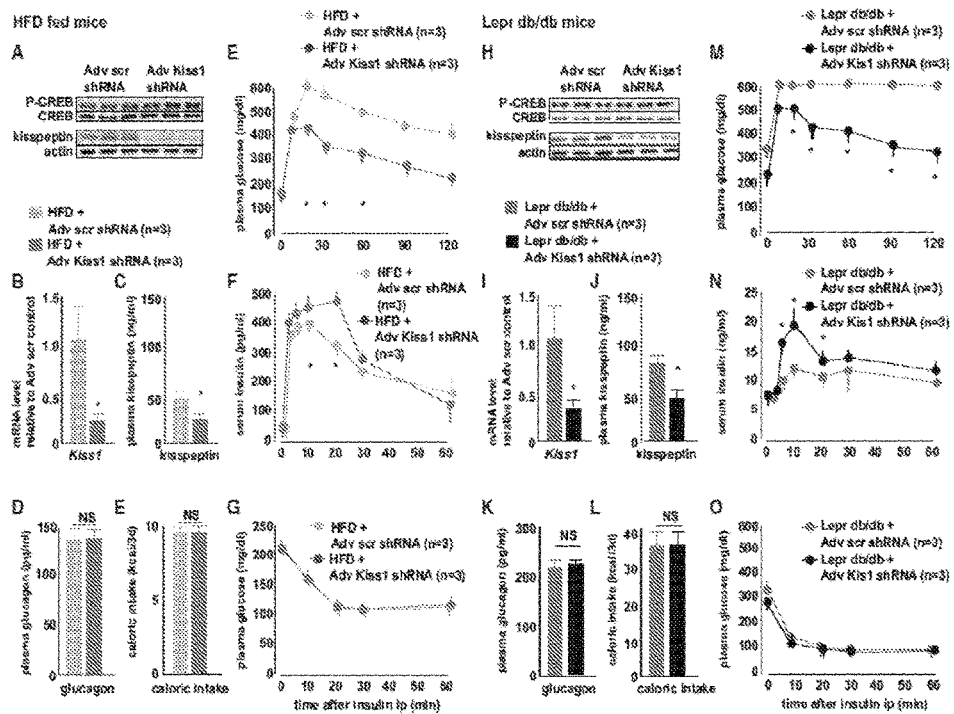
FIG. 7. Kiss1 shRNA Knockdown In Vivo in Livers of in HFD and Lepr$^{db/db}$ Mice Derepresses GSIS and Glucose Tolerance (A-G) HFD mice. (H-O) Lepr$^{db/db}$ mice. (A and H) Representative liver IB of pCREB, total CREB, and kisspeptin1 3 days after treatment with Adv-scr or Adv-Kiss1 shRNA. Liver pCREB is not affected, and liver kisspeptin1 protein is reduced by Kiss1 knockdown. (B and I) qRT-PCR of Kiss1 in livers 3 days after treatment with Adv-scr or Adv-Kiss1 shRNA. Adv-Kiss1 shRNA down-regulates liver Kiss1 mRNA levels as compared to Adv-scr shRNA treatment (mean±SEM; *p<0.05). (C and J) Plasma kisspeptin1 levels 3 days after treatment with Adv-scr or Adv-Kiss1 shRNA. Liver Kiss1 knockdown reduces plasma kisspeptin1 (mean±SEM; *p<0.05). (D and K) Plasma glucagon levels 3 days after treatment with Adv-scr or Adv-Kiss1 shRNA. Liver Kiss1 knockdown does not change plasma glucagon levels (mean±SEM). (E and L) Caloric intake in during 3 days after treatment with Adv-scr or Adv-Kiss1 shRNA. Caloric intake is unaffected by Kiss1 knockdown (mean±SEM). (E and M) ipGTT 3 days after treatment with Adv-scr or Adv-Kiss1 shRNA. GT is improved after Kiss1 knockdown (mean±SEM; *p<0.05). (F and N) GSIS during ipGTT 3 days after treatment with Adv-scr or Adv-Kiss1 shRNA. GSIS is improved after Kiss1 knockdown (mean±SEM; *p<0.05). (G and O) ip ITT 3 days after treatment with Adv-scr or Adv-Kiss1 shRNA. Insulin tolerance is not different after Kiss1 knockdown.

Moreover, immunohistochemistry combined with confocal microscopy revealed that the kisspeptin receptor Kiss1R30,36 is expressed at significant levels on β-cells but not on α-cells (FIG. 19 left). Exposure of WT islets to the biologically fully active 54 amino acid C-terminal kisspeptin fragment K54 (0-10 nM) 30,37 suppressed GSIS in a dose-dependent manner (FIG. 19 right top). And Kiss1R ablated islets resisted GSIS suppression by K54 (FIG. 5 right bottom). Moreover, WT mouse islets exhibited reduced cAMP production when treated with the Kiss1R agonist K5430,37—an effect, which was partially reversed by administering the glucagon-like peptide-1 receptor agonist exendin-4 (FIG. 20 left top). Directly testing the in vivo effects of kisspeptin on GSIS, acute K54 administration (10 nmol ip) in mice impaired glucose tolerance and suppressed GSIS in WT mice but not in mice lacking pancreas Kiss1R (FIG. 20 left bottom), which were generated by interbreeding PDX1-CRE with Kiss1Rfl/fl (=Panc-ΔKiss1R) mice. Furthermore, ablation of Kiss in pancreas ameliorates GSIS and glucose tolerance in DIO mice, while insulin tolerance is unchanged (FIG. 6 right)

Taken together, the present inventors have discovered that kisspeptin is produced in the liver in response to glucagon action, is elevated in liver and plasma of DIO glucose intolerant and Lepr$^{db/db}$ diabetic mice and when administered acutely in experimental systems, suppresses β-cell GSIS via direct action on Kiss1R, which is expressed on β-cells.

In Vivo Model of Isolated Hepatic Kisspeptin1 Production. To generate a model of chronically increased liver-specific kisspeptin1 synthesis and release, we have designed an adeno-associated virus containing albumin promoter and enhancer elements controlling mouse full-length Kiss1 cDNA expression (AAV-Alb-Kiss1). Adeno-associated virus allows long-term (up to 40 weeks) in vivo episomal expression of transduced product. To restrict kisspeptin1 expression to liver only, we inserted 400 bp of the mKiss1 cDNA flanked by albumin regulatory sequences (1 kb albumin promoter/enhancer plus a 0.9 kb 3' intronic sequence) into the AAV DJ backbone, which shows highest liver tropism. Adult male mice were treated with AAV-Alb-Kiss1 by tail vein injection, while control littermates received AAV-Alb-GFP. Two weeks after injection littermate mice did not show any obvious differences in activity or weight. AAVA1b Kiss1 exhibit increased liver kisspeptin and plasma kisspeptin concentrations to a similar range found in DIO mice, whereas AAV-Alb-GFP treated mice did not show any change as compared to control mice without AAV treatment (FIG. 21).

Kisspeptin1 Causes ERS and UPR in Islets Independently of Hyperglycemia. We found that kisspeptin reduces islet β-cell cAMP levels and also reduced cAMP stimulated by the incretin GLP-1 analog exendin4 (E4) (FIG. 20). Because reduction in cAMP signaling in β-cells reduces IRS2 and PDX1 and provokes ERS/UPR and apoptosis 11,12, we examined whether kisspeptin action on β-cells may provoke ERS/UPR. Islets were incubated in 10 nM K54. To control for stimulus for increased insulin biosynthesis and potential UPR response, we incubated islets at 5 and 10 mM glucose. After 48 hours of K54 exposure at 5 mM glucose, islets showed a reduction in IRS2 and PDX1 expression as well as increased ERS/UPR, oxidative stress and NLRP3 inflammasome (NLRP3-I) markers. Incubation at 10 mM glucose stimulated oxidative stress ERS and NLRP-I markers, but less pronounced than K54 at 5 mM glucose. Treatment with K54 at high (10 mM) glucose further augmented ERS/UPR, oxidative stress and NLRP3-I markers. Thus, kisspeptin treatment even at normoglycemia stimulates in islets the ERS/UPR response more potently than hyperglycemia (glucose 10 mM) and K54 aggravates ERS/UPR induced by hyperglycemia only (Table 5).

TABLE 5

| | Normoglycemia Glucose 5 mM | | Hyperglycemia Glucose 10 mM | |
|---|---|---|---|---|
| | PBS | K54 10 nM | PBS | K54 10 nM |
| cAMP dependent | | | | |
| IRS2 | 1.0 ± 0.3 | 0.5 ± 0.3* | 1.2 ± 0.3 | 0.6 ± 0.2*# |
| PDX1 | 1.1 ± 0.2 | 0.6 ± 0.2* | 1.1 ± 0.3 | 0.5 ± 0.3*# |
| ER stress | | | | |
| CHOP | 1.1 ± 0.2 | 1.9 ± 0.4* | 1.2 ± 0.3 | 2.2 ± 0.5*# |
| PDI | 0.9 ± 0.3 | 1.4 ± 0.4* | 1.0 ± 0.3 | 1.8 ± 0.3*# |
| Total XBP-1 | 1.1 ± 0.3 | 1.4 ± 0.3 | 1.3 ± 0.4 | 1.5 ± 0.3 |
| Spliced XBP-1 | 1.0 ± 0.3 | 1.8 ± 0.5* | 1.5 ± 0.5 | 2.1 ± 0.4*# |
| Oxidative stress | | | | |
| Catalase | 1.2 ± 0.3 | 6.2 ± 0.6* | 4.1 ± 0.4* | 8.8 ± 0.5*# |
| SOD1 | 1.1 ± 0.1 | 2.1 ± 0.4* | 1.5 ± u0.5 | 3.2 ± 0.3*# |
| SOD2 | 0.9 ± 0.4 | 1.9 ± 0.3* | 1.5 ± 0.2* | 2.4 ± 0.4*# |
| NLRP3 Inflammasome | | | | |
| TXNIP | 1.2 ± 0.2 | 4.8 ± 1.1* | 1.7 ± 0.4* | 5.5 ± 0.3*# |
| ATF5 | 0.9 ± 0.3 | 1.4 ± 0.4* | 1.2 ± 0.3 | 1.9 ± 0.4*# |
| IL-1β | 1.0 ± 0.2 | 1.7 ± 0.3* | 1.3 ± 0.2 | 1.9 ± 0.2*# |

Follow-up Experiments. All animals in studies involving Adenovirus actually received adenovirus. To ablate prkar1a, prkar1a fl/fl mice were treated with Adv-CRE. Control animals were prkar1a fl/fl mice treated with Adv-GFP (these animals were called prkar1a fl/fl in order to keep the nomenclature simple). A second group of control animals were Rosa26-stoplox EGFP mice, which received Adv-CRE. As can be seen in FIG. 3 of this application, the control mice do not show any changes in glucose homeostasis, indicating that a) the effects of prkar1a ablation are specific to prkar1a ablation and not due to "inflammation" caused by adenovirus.

We used adenovirus driving CRE recombinase under the CMV promoter to ablate prkar1a in liver. We have examined prkar1a by immunoblot in metabolic relevant tissues (FIG. 3B of application and ref1 and also conducted sensitive RT-qPCR analysis of Kiss1 mRNA in a variety of tissues of Adv-GFP and Adv-CRE treated prkar1a fl/fl mice (Table 6). We have no evidence that in Adv-CRE treated mice, prkar1a recombination occurred in any tissue except in the liver (FIG. 3B) or that Kiss1 expression is altered in any tissue other than the liver (Table 6). Thus the effects seen are specific to recombination of prkar1a in liver and not due to artifacts of inflammation caused by adenovirus (consistent with many reports in this field of study).

TABLE 6

| Tissue | Prkar1a fl/ fl + Adv-GFP | L-Δprkar1a | |
|---|---|---|---|
| Heart | 1.2 ± 0.4 | 0.9 ± 0.2 | NS |
| Kidney | 1.1 ± 0.5 | 1.3 ± 0.3 | NS |
| Adipose tissue | 0.85 ± 0.4 | 1.0 ± 0.6 | NS |
| Pancreas islets | 0.9 ± 0.5 | 1.1 ± 0.4 | NS |
| Hypothalamus | 1.1 ± 0.3 | 1.2 ± 0.4 | NS |

98 We have a) determined by immunohistochemistry that Kiss1R is expressed at high levels in pancreatic β cells but not α-cells (FIG. 5 of application) and b) generated mice lacking Kiss in their pancreas by interbreeding Kiss fl/fl with PDX1 CRE mice. Synthetic kisspeptin (K54) suppressed GSIS from control islets (Kiss1R fl/fl) but not from Kiss1R ablated islets (FIG. 5 of application). Collectively we interpret these results to indicate that kisspeptin effects on GSIS are specific and mediated by the bona fide kisspeptin receptor Kiss1R.

We have completed the Kiss1 promoter studies and no longer propose to do these in this application. We have added both in vitro and in vivo studies to our originally proposed studies on interplay of kisspeptin with GLP-1/Exenind 4. We now also propose to examine the interplay between Kisspeptin and GIP on GSIS and β-cell mass regulation.

We have generated additional data on intracellular β-cell effects of kisspeptin. Kisspeptin reduces islet cAMP levels and thereby reduces IRS2 and PDX1, activates in islets the ER stress (ERS) and unfolded protein response (UPR) and downstream mediators TXNIP and CHOP (Table 5). In aim 2 of this application we aim to expand on these findings with the outlined in vitro and in vivo studies. We are particularly enthusiastic about these studies. While thus far insulin resistance and glucolipotoxicity have been shown to induce ERS/UPR on β-cells, our findings suggest that β-cell ERS/UPR is also stimulated by a novel endocrine mechanism by kisspeptin action. Thus, liver kisspeptin1 is not only linked to impaired GSIS but potentially also to β-cell ERS/UPR and untoward consequences such as apoptosis and reduction in β-cell mass.

Prophetic Examples of Experimental Methods. All genetic mouse models are currently available in the applicants' laboratories. Mouse studies are performed in C57Bl/6 adult male mice (6-8 weeks of age). Genotyping is performed by tail DNA PCR. Kiss1 KO (KissKO) mice47 are from S. Seminara, Harvard. Kiss1R fl/fl mice were generated in our laboratories. Littermate controls with appropriate genotypes are used. Studies are conducted at least on three separate occasions with different litters. Glucagon-CRE mice are from P. Herrera, University of Geneva. Pancreatic β-cell-specific ablation of floxed genes is achieved using 4-OH-tamoxifen (TAM) (200 ul of 20 μg/ml ip/day×5 days) administration in INS1-CRE-ERT48 transgenic mice (from L. Philipson, Univ. of Chicago). This mouse shows no recombination in the central nervous system or in non-B-cell pancreas tissue or in a large variety of tissues tested. TXNIP KO and CHOP KO are from Jackson Laboratories.

CRE recombinase transduction in mouse hepatocytes is achieved by tail vein injection of adenovirus (Adv-CRE) (MOI 109) expressing CRE recombinase under control of the CMV promoter (Gene Transfer Vector Core, Univ. Iowa). Recombination and target protein ablation are ascertained 3 days after transduction in liver immunoblots. Controls are injected with Adv or AAV-GFP.

Human pancreas sections, islet extracts, cultured islets and serum from non-diabetic and diabetic individuals are obtained from the National Disease Research Interchange (NDRI, PA). Additionally, we have access to de-identified samples from humans with T2DM and without diabetes, in whom plasma samples were taken in the post absorptive state as well as during an oral glucose tolerance. To avoid confounding samples from T2DM individuals with metformin, DPPIV inhibitors or incretin hormone were excluded. These samples are left over from studies funded by a separate source. These banked samples are used, in part, for studies outlined below.

Exendin-4, GIP, Kisppetin 54 are from Sigma. Antibodies for kisspeptin are from Millipore and for Kiss1R from Phoenix. ELISA for kisspeptin1 is from USCN life sciences and Phoenix. All other antibodies are from Abcam.

Research Aim 1. To test the hypothesis that kisspeptin1 suppresses GSIS by interaction via its receptor Kiss1R on β-cells, we examine: A) whether Kiss1 ablation ameliorates impaired GSIS in L-Δprkar1a, DIO and $Lepr^{db/db}$ mice; B) whether β-cell selective Kiss1R ablation ameliorates GSIS and glucose tolerance in DIO $Lepr^{db/db}$ mice; C) whether kisspeptin1 alters β-cell response (GSIS potentiation and/or proliferation) to incretin hormones glucagon-like peptide-1 (GLP-1) and to glucose-dependent insulinotropic peptide (GIP); and D) whether kisspeptin1 modulates glucagon secretion via Kiss1R on α-cells.

Rationale and Experimental Design 1A. Kisspeptin impairs GSIS in vitro, and liver kisspeptin production and circulating kisspeptin1 levels are elevated in L-Δprkar1a, DIO and $Lepr^{db/db}$ mice that exhibit impaired GT. Both chronic hyperglycemia and kisspeptin are thought to cause β-cell dysfunction and impair GSIS. Removing Kiss1 in L-Δprkar1a mice dissociates PKA-dependent upregulation of hepatic gluconeogenesis from kisspeptin1 production. Thus, this aim also permits examination of β-cell effects of chronic hyperglycemia separated from and without the effects of kisspeptin on GSIS. Removing Kiss1 in DIO and $Lepr^{db/db}$ mice allows examination of GSIS in absence of the negative effects of kisspeptin on GSIS and elucidates the relevance of HFD and caloric surfeit on B-cell function in T2DM. Inclusion of $Lepr^{db/db}$ controls for and removes the potentially confounding suppressive effects of leptin on GSIS. Leptin is also implicated in regulating hypothalamic Kiss1 expression 49. Inclusion of $Lepr^{db/db}$ mice elucidates whether leptin action modulates liver kisspeptin production and eliminate any such confounding effects of leptin. Thus, these studies permit elucidation of the contribution of HFD and caloric surfeit on β-cell (dys)function in absence of kisspeptin action.

KissKO mice are interbred with prkar1a fl/fl mice to generate KissKO/prkar1afl/fl mice. These are treated with Adv-CRE to generate KissKO/L-Δprkar1a mice. KissKO/prkar1afl/fl mice treated with Adv-GFP serve as controls.

For DIO and $Lepr^{db/db}$ studies, KissKO and control mice are placed on ND or HFD for 4, 8, 12 weeks; KissKO mice are interbred with Leprdb/db mice to t generate KissKO-$^{db/db}$ mice. Mice are tested at 4, 8, 12 weeks of age.

Mice are tested for weight, daily food intake, oral and ipGTT, insulin tolerance and in vivo GSIS. Plasma is harvested to determine insulin, glucagon, and kisspeptin-1 levels in the fasting and fed states. Pancreas tissue is examined for islet mass, α- and β-cell mass, proliferation marker Ki67 in α- and β-cells.

Rationale and Experimental Design 1B. Aim 1B is complementary to 1A. Instead of removing ligand, this aim examines inducible β-cell selective Kiss1R in DIO and $Lepr^{db/db}$ mice (L-Δprkar1a cannot be used in 1B because of CRE recombination in liver and β-cells will activate PKA signaling in both tissues and confound results). An important difference between Aims 1A and 1B is that aim 1B also eliminates the possibility of indirect kisspeptin effects on non-B-cell tissues. Kiss1R is ablated selectively on β-cells and remains intact in all other tissues. Ins-CRE-ERT and Kiss1R fl/fl50 mice are interbred. Tamoxifen (TMX) in corn oil treatment inducibly and selectively ablates Kiss in β-cells to generate β-ΔKiss1R mice. Littermates treated with corn oil without TMX serve as controls (=βCRE-ERT-Kiss1Rfl/fl mice). Successful ablation of Kiss1R from β-cells is confirmed by immunohistochemistry of pancreas sections as well as immunoblot of isolated islets (as in FIG. 19) of TMX treated mice. Mice are placed on SD or HFD for 4, 8, 12 weeks. To ablate β-cell Kiss1R in $Lepr^{db/db}$ mice, βCRE-ERT-Kiss1R fl/fl are interbred with $Lepr^{db/db}$. Homozygous offspring are treated with TMX or corn oil to generate, respectively, β-ΔKiss1R-$^{db/db}$ and βCRE-ERTKiss1Rfl/fl-$^{db/db}$ and tested at 4, 8, 12 weeks of age.

Mice are tested for weight, daily food intake, oral and ipGTT, insulin tolerance and in vivo GSIS. Plasma is harvested to determine insulin, glucagon, and kisspeptin-1 levels in the fasting and fed states. Pancreas tissue is examined for islet mass, α- and β-cell mass, proliferation marker Ki67 in α- and β-cells.

Rationale and Experimental Design 1C. Kisspeptin is elevated in diabetic mouse models and in humans with T2DM. Human T2DM is characterized by a resistance to endogenous incretin hormone action. Kisspeptin suppresses GSIS potentiation to the GLP-1 analogue exendin-4 in vitro in isolated islet cultures. It is unknown whether elevated kisspeptin levels in vivo impair GSIS potentiation in response to the incretin hormones GLP-1 and/or to GIP. This aim provides insight whether kisspeptin impairs β-cell proliferation in response to incretin hormone action.

In Vitro: Isolated cultured islets from β-ΔKiss1R and control βCRE-ERT-Kiss1Rfl/fl mice are examined for GSIS in static culture and perifusion studies. Islets are treated with K54 (10 nM) and are stimulated with the GLP-1 analogue E4 or with synthetic GIP at 0, 0.001, 0.01, 0.1, 1, 10 nM. GSIS, first and second phase GSIS and islet cAMP production are measured.

In Vivo: β-ΔKiss1R and control βCRE-ERT-Kiss1Rfl/fl mice are examined during oral GTT to provoke endogenous incretin hormone secretion. Plasma is collected for glucose, insulin, glucagon, kisspeptin, GLP-1 and GIP measurements at 0, 2, 5, 10, 20, 30, 60, 90 minutes. In addition, mice are treated with E4 or GIP 10 nM ip 30 minutes before an ipGTT and glucose, insulin, glucagon, kisspeptin, will be determined at 0, 2, 5, 10, 20, 30, 60, 90 minutes. To examine the proliferation response to incretin hormones: mice are treated with 10 nM E4 ip or GIP daily for 10 days to provoke β-cell proliferation. After dynamic testing as outlined above, pancreas morphometry is performed to examine islet mass, α- and B-cell mass, proliferation marker Ki67 in α- and β-cells.

Rationale and Experimental Design 1D. Kiss1R has previously been described to be expressed both on islet α- and β-cells. Our preliminary data suggests that in mice, α-cells do not express high levels of Kiss1R. We aim to directly resolve this uncertainty by ablating in vivo Kiss selectively on α-cells.

Glucagon-CRE and Kiss1R fl/fl mice are interbred to generate α-ΔKiss1R mice. Both Glucagon-CRE and Kiss1R fl/fl mice serve as controls. Plasma glucose, insulin, glucagon, kisspeptin levels are measured in the fed state and after an overnight fast as well as after refeeding for 4 hours. Pancreas morphometry is performed to examine islet mass, α- and β-cell mass, proliferation marker Ki67 in α- and β-cells. Plasma glucose, insulin and glucagon are determined after kisspeptin treatment (ip10 nM) at 0, 10, 20, 30, 40, 60 min to assess whether α-cell glucagon secretion is modulated by acute changes in kisspeptin action.

In vitro studies are also performed to assess direct and specific Kiss1R mediated effects on α-cells. Islets are isolated from control and α-ΔKiss1R mice and glucagon secretion is measured at baseline and in response to known glucagon secretagogue L arginine (0, 5, 10 pM) and whether K54 treatment (0, 5, 10 nM for 4, 12, 18 hours at each dose) modulates glucagon secretion in these assays is assessed.

Future Directions. High-throughput screen for KISS1R receptor antagonists, which would be large enough so as not to cross the blood brain barrier and presumably leave unaffected the hypothalamic GnRH regulation by kisspeptin. A Kiss1R receptor antagonist with these properties is evaluated for the treatment of β-cell dysfunction and diabetes mellitus in animal models as well as in non-human primates and potentially humans.

Generation of an inducible liver-specific kisspeptin ablation mouse model by CRE-LoxP technology. This mouse model allows specific hepatic Kiss1 ablation by Adv-CRE delivery and allows the examination of whether hepatic kisspeptin (as opposed to other potential tissue sources of kisspeptin) is responsible for mediating β-cell dysfunction in mouse models of impaired GSIS (DIO, db/db mice, and L-Δprkar1a mice).

Kiss1R signaling in β-cells. Kiss1R belongs to the A class of G-protein coupled receptors-similar to galanin and ghrelin receptors. Both galanin and ghrelin receptors are proposed to be coupled in β-cells to the intracellular G-protein Gαo, which inhibits cAMP synthesis. To examine whether KISS1R signals via Gαo, Gαo deficient islets are generated by interbreeding PDX1-CRE and/or INS-CRE-ERT mice with floxed Gαo mice 51,52 (from L. Birnbaumer, NIH, currently in our colony). We examine whether and to which extent kisspeptin agonist K10 suppresses GSIS in mice lacking Gαo in their islets or β-cells, respectively.

Research Aim 2. To test the hypothesis that prolonged kisspeptin1 action on islets in vitro and in vivo in mice induces in β-cells endoplasmic reticulum stress (ERS) and an unfolded protein response (UPR). We examine: A) whether effectors of the ERS/UPR are upregulated by in vitro and in vivo kisspeptin1 action on β-cells and whether the untoward UPR consequences of oxidative stress, inflammation and apoptosis markers are increased by kisspeptin1; in conjunction with the animal model in Aim 1A (KissKO/L-Δprkar1a), we also examine the role of hyperglycemia in absence of kisspeptin action on islet ERS/UPR, oxidative stress and apoptosis and whether hyperglycemia aggravates the kisspeptin effects on ERS/UPR; B) whether β-cell Kiss1R ablation in DIO and Lepr$^{db/db}$ mice protects them from ERS, UPR and B cell dysfunction and apoptosis; and C) whether mice lacking the UPR mediators TXNIP or CHOP (or their isolated islets) are protected from ERS/UPR and β-cell apoptosis induced by kisspeptin1.

Rationale and Experimental Design 2A. Kisspeptin action in vitro in mouse islets reduces cAMP levels, IRS2 and PDX1 expression and induces select markers of ERS and UPR as well as downstream mediators TXNIP and CHOP even in the absence of glucolipotoxic stressors. However, whether these kisspeptin effects are linked to apoptosis and additional downstream effects seen in T2DM, such as loss of MafA, Nkx6.153 expression and apoptosis is unclear. Further, it is unclear whether and to which extent chronic in vivo hyperglycemia alone in absence of kisspeptin action causes β-cell ERS/UPR, oxidative stress and apoptosis.

Isolated islets from WT mice and from β-ΔKiss1R mice are treated with K54 at 0, 5, 10 nM for 0, 24, 48, 72 hours in 5 and 10 mM glucose. Thapsigargin (200 nM) and tunicamycin (50 ng/ml) treated islets serve as positive controls for ERS/UPR induction. Islet cAMP levels are measure by ELISA. mRNA expression is examined by RT-qPCR and protein expression by immunoblot of islet protein of reduced cAMP signaling, ERS/UPR, oxidative stress, NLRP3-I associated markers as listed in FIG. 15, and Table 5. Immunoblots for cleaved Bcl2, Bclx, caspase 1 and 3 further provide a maker for activated apoptosis. MafA, Nkx61 and PDX1 serve as cell differentiation markers. We fix, embed, and examine the immunohistochemistry ERS/UPR markers (ATF6, phospho eIF2a, sXBP1), apoptosis markers (cleaved caspase 3, TUNEL) and proliferation makers (Ki67, PCNA) in WT and β-ΔKiss1R mice exposed to K54 and glucose. Transmission electron microscopy of islets are used to examine ultrastructural changes compatible with ER stress.

In parallel studies, we examine whether co-incubation of islets with incretin hormone agonists E4 (10 nM) or GIP (10 nM) ameliorates or delays kisspeptin mediated ERS/UPR and apoptosis.

For in vivo studies involving increased liver kisspeptin production WT mice are injected with AAV-Alb-Kiss1 and controls with AAV-Alb-GFP. AAV expression is maintained for several months and allows examination of effects and time-course of chronic high kisspeptin levels. Mice are be tested at 2, 4, 8, 12 16, 20 weeks after AAV/Alb-Kiss1 or -Alb-GFP treatment for body weight, daily caloric intake, oGTT, ipGTT ITT, GSIS. Islet and β-cell mass, proliferation and apoptosis activity are determined by pancreas morphometry. Islets from these mice are harvested for measurements of cAMP and determination of ERS, UPR, oxidative stress and NLRP3 inflammasome associated markers as outlined above. It is anticipated that kisspeptin overexpression results in impaired GSIS and in hyperglycemia, which may confound the effects of kispetin in islets. If hyperglycemia occurs, hyperglycemia is controlled by treating mice with phloridzin (an inhibitor of the renal tubule Na+ D-glucose transporter, treatment with which results in renal glucose loss and normoglycemia) 0.4 g/kg twice daily×2 weeks. Thus, with this approach we are able to examine the effects of chronic hyper-kisspeptinemia separately from chronic hyperglycemia. Mice are placed on phloridzin.

To examine the role of chronic hyperglycemia in the absence of kisspeptin action on β-cell ERS/UPR and untoward consequences in β-cell function and -mass, parallel studies are performed in KissKO/L-Δprkar1a mice (see also Aim 1A) as outlined above.

Rationale and Experimental Design 2B. Kisspeptin stimulates ERS/UPR in vitro in islets. Pancreas Kiss1R ablation ameliorates GT and GSIS in DIO mice. DIO and Lepr$^{db/db}$ mice exhibit ERS/UPR, β-cell apoptosis and loss of PDX1, MafA and Nkx6.1. Whether and to which extent Kiss1R ablation on β-cells will prevent or delay these changes on β-cells, GSIS and GT remains unknown. These studies are important to evaluate the potential utility of Kiss1R antagonists in treating T2DM.

β-ΔKiss1R, βCRE-ERT-Kiss1R fl/fl, β-ΔKiss1 R$^{db/db}$ and βCRE-ERT-Kiss1R fl/fl$^{db/db}$ mice are generated as outlined in Aim 1. β-ΔKiss1R, βCRE-ERT-Kiss1R fl/fl mice are placed on SD or HFD for 4, 8, 12, 16, 20 weeks.

We examine at 0, 2, 4, 8, 12, 16, 20 weeks daily caloric intake, body weight, ipGTT, in vivo GSIS and plasma glucagon levels. Pancreas morphometry assesses α- and β-cell mass. We examine by immunohistochemistry ERS/UPR markers (ATF6, phospho eIF2a, sXBP1), apoptosis markers (cleaved caspase 3, TUNEL) and proliferation makers (Ki67, PCNA) in pancreas sections from these mice at different time points after AAV treatment. Transmission electronmicroscopy of pancreas tissue is used to examine ultrastructural changes compatible with ER stress. Islets extracted from these mice are analyzed by RTqPCR and protein expression by immunoblot of islet protein of reduced cAMP signaling, ERS/UPR, oxidative stress, NLRP3-I associated markers as listed in FIG. 15, and Table 5, as well as apoptosis markers Bcl2, Bclx, caspase 1 and 3. Furthermore, we examine whether β-cell Kiss1 R deficiency protects mice in Aim 2B from loss of β-cell differentiation makers MafA and Nkx6.1.

Rationale and Experimental Design 2C. Kisspeptin action in vitro in mouse islets reduces IRS2 and PDX1 expression and induces select markers of ERS and UPR as well as downstream mediators TXNIP and CHOP. TXNIP and CHOP are separately implicated in β-cell demise in T2DM. This subaim dissects the roadmap linking β-cell kisspeptin effects on TXNIP and CHOP and whether TXNIP, CHOP or both mediate kisspeptin induced β-cell demise.

Isolated islets from WT mice, CHOP KO and TXNIP KO are treated with K54 at 0, 5, 10 nM for 0, 24, 48, 72 hours. Thapsigargin (200 nM) and tunicamycin (50 ng/ml) treated islets serve as positive controls for ERS induction. We examine mRNA expression by RT-qPCR and protein expression by immunoblot of islet protein of reduced cAMP signaling, ERS/UPR, oxidative stress, NLRP3-I associated markers as listed in FIG. 15, and Table 5. Immunoblots for cleaved Bcl2, Bclx, caspase 1 and 3 further provide a marker for activated apoptosis.

For in vivo studies, WT, CHOP KO and TXNIP KO mice are treated with AAV-Alb-Kiss1 or AAV-Alb-GFP (control). We examine at 0, 2, 4, 8, 12 weeks after AAV treatment daily caloric intake, body weight, ipGTT, in vivo GSIS and plasma glucagon levels. Pancreas morphometry will assess α- and β-cell mass. We examine by immunohistochemistry ERS/UPR, oxidative stress NLRP3-I markers (see above) (ATF6, phospho eIF2a, sXBP1), apoptosis markers (cleaved caspase 3, TUNEL) and proliferation makers (Ki67, PCNA) in pancreas sections from these mice at different time points after AAV treatment. Transmission electron microscopy of pancreas tissue is used to examine ultrastructural changes compatible with ER stress. Islets extracted from these mice are analyzed by RT-qPCR and protein expression by immunoblot of islet protein of reduced cAMP signaling, ERS/UPR, oxidative stress, NLRP3-I associated markers as listed in FIG. 15, and Table 5, as well as apoptosis markers Bcl2, Bclx, cleaved caspase 1 and 3. Furthermore, we examine whether CHOP or TXNIP deficiency protects mice treated with AAV-Alb-Kiss1 from loss of β-cell differentiation makers PDX1, MafA and Nkx6.1.

Future directions. 1. Do fatty acids augment kisspeptin effects on β-cell ERS/UPR. To directly test the effects of "lipotoxicity" on kisspeptin effects and as extension of Aim 2A, we examine whether incubation of islets with fatty acids oleate or palmitate increases the effects of kisspeptin on ERS/UPR, NLRP3 inflammasome activation and apoptosis. 2. Development of a kisspeptin antagonist or a Kiss1 receptor blocker for treatment of impaired GSIS and prevention of β-cell loss in T2DM (see above). 3. Evaluation of pharmacologic agents, which counteract glucagon-dependent signaling in liver such as metformin in regulating liver kisspeptin expression. Metformin interferes with glucagon signaling in the liver. We evaluate whether metformin modulates kisspeptin production in models of T2DM: DIO and Lepr$^{db/db}$ mice. 4. Generation of a mouse model with inducible and liver specific activation of kisspeptin production (CMV-fl-stop-fl-Kiss1 mouse). We examine whether chronic hepatic kisspeptin production in vivo results in β-cell dysfunction, reduced GSIS, impaired glucose homeostasis, as well as changes in response to secretagogue effects of incretin GLP-1 analogue exendin-4. We also examine whether chronic in vivo hepatic kisspeptin over-production will cause changes in β-cell mass (apoptosis?), -proliferation, and β-cell (de)differentiation.

Transgenic mice harboring a DNA cassette containing mouse kisspeptin cDNA under control of the CMV promoter are generated. Between the CMV promoter and the kisspeptin cDNA start site codon a floxed stop codon (CMV-fl-stop-fl-Kiss1 mouse) is inserted. 3' of the Kiss1 cDNA is a polyA site for RNA stabilization. Thus, the transgene does not produce kisspeptin until removal of the stop codon by CRE recombinase. In a second step, hepatic kisspeptin production is activated in adult mice by Adv-CRE transduction to the liver (L-Kiss1 mouse). Littermates receiving Adv-GFP serves as controls. Additional interbreeding of the L-Kiss1 mouse with Kiss1 KO mouse allows subtraction of any potentially confounding endogenous (non-transgenic) and extrahepatic kisspeptin expression.

At least 5 transgenic lines are tested. Hepatic Kiss1 expression (after CRE recombinase transduction) is assessed by qRT-PCR, immunoblot. Plasma kisspeptin is determined by ELISA. Analysis of mouse lines with different serum kisspeptin activities allows us to assess effects of chronic kisspeptin oversupply at different concentrations on glucose homeostasis, β-cell mass, -proliferation, -survival, -differentiation status and -function.

Research Aim 3. To test the hypothesis that circulating kisspeptin1 is elevated in human T2DM, that kisspeptin1 impairs GSIS and response to incretins, and/or induces ERS/UPR in human islets, we will examine: A) kisspeptin1, insulin, glucagon levels in the post-absorptive state and during an oral glucose tolerance test in humans with and without T2DM; B) whether Kiss1R is present on human pancreatic endocrine cells and its co-localization with insulin or other hormones, C) the interplay of kisspeptin1 and GLP-1 or GIP receptor activation on cAMP synthesis and GSIS potentiation in human islets, and D) whether kisspeptin1 impairs GSIS and induces ERS/UPR in isolated and cultured human islets. The main rationale for Aim 3 is to assess whether the findings in inbred mouse models are replicated in humans.

Experimental Procedure 3A. We have access to de-identified banked plasma and serum samples of male humans without (n=10) and with diagnosed T2DM (n=10). These subjects were not on any treatment with metformin or incretin analogue therapy. Samples were taken in the post-absorptive state as well as during an oral GTT (75 g po) at 0, 10, 20, 30, 60, 90, 120 min. In these samples, we measure glucose, insulin, glucagon as well as kisspeptin levels.

Experimental Procedure 3B. Formalin fixed, paraffin embedded pancreas sections from cadaveric human donors without and with T2DM (NDRI) are analyzed for Kiss1R expression by immunohistochemistry combined with confocal microscopy. Co-staining with insulin, glucagon, somatostatin and PP allows us to examine to which endocrine subset Kiss1R is localized in human pancreas.

Experimental Procedure 3C and 3D. Human islets are obtained through the NIH sponsored islet distribution channels and/or NDRI. Human islets are treated with K54 at 0, 5, 10 nM for 0, 24, 48, 72 hours. Thapsigargin (200 nM) and tunicamycin (50 ng/ml) treated islets serve as positive controls for ERS induction. We examine mRNA expression by RT-qPCR and protein expression by immunoblot of islet protein of reduced cAMP signaling: INS1, INS2, IRS2, PDX1, ERS markers: CHOP, PDI, total XBP1, spliced XBP1, oxidative stress markers: Nrf1, Nrf2, catalase, SOD1, SOD2, HMOX1, and NLRP3 inflammasome associated markers TXNIP, ATF5, IL1β activated apoptosis markers Bcl2, Bclx, cleaved caspase 1 and 3

Future Directions. 1. Human placenta produces high quantities of kisspeptin. Whether kisspeptin contributes to gestational diabetes in susceptible individuals is unknown. Evaluation of kisspeptin levels in gestational diabetes and correlation with insulin secretion during glucose tolerance tests may provide further insight into the potential contribution of kisspeptin in the pathogenesis of gestational diabetes. 2. Direct infusion of Kisspeptin K54 into non-human primates (NHP) (*Macaca Mulatta*). To this end, we are preparing protocols for studies to be conducted at the NHP center at the university of Wisconsin, Madison.

Intravenous infusion of kisspeptin K54 to human subjects and examine GSIS and glucose tolerance. Interpretation of Results. Previously published methods and interpretation by the applicants are available, and are therefore not be extensively discussed. Statistical analysis: all data are analyzed using PrismGraph software (Students t-Test, analysis of variance ANOVA with Bonferroni correction where applicable). Data are calculated as mean and standard error of the mean (SEM). A $p<0.05$ is considered as statistically significant. Studies conducted on at least three separate occasions are used for interpretation of data.

qRT-PCR is analyzed using the A-Act method 57 using housekeeping genes (18S, GAPDH) as controls. Increased values indicate primarily increased mRNA levels and secondarily increased transcription of the corresponding gene. Immunoblot quantification: immunoblot bands are analyzed for density using the BioRad XR imaging system and software. Bands with higher intensity normalized to appropriate controls (actin, tubulin) are interpreted as higher corresponding antigen in that specific sample and vice versa.

Pancreas histological measurements: Larger islet mass and β-cell mass indicate increased β-cell proliferation and/or reduced β-cell apoptosis. Immunostaining for insulin and non-insulin endocrine cells on pancreas sections permit analogous assessment of non-β-cell islet cell populations. Changes in proliferation markers are interpreted according to direction of change and by verifying whether changes in Ki67 and PCNA point in the same direction of change. Increased appearance of apoptosis markers (TUNEL assay, activated caspase 3) indicate increased apoptosis; and when detected in conjunction with increased proliferation makers are interpreted as increased β-cell turnover.

In vivo glucose and insulin levels during fasting and physiologic tests. Elevated glucose levels in light of reduced insulin levels in fasting animals or during glucose tolerance test are as reduced GSIS. Elevated glucose together with elevated insulin levels are interpreted as increased insulin resistance either at the level of the hepatocyte or in peripheral tissues. Quantification is performed by calculating area under the curve (AUC) and of glucose and insulin serum levels determined during ipGTT. Decreased glucose levels in the fasting state or during glucose tolerance tests together with increased insulin levels are interpreted as increased insulin secretion. Increased/decreased insulin AUC during the first 10 minutes is interpreted as increased/decreased first phase insulin secretion, respectively. Increased/decreased insulin AUC during minutes 10-120 is interpreted as increased/decreased second phase insulin secretion, respectively.

Glucose-stimulated insulin secretion from isolated islets: Insulin secretion from islets in static culture (10 mM glucose) is performed as described 38,39,41. Insulin concentration in the supernatant is normalized to islet insulin content and percent insulin released is calculated. Higher insulin concentration in the supernatant is interpreted as increased GSIS. Lower insulin concentration in the supernatant is interpreted as decreased GSIS.

Perifusion studies are performed as previously described. Insulin concentration in the perifusate is measured at 1-2 minute intervals. Higher insulin concentration in the supernatant is interpreted as increased GSIS. Lower insulin concentration in the supernatant is interpreted as decreased GSIS. First and second phase GSIS will be defined, respectively as GSIS from 0-10 or after 11 min.

Hepatic Glucagon Receptor Signaling Stimulates the Production of the Neurotransmitter Kisspeptin Our surprising findings indicate that hepatic glucagon receptor signaling stimulates the production of the neurotransmitter kisspeptin by the liver. Kisspeptin reaches the pancreatic β-cells via the circulation, where it binds to its cognate receptor GPR54 and inhibits glucose-stimulated insulin secretion (GSIS) and diminishes β-cell response to incretin action. Furthermore, administration of a GPR54 receptor antagonist potently ameliorates glucose homeostasis in a mouse model of T2DM.

Our findings have potentially wide-ranging significance for understanding the pathogenesis of and for developing novel therapies for diabetes mellitus. More specifically, the present disclosure multiple innovative concepts as well as novel mouse models including, but not limited, to:

1. Description of a thus far unrecognized metabolically active gene-product regulated by glucagon receptor signaling in the liver. A novel pancreatic α-cell to hepatocyte regulatory pathway of kisspeptin synthesis and secretion.

2. Description of elevated hepatic Kiss1 expression and kisspeptin serum activity in the DIO glucose intolerant mouse as well as in db/db and ob/ob diabetic mouse models.

3. Description of a novel hepatocyte to β-cell endocrine signaling mechanism via kisspeptin to its cognate receptor GPR54 to suppress β-cell glucose stimulated insulin secretion—i.e., β-cell dysfunction- and β-cell cAMP synthesis.

4. Use of a GPR54 receptor antagonist K234 to ameliorate diabetes mellitus and glucose tolerance in a mouse model of diabetes mellitus.

5. Development of a cell based bioassay for accurate measurements of circulating serum kisspeptin bioactivity.

6. Generation of a floxed glucagon receptor mouse model.

7. Generation of a floxed GPR54 receptor mouse models.

8. Generation of a mouse model with inducible and liver-specific activation of kisspeptin production Accordingly, based on the above outlined considerations on β-cell dysfunction and hyperglucagonemia, we reasoned that glucagon receptor-mediated signaling in the liver is required to initiate β-cell dysfunction and to impair glucose-stimulated insulin secretion. We therefore inducibly disinhibited cAMP-PKA signaling in vivo in adult mouse liver by ablating hepatic protein kinase A regulatory subunit 1A (prkar1a) by adenovirus mediated hepatic CRE recombinase transduction in floxed prkar1a mice (L-Δprkar1a mice) 14 (FIG. 22A). Upregulation of hepatic cAMP-PKA signaling within 3 days stimulated hepatic gluconeogenesis causing increase in fasting glucose levels and insufficient insulin secretion to correct glycemia. Conversely, identical baseline fasting glycemia achieved in mice by continuous exogenous glucose infusion for 3 days 15 (D-glucose mice) was associated with increased insulin secretion and relatively mild impairment of glucose tolerance despite continued exogenous glucose infusions (FIG. 22B). Differential hepatic gene expression analysis between these two mouse models identified the gene encoding the secreted neuropeptide kisspeptin-1 (Kiss1) to be markedly elevated (8× on mRNA array, 15× on qRT-PCR) in L-Δprkar1a but not in D-glucose mice (FIG. 22C). Glucagon administration in normal mice also increased hepatic Kiss1 expression within 30 minutes (FIG. 23). Remarkably, high fat diet induced obese and glucose intolerant (HFD/DIO) mice showed hepatic Kiss1 expression, which increased with the duration of exposure to HFD (FIG. 24A). Hepatic Kiss1 increased when mice are fasted (i.e, had elevated glucagon levels 16, FIG. 24B). Mouse models of T2DM associated with hyperglucagonemia, db/db and ob/ob diabetic mice also exhibited significantly increased hepatic Kiss1 gene expression (FIG. 24B). In these mouse models, low amounts of Kiss1 transcript was detectable in adipose tissue, but were completely absent in adipose tissue form ob/ob and db/db mice (not shown). Primary mouse hepatocytes treated with forskolin (100 µM)/IBMX (200 µM) to mimic glucagon cAMP-PKA signaling showed as expected increased Pgc1a and also increased Kiss1 expression (FIG. 25). The kisspeptin receptor Gpr54 expression was detected at significant levels in pancreatic islets (FIG. 26). Exposure of WT islets to the biologically fully active 10 amino acid C-terminal kisspeptin fragment K10 (10 nM) suppressed GSIS (FIG. 27). Moreover, in this functional bioassay, isolated wild-type (WT) mouse islets exhibited reduced cAMP production when treated with the GPR54 agonist K10—an effect, which was partially reversed by administering the glucagon-like peptide-1 receptor agonist exendin-4 (FIG. 28). WT islets exposed to 10% serum extracted from L-Δprkar1a, db/db and ob/ob mice also exhibited impaired GSIS, which recovered by additional co-incubation with the GPR54 receptor antagonist K234 (Roseweir et al., 29 J. NEUROSCI. 3920-29 (2009)) (FIG. 29). Directly testing the in vivo effects of kisspeptin on GSIS, K10 administration in mice impaired glucose tolerance and suppressed GSIS (FIG. 30). Importantly, db/db diabetic mice, which have elevated hepatic Kiss1 expression, exhibit a dramatic improvement in glucose tolerance when treated with kisspeptin receptor GPR54 antagonist K234 (FIG. 31).

Taken together, our preliminary data indicate that kisspeptin is produced in the liver in response to glucagon action, is elevated in DIO glucose intolerant and diabetic mice and potently suppresses β-cell GSIS via direct action on GPR54, which is expressed on β-cells.

We claim:

1. A method for treating type 2 diabetes or pre-diabetes in a patient comprising the step of administering to the patient a composition comprising an effective amount of a GPR54 receptor antagonist selected the group consisting of 2-Acylamino-4,6-diphenylpyridine and a small molecule derivative thereof.

2. A method for treating type 2 diabetes mellitus or pre-diabetes in a patient comprising administering to the patient a composition comprising an effective amount of a kisspeptin1 proteolytic derivative comprising SEQ ID NO:36.

3. A method for treating type 2 diabetes mellitus or pre-diabetes in a patient comprising administering to the patient a composition comprising an effective amount of a kisspeptin1 derivative comprising SEQ ID NO: 37.

4. The method of claim 1, wherein the functional derivative does not cross the blood brain barrier.

5. The method of claim 2, wherein the kisspeptin1 proteolytic derivative does not cross the blood brain barrier.

6. The method of claim 3, wherein the kisspeptin1 proteolytic derivative does not cross the blood brain barrier.

7. The method of claim 1, wherein the Kisspeptin derivative comprises SEQ ID NO:37.

8. The method of claim 2, wherein the Kisspeptin derivative comprises SEQ ID NO:37.

9. The method of claim 3, wherein the Kisspeptin derivative comprises SEQ ID NO:37.

* * * * *

```
                        SEQUENCE LISTING

<160> NUMBER OF SEQ ID NOS: 37

<210> SEQ ID NO 1
<211> LENGTH: 21
<212> TYPE: DNA
<213> ORGANISM: Mus musculus

<400> SEQUENCE: 1
gctctctctc tttgacctag g                                       21

<210> SEQ ID NO 2
<211> LENGTH: 20
<212> TYPE: DNA
<213> ORGANISM: Artificial Sequence
<220> FEATURE:
<223> OTHER INFORMATION: Prkar1a fl/fl forward primer

<400> SEQUENCE: 2
gcaggcgagc tattagttta                                         20

<210> SEQ ID NO 3
<211> LENGTH: 21
<212> TYPE: DNA
<213> ORGANISM: Artificial Sequence
<220> FEATURE:
<223> OTHER INFORMATION: Prkar1a fl/fl reverse primer

<400> SEQUENCE: 3
catccatctc ctatcccctt t                                       21

<210> SEQ ID NO 4
```

```
<211> LENGTH: 21
<212> TYPE: DNA
<213> ORGANISM: Artificial Sequence
<220> FEATURE:
<223> OTHER INFORMATION: Kiss1R fl/fl forward primer

<400> SEQUENCE: 4
ttcgtgaact acatccagca g                                              21

<210> SEQ ID NO 5
<211> LENGTH: 20
<212> TYPE: DNA
<213> ORGANISM: Artificial Sequence
<220> FEATURE:
<223> OTHER INFORMATION: Kiss1R fl/fl reverse primer

<400> SEQUENCE: 5
agagtggcac atgtggcttg                                                20

<210> SEQ ID NO 6
<211> LENGTH: 24
<212> TYPE: DNA
<213> ORGANISM: Artificial Sequence
<220> FEATURE:
<223> OTHER INFORMATION: Gcgr fl/fl forward primer

<400> SEQUENCE: 6
tcacccgtga tgatcccatg tctt                                           24

<210> SEQ ID NO 7
<211> LENGTH: 24
<212> TYPE: DNA
<213> ORGANISM: Artificial Sequence
<220> FEATURE:
<223> OTHER INFORMATION: Gcgr fl/fl reverse primer

<400> SEQUENCE: 7
agtggctcac agtgcctatt caga                                           24

<210> SEQ ID NO 8
<211> LENGTH: 19
<212> TYPE: DNA
<213> ORGANISM: Artificial Sequence
<220> FEATURE:
<223> OTHER INFORMATION: Insr fl/fl forward primer

<400> SEQUENCE: 8
gatgtgcacc ccatgtctg                                                 19

<210> SEQ ID NO 9
<211> LENGTH: 20
<212> TYPE: DNA
<213> ORGANISM: Artificial Sequence
<220> FEATURE:
<223> OTHER INFORMATION: Insr fl/fl reverse primer

<400> SEQUENCE: 9
ctgaatagct gagaccacag                                                20

<210> SEQ ID NO 10
<211> LENGTH: 24
<212> TYPE: DNA
<213> ORGANISM: Artificial Sequence
<220> FEATURE:
<223> OTHER INFORMATION: Lepr db/db forward primer

<400> SEQUENCE: 10
```
agaacggaca ctctttgaag tctc                                          24

<210> SEQ ID NO 11
<211> LENGTH: 25
<212> TYPE: DNA
<213> ORGANISM: Artificial Sequence
<220> FEATURE:
<223> OTHER INFORMATION: Lepr db/db reverse primer

<400> SEQUENCE: 11
cattcaaacc atagtttagg tttgt                                         25

<210> SEQ ID NO 12
<211> LENGTH: 19
<212> TYPE: DNA
<213> ORGANISM: Artificial Sequence
<220> FEATURE:
<223> OTHER INFORMATION: Kiss1 forward primer

<400> SEQUENCE: 12
gcataccgcg attccttttt                                               19

<210> SEQ ID NO 13
<211> LENGTH: 20
<212> TYPE: DNA
<213> ORGANISM: Artificial Sequence
<220> FEATURE:
<223> OTHER INFORMATION: Kiss1 reverse primer

<400> SEQUENCE: 13
agctgctgct tctcctctgt                                               20

<210> SEQ ID NO 14
<211> LENGTH: 19
<212> TYPE: DNA
<213> ORGANISM: Artificial Sequence
<220> FEATURE:
<223> OTHER INFORMATION: Gcgr forward primer

<400> SEQUENCE: 14
tgctgtttgt catcccctg                                                19

<210> SEQ ID NO 15
<211> LENGTH: 21
<212> TYPE: DNA
<213> ORGANISM: Artificial Sequence
<220> FEATURE:
<223> OTHER INFORMATION: Gcgr reverse primer

<400> SEQUENCE: 15
caggaagaca ggaatacgca g                                             21

<210> SEQ ID NO 16
<211> LENGTH: 23
<212> TYPE: DNA
<213> ORGANISM: Artificial Sequence
<220> FEATURE:
<223> OTHER INFORMATION: Kiss1R forward primer

<400> SEQUENCE: 16
gcaaattcgt caactacatc cag                                           23

<210> SEQ ID NO 17
<211> LENGTH: 21
<212> TYPE: DNA

```
<213> ORGANISM: Artificial Sequence
<220> FEATURE:
<223> OTHER INFORMATION: Kiss1R reverse primer

<400> SEQUENCE: 17
gggaacacag tcacatacca g                                              21

<210> SEQ ID NO 18
<211> LENGTH: 20
<212> TYPE: DNA
<213> ORGANISM: Artificial Sequence
<220> FEATURE:
<223> OTHER INFORMATION: 18sRNA forward primer

<400> SEQUENCE: 18
gcaattattc cccatgaacg                                                20

<210> SEQ ID NO 19
<211> LENGTH: 20
<212> TYPE: DNA
<213> ORGANISM: Artificial Sequence
<220> FEATURE:
<223> OTHER INFORMATION: 18sRNA reverse primer

<400> SEQUENCE: 19
ggcctcacta aaccatccaa                                                20

<210> SEQ ID NO 20
<211> LENGTH: 20
<212> TYPE: DNA
<213> ORGANISM: Artificial Sequence
<220> FEATURE:
<223> OTHER INFORMATION: Actin forward primer

<400> SEQUENCE: 20
agccatgtac gtagccatcc                                                20

<210> SEQ ID NO 21
<211> LENGTH: 20
<212> TYPE: DNA
<213> ORGANISM: Artificial Sequence
<220> FEATURE:
<223> OTHER INFORMATION: Actin reverse primer

<400> SEQUENCE: 21
ctctcagctg tggtggtgaa                                                20

<210> SEQ ID NO 22
<211> LENGTH: 20
<212> TYPE: DNA
<213> ORGANISM: Artificial Sequence
<220> FEATURE:
<223> OTHER INFORMATION: Ppargc1a forward primer

<400> SEQUENCE: 22
cagcctcttt gcccagatct                                                20

<210> SEQ ID NO 23
<211> LENGTH: 20
<212> TYPE: DNA
<213> ORGANISM: Artificial Sequence
<220> FEATURE:
<223> OTHER INFORMATION: Ppargc1a reverse primer

<400> SEQUENCE: 23
ccgctagcaa gtttgcctca                                                20
```

<210> SEQ ID NO 24
<211> LENGTH: 22
<212> TYPE: DNA
<213> ORGANISM: Artificial Sequence
<220> FEATURE:
<223> OTHER INFORMATION: Src1 forward primer

<400> SEQUENCE: 24
aggagtgata gagaaggagt cg                                              22

<210> SEQ ID NO 25
<211> LENGTH: 22
<212> TYPE: DNA
<213> ORGANISM: Artificial Sequence
<220> FEATURE:
<223> OTHER INFORMATION: Src1 reverse primer

<400> SEQUENCE: 25
tgattgtaac ccaagtagct gg                                              22

<210> SEQ ID NO 26
<211> LENGTH: 21
<212> TYPE: DNA
<213> ORGANISM: Artificial Sequence
<220> FEATURE:
<223> OTHER INFORMATION: Pck1 forward primer

<400> SEQUENCE: 26
ctgcataacg gtctggactt c                                               21

<210> SEQ ID NO 27
<211> LENGTH: 19
<212> TYPE: DNA
<213> ORGANISM: Artificial Sequence
<220> FEATURE:
<223> OTHER INFORMATION: Pck1 reverse primer

<400> SEQUENCE: 27
cagcaactgc ccgtactcc                                                  19

<210> SEQ ID NO 28
<211> LENGTH: 19
<212> TYPE: DNA
<213> ORGANISM: Artificial Sequence
<220> FEATURE:
<223> OTHER INFORMATION: G6P forward primer

<400> SEQUENCE: 28
cagcaactgc ccgtactcc                                                  19

<210> SEQ ID NO 29
<211> LENGTH: 20
<212> TYPE: DNA
<213> ORGANISM: Artificial Sequence
<220> FEATURE:
<223> OTHER INFORMATION: G6P reverse primer

<400> SEQUENCE: 29
gttgaaccag tctccgacca                                                 20

<210> SEQ ID NO 30
<211> LENGTH: 18
<212> TYPE: DNA
<213> ORGANISM: Artificial Sequence
<220> FEATURE:

<223> OTHER INFORMATION: Kiss1pr CRE1 forward primer

<400> SEQUENCE: 30 tgtcgtctttt ggcttcct                                      18

<210> SEQ ID NO 31
<211> LENGTH: 17
<212> TYPE: DNA
<213> ORGANISM: Artificial Sequence
<220> FEATURE:
<223> OTHER INFORMATION: Kiss1pr CRE1 reverse primer

<400> SEQUENCE: 31
tgcacctagg gtagcac                                        17

<210> SEQ ID NO 32
<211> LENGTH: 17
<212> TYPE: DNA
<213> ORGANISM: Artificial Sequence
<220> FEATURE:
<223> OTHER INFORMATION: Kiss1pr CRE2 forward primer

<400> SEQUENCE: 32
aggcgagtgc cttgaac                                        17

<210> SEQ ID NO 33
<211> LENGTH: 21
<212> TYPE: DNA
<213> ORGANISM: Artificial Sequence
<220> FEATURE:
<223> OTHER INFORMATION: Kiss1pr CRE2 reverse primer

<400> SEQUENCE: 33
ccactttctt ctggacttgg a                                   21

<210> SEQ ID NO 34
<211> LENGTH: 54
<212> TYPE: PRT
<213> ORGANISM: Homo sapiens

<400> SEQUENCE: 34

Gly Thr Ser Leu Ser Pro Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 35
<211> LENGTH: 10
<212> TYPE: PRT
<213> ORGANISM: Homo sapiens

<400> SEQUENCE: 35

Tyr Asn Trp Asn Ser Phe Gly Leu Arg Phe
1               5                   10

<210> SEQ ID NO 36
<211> LENGTH: 10
<212> TYPE: PRT
<213> ORGANISM: Artificial Sequence
<220> FEATURE:

```
<223> OTHER INFORMATION: Kisspeptin 234
<220> FEATURE:
<221> NAME/KEY: MISC_FEATURE
<222> LOCATION: (1)..(1)
<223> OTHER INFORMATION: D-Alanine
<220> FEATURE:
<221> NAME/KEY: MISC_FEATURE
<222> LOCATION: (8)..(8)
<223> OTHER INFORMATION: D-Tryptophan

<400> SEQUENCE: 36

Ala Asn Trp Asn Gly Phe Gly Trp Arg Phe
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Consensus sequence for Kisspeptin antagonist
<220> FEATURE:
<221> NAME/KEY: MISC_FEATURE
<222> LOCATION: (1)..(1)
<223> OTHER INFORMATION: X is D-Alanine
<220> FEATURE:
<221> NAME/KEY: MISC_FEATURE
<222> LOCATION: (2)..(2)
<223> OTHER INFORMATION: X is Asn, D-Alanine or D-Tryptophan
<220> FEATURE:
<221> NAME/KEY: MISC_FEATURE
<222> LOCATION: (3)..(3)
<223> OTHER INFORMATION: X is Tryptophan, D-Tryptophan or D-Alanine
<220> FEATURE:
<221> NAME/KEY: MISC_FEATURE
<222> LOCATION: (8)..(8)
<223> OTHER INFORMATION: X is D-Leucine, D-Phenylalanine or D-Typtophan

<400> SEQUENCE: 37

Xaa Xaa Xaa Asn Gly Phe Gly Xaa Arg Phe
1               5                   10
```